US005194605A

United States Patent [19]

Greenlee et al.

[11] Patent Number: 5,194,605

[45] Date of Patent: Mar. 16, 1993

[54] CYCLIC RENIN INHIBITORS CONTAINING 2-SUBSTITUTED (3S,4S)-4-AMINO-5-CYCLOHEXYL-3-HYDROXY PENTANOIC ACID, 2-SUBSTITUTED (3S,4S)-5-CYCLOHEXYL-3,4-DI-HYDROXY PENTANOIC ACID OR 2-SUBSTITUTED (4S,5S)-5-AMINO-6-CYCLOHEXYL-4-HYDROXYHEXANOIC ACID OR ITS ANALOGS

[75] Inventors: William J. Greenlee, Teaneck; Ralph A. Rivero, Eatontown; Ann E. Weber, Scotch Plains; Lihu Yang, Woodbridge, all of N.J.

[73] Assignee: Merck & Co., Inc., Rahway, N.J.

[21] Appl. No.: 714,115

[22] Filed: Jun. 11, 1991

Related U.S. Application Data

[63] Continuation-in-part of Ser. No. 618,602, Nov. 30, 1990, abandoned, which is a continuation-in-part of Ser. No. 559,866, Jul. 27, 1990, abandoned, which is a continuation-in-part of Ser. No. 448,175, Dec. 8, 1989, abandoned.

[51] Int. Cl.$^5$ .................... A61K 31/395; C07D 245/02

[52] U.S. Cl. .................................... 540/460; 540/454; 549/267; 544/127; 544/148; 548/429

[58] Field of Search ................ 540/454, 460; 549/267; 544/127, 148; 548/429

[56] References Cited

U.S. PATENT DOCUMENTS

| | | | |
|---|---|---|---|
| 4,477,440 | 10/1984 | Boger et al. | 424/177 |
| 4,477,441 | 10/1984 | Boger et al. | 424/177 |
| 4,665,052 | 5/1987 | Boger et al. | 514/11 |
| 4,743,584 | 5/1988 | Boger et al. | 514/11 |
| 4,782,043 | 11/1988 | Boger et al. | 514/11 |
| 4,921,855 | 5/1990 | Hemmi et al. | 514/235.8 |

FOREIGN PATENT DOCUMENTS

| | | | |
|---|---|---|---|
| 156318 | 10/1985 | European Pat. Off. | 514/11 |
| 283055 | 9/1988 | European Pat. Off. | 540/454 |
| 365992 | 5/1990 | European Pat. Off. | 514/211 |

OTHER PUBLICATIONS

Sham et al., *Renin Inhibitors. Design and Synthesis of a New Class of Conformationally Restricted Analogues of Angiotensinogen*, J. Med. Chem., 31, 284–295 (1988).

Burger, *Hypotensive Drugs*, Medicinal Chemistry pp. 565–581, 600–601 (1960).

Haber, et al., *Renin Inhibitors: A Search for Principles of Design*, Journal of Cardiovascular Pharmacology 10 (suppl. 7) 857–858 (1987).

Plattner et al., *Renin Hibitors*, J. Med. Chem. 31, pp. 2277–2288 (1988).

Denkewalter et al., Progress in Drug Research, 10, pp. 510–512 (1966).

Bolis et al., Renin Inhibitors, J. Med. Chem., 30, pp. 1729–1737 (1987).

"Feslk et al., *Structural Refinement of a Cyclic Peptide.*", Biochemistry 26, pp. 1851–1859 (1987).

Deber et al., Renin Inhibition, Proceeding of the 9th AM. Peptides Syn. pp. 754–759 (1985).

*Primary Examiner*—Robert T. Bond

*Attorney, Agent, or Firm*—Mark R. Daniel; Joseph F. DiPrima

[57] ABSTRACT

Compounds of the formula

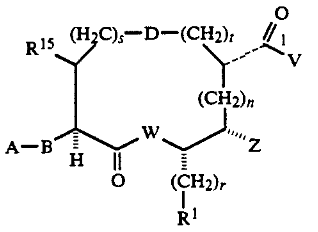

(I)

are disclosed. These compounds inhibit the angiotensinogen-cleaving action of the natural proteolytic enzyme, renin, are useful in treating, preventing or managing renin-associated hypertension, hyperaldosteronism, congestive heart failure, and glaucoma.

4 Claims, No Drawings

CYCLIC RENIN INHIBITORS CONTAINING 2-SUBSTITUTED (3S,4S)-4-AMINO-5-CYCLOHEXYL-3-HYDROXY PENTANOIC ACID, 2-SUBSTITUTED (3S,4S)-5-CYCLOHEXYL-3,4-DI-HYDROXY PENTANOIC ACID OR 2-SUBSTITUTED (4S,5S)-5-AMINO-6-CYCLOHEXYL-4-HYDROXYHEXANOIC ACID OR ITS ANALOGS

CROSS-REFERENCE

This is a continuation-in-part application of U.S. Ser. No. 618,602 filed on Nov. 30, 1990, now abandoned which is a continuation-in-part application of U.S. Ser. No. 559,866 filed on Jul. 27, 1990, now abandoned, which is a continuation-in-part application of U.S. Ser. No. 448,175 filed on Dec. 8, 1989, now abandoned.

BACKGROUND OF THE INVENTION

1. Field of the Invention

The present invention is concerned with novel compounds I which inhibit the angiotensinogen-cleaving action of the natural proteolytic enzyme, renin, with pharmaceutical compositions containing the novel peptides of the present invention as active ingredients, with methods of treating, preventing or managing renin-associated hypertension, hyperaldosteronism, congestive heart failure, and glaucoma with diagnostic methods which utilize the novel compounds I of the present invention, as well as processes therefor. It also includes within its scope methods for treating HIV infections.

Renin is an endopeptidase (molecular weight about 40,000) produced and secreted by the juxtaglomerular cells of the kidney, which cleaves the naturally-occurring plasma glycoprotein, angiotensinogen, specifically at the 10, 11 peptide bond, i.e., between Leu 10 and Leu 11 in the equine substrate, as described by Skeggs et al, *J. Exper. Med.* 1957, 106, 439, or between the Leu 10 and Val 11 in the human renin substrate, as elucidated by Tewksbury et al., *Circulation* 59, 60, Supp. II: 132, Oct. 1979. Renin cleaves angiotensiogen, its protein substrate, to split off the hemodynamically-inactive decapeptide, angiotensin I, which is converted in the lungs, kidney or other tissue by angiotensin-converting enzyme to the potent pressor octapeptide, angiotensin II. Angiotensin II is then believed to cause constriction of the arterioles and to stimulate release of the sodium-retaining hormone, aldosterone, from the adrenal gland and thereby cause a rise in extracellular fluid volume. Thus, the renin-angiotensin system plays an important role in normal cardiovascular homeostasis and in some forms of elevated blood pressure (hypertension).

Inhibitors of angiotensin I converting enzyme have proven useful in the modulation of the renin-angiotensin system. Consequently, specific inhibitors of the limiting enzymatic step that ultimately regulates angiotensin II production, the action of renin on its substrate, have also been sought as effective investigative tools, as well as therapeutic agents in the treatment of hypertension and congestive heart failure.

The compounds of the present invention also exhibit inhibitor activity against HIV protease and are thus useful in the prevention of infection by the human immunodeficiency virus (HIV) and the treatment of consequent pathological conditions such as AIDS. Treating AIDS or preventing infection by HIV is defined as including, but not limited to, treating a wide range of manifestations of HIV infection: AIDS, ARC (AIDS related complex), both symptomatic and asymptomatic, and mere exposure to HIV. For example, the compounds of this invention are useful in preventing infection by HIV after suspected past exposure to HIV by e.g., blood transfusion, accidental needle stick, or exposure to patient blood during surgery.

2. Brief Description of the Prior Art

Several cyclic renin inhibitor designs have been reported in the literature. In general the aim of the studies reported was to use the conformational constraints imposed by the cyclic structures to help define the conformation of substrates and inhibitors as they bind to renin. None of these publications set forth possible advantages for inhibitors of this type or claim or establish any advantage for these cyclic inhibitors over their acyclic counterparts.

Early cyclic inhibitor designs used 18-membered or 20-membered rings to enclose a Pro-Phe beta-turn postulated to occur in bound substrate, and yielded inhibitors with moderate potency, comparable to that of acyclic analogs (C. L. Nakaie, M. C. F. Oliveira, L. Juliano, J. L. Pesquero and A. C. M. Paiva in Peptides, Structure and Function. Proceedings of the Eighth American Peptide Symposium, V. J. Hruby, and D. H. Rich, Eds., Pierce Chemical Co., Rockford, IL., 1983, p. 595; C. R. Nakaie, J. L. Pesquero, M. C. F. Oliveira, L. Juliano and A. C. M. Paiva, in Peptides, Structure and Function. Proceedings of the Ninth American Peptide Symposium, C. M. Deber, V. J. Hruby and K. D. Kopple, Eds., Pierce Chemical Co., Rockford. IL., 1985, p. 755).

Pairs of cysteine side-chains ($P_2$-$P_2'$ and $P_4$-$P_2'$ pairs) have been linked in high molecular weight cyclic inhibitor structures which are based on the $P_1$-$P_1'$ Phe-Phe sequence, statine, or a reduced peptide isostere. Here, $P_2$, $P_2'$, etc., are based on the notation of Schechter and Berger. Only the cyclic inhibitors with a Phe-Phe sequence replacing the scissile bond of substrate show potency comparable to that of acyclic analogs (T. K. Sawyer, D. T. Pals, C. W. Smith, H. S. Saneii, D. E. Epps, D. J. Duchamp, J. B. Hester, R. E. TenBrink, D. J. Staples, A. E. deVaux, J. A. Affholter, G. F. Skala, W. M. Kati, J. A. Lawson, M. R. Schuette, B. V. Kamder and D. E. Emmert in Peptides, Structure and Function. Proceedings of the Ninth American Peptide Symposium, C. M. Deber, V. J. Hruby and K. D. Kopple, Eds., Pierce Chemical Co., Rockford, IL., 1985, p. 729).

Two cyclic inhibitor designs investigated by Boger et al., incorporated disulfides constructed from $P_2$ toward the carboxy terminus, and these had potency comparable to that of an acyclic analog. An amino-terminal cyclic disulfide inhibitor made by connecting $P_5$ and $P_2$ homocysteine sidechains encloses a Pro-Phe beta-turn. The optimal ring size for a $P_5$-$P_2$ cycle is found in the 16-membered ring inhibitor, and three other disulfide cycles with cysteine at either $P_5$ or $P_2$ (or both), were substantially less potent (J. Boger in Aspartic Proteinases and their Inhibitors, V. Kostka, Ed., Walter de Gruyter, Berlin, 1985, p. 401; J. Boger in Proceedings of the Third SCI-RSC Medicinal Chemistry Symposium; Special Publication No. 55 of the Royal Society of Chemistry, R. W. Lambert, Ed., Burlington House, London WlV OBN, 1986, p. 271). Please see also, U.S. Pat. Nos. 4,477,440 and 4,477,441.

Workers at Abbott have reported a series of renin inhibitors in which the $P_1$ side-chain of a "reduced peptide" inhibitor is cyclized onto the alpha-nitrogen atom of alanine at $P_2$ (H. Sham, G. Bolis, H. H. Stein, S. W.

Fesik, P. A. Marcotte, J. J. Plattner, C. A. Rempel and J. Greer, J. Med. Chem., 31, 284 (1988)).

Although in some cases the ring size of the cyclic renin inhibitors cited above is similar to the cyclic renin inhibitors disclosed herein, the inhibitors of the present case are structurally distinct, have lower molecular weight, show high in vitro potency against human renin, and are orally active.

DETAILED DESCRIPTION OF THE INVENTION AND PREFERRED EMBODIMENTS

In accordance with the present invention, there are provided novel compounds of the formula I:

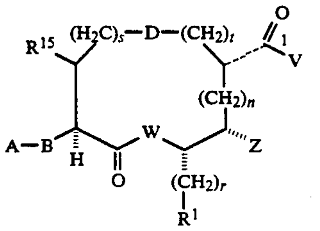

(I)

wherein:

A is hydrogen, Het, where Het is a saturated or unsaturated 5 to 7-membered monocyclic or 7 to 10-membered bicyclic ring which contains at least one and up to two nitrogen atoms(optionally quaternized or in the N-oxide form), where Het may optionally be benzofused, where Het may optionally contain one additional ring atom chosen from among the list consisting of O or S, in sulfide, sulfoxide or sulfone form, where Het may optionally be substituted with one or two Het substituents independently selected from the group consisting of —OH, $C_1$-$C_4$-alkyl, —$CF_3$, —CN, $C_1$-$C_4$-alkoxy, $C_1$-$C_4$-alkoxy-$C_1$-$C_4$-alkoxy, halo, —$NH_2$, mono- or di-($C_1$-$C_4$-alkyl-)amino, —$CO_2H$, —$CO_2$—($C_1$-$C_4$alkyl), —$CONR^{2a}R^{2b}$, —$SO_3H$, $C_1$-$C_4$-alkoxyl-$C_1$-$C_4$-alkoxyl, $C_1$-$C_4$-alkyl-CO—, aryl (where aryl is unsubstituted or mono-, di-, or trisubstituted phenyl or naphthyl wherein the substitutent(s) is/are independently selected from the group consisting of $C_1$-$C_8$-alkyl, amino, phenyl-$C_1$-$C_4$-alkyl, mono- or di-$C_1$-$C_4$-alkyl amino, amino-$C_1$-$C_4$-alkyl, mono- or di-$C_1$-$C_4$-alkylamino-$C_1$-$C_4$-alkyl, guanidyl, guanidyl-$C_1$-$C_4$-alkyl, —OH, $C_1$-$C_4$-alkoxy, —$CONR^{2a}R^{2b}$, —$CO_2H$, —$CO_2$-$C_1$-$C_4$-alkyl, —$CF_3$, halo, $C_1$-$C_4$-alkyl-CO—, $C_1$-$C_4$-alkyl-CONH—, tri-($C_1$-$C_4$-alkyl)$N^+$ $X^-$, where $X^-$ is a counterion selected from the group consisting of single negatively charged ions, such as chloride, bromide, nitrate, perchlorate, benzoate, maleate, benzenesulfonate, methanesulfonate, tartrate, hemitartrate, and acetate) and mono- or disubstituted $C_1$-$C_4$-alkyl (where the substitutent(s) is/are independently selected from the group consisting of —$CO_2H$, —$CO_2$—$C_1$-$C_5$-alkyl, $C_1$-$C_5$-alkyl-CONH—, —OH, —$SO_3H$, $C_1$-$C_4$-alkyl-$SO_2$—, $C_1$-$C_4$-alkyl-SO—, —$SO_2NHCO$—$C_1$-$C_4$-alkyl, $C_1$-$C_5$-alkyl-OCONH— and aryl as defined above), where if one or both N are quaternized in Het, then each nitrogen atom may be quaternized with a Het substituent cited above selected from the group consisting of —$C_1$-$C_4$-alkyl, —$CF_3$, aryl, and mono- or disubstituted $C_1$-$C_4$-alkyl with the corresponding counterion being $X^-$ as defined above, where Het may have in the alternative to the above Het substituents, a Het substituent selected from the group consisting of —$(CH_2)_q$— and —$(CH_2)_2O(CH_2)_2$— which forms a quaternary spirocyclic ring with the N atom wherein q is 3-to-6 and the counterion is $X^-$ as defined above, where Het may be substituted both with one Het substituent chosen from among those listed above and also with up to four Het substituents selected from the group consisting of $C_1$-$C_2$-alkyl substituents (for example where A is 2,2,6,6-tetramethyl-1-benzylpiperidin-4-yl), and Het-$C_1$-$C_4$-alkyl (where Het is as defined above without optional substitution and where the alkyl group is optionally substituted with one or two substituents independently selected from the group consisting of hydroxyl, —$CO_2H$, —$CO_2$—$C_1$-$C_4$-alkyl, —$SO_3H$ and aryl where aryl is as defined above), Aryl-, where aryl is defined above, $R^2CO$— where $R^2$ is unsubstituted or mono- or disubstituted $C_1$-$C_4$-alkyl where the substituent(s) is/are selected from the group consisting of $C_1$-$C_4$-alkyl, —$SO_3H$, aryl or aryl-CO— (where aryl is as defined above), Het or Het—CO— (where Het is as defined above), $R^{2a}O$—, $R^{2a}OCO$—, $R^{2a}R^{2b}N$—, $R^{2a}R^{2b}NCO$—, $R^{2a}R^{2b}NCONH$—, $R^{2a}R^{2b}NSO_2$—, $(R^{2a}O)$ $(R^{2b}O)PO$—, $R^{2c}S$—, $R^{2c}SO$—, $R^{2c}SO_2$—, $R^{2c}CONH$—, $R^{2c}OCONH$—, and —$N(R^{17}R^{18}R^{19})^+$ $X^-$ (where $R^{2a}$ and $R^{2b}$ are independently hydrogen, $C_1$-$C_4$-alkyl, aryl as defined above, Het as defined above, $R^{2c}$ is $C_1$-$C_4$-alkyl, aryl as defined above or Het as defined above, $R^{19}$ is $C_1$-$C_4$-alkyl, $R^{17}$ and $R^{18}$ are independently aryl as defined above, Het as defined above or $C_1$-$C_4$-alkyl optionally substituted with a substituent chosen from the group consisting of aryl as defined above, Het as defined above, —OH, —$NH_2$, —NH—$C_1$-$C_4$-alkyl, —N($C_1$-$C_4$-alkyl$)_2$, —$CO_2H$, —$CO_2$—$C_1$-$C_4$-alkyl, —$SO_3H$, —CO—NH—$SO_2$—$C_1$-$C_4$-alkyl, and —CO—NH—$SO_2$-aryl, and $X^-$ is as defined above), $R^2$— (where $R^2$ is as defined above), $R^2OCO$— (where $R^2$ is as defined above), $R^2SO_2$— (where $R^2$ is as defined above), Aryl-CO— (where aryl is as defined above), Het—CO— (where Het is as defined above), $R^{2a}R^{2b}N$—CO— (where $R^{2a}$ and $R^{2b}$ are as defined above), $R^{2e}(CH_2)_2N(R^{2a})$-CO— (where $R^{2a}$ is as defined above and $R^{2e}$ is het-CO where Het is as defined above or Het $SO_2$—)

$R^{2a}R^{2b\text{-}e}N$—$SO_2$— (where $R^{2a}$ and $R^{2b}$ are as defined above) and $C_1$-$C_4$-alkyl-$(OCH_2CH_2)_xOCO$— (where x is 1 to 3);

B is $CH_2$, —$CH_2$ $CH((CH_2)rR^3)CON(R^{11})$— —$N(A^1)CH[(CH_2)_rR^3]CO$-$N(R^{11})$—, —O-$CH[(CH_2)_rR^3]CO$-$N(R^{11})$—, —$N(A^1)CH[(CH_2)_rR^3$-[CO—O—, —O—$CH[(CH_2)_rR^3]CO$—O— or —$N(A^1)CH[(CH_2)_rR^3[CH(OH)CH_2$—, where r is 0-to-2, $A^1$ is hydrogen or $C_1$-$C_4$-alkyl, $R^3$ is hydrogen, $C_1$-$C_4$-alkyl, ($C_1$-$C_4$-alkyl)O-, ($C_1$-$C_4$-alkyl)S—, $C_2$-$C_4$-alkenyl, aryloxy, arylthio, $C_3$-$C_7$-cycloalkyl, aryl as defined above, Het as defined above or 4-(morpholin-4-yl)ethoxyphenyl, and $R^{11}$ is hydrogen or $C_1$–$C_4$-alkyl;

A and B together may alternatively be: G-$CH_2CH[(CH_2)_rR^3]$-Q-$N(R^{11})$-, G-$CH_2CH[(CH_2)_rR^3]CO$-O-, Het-S(O)-$_m$—$CH[(CH_2)_rR^3]CON(R^{11})$—, (where r, $R^3$, $R^{11}$ and Het are as defined above and Q is —CO— or —$SO_2$—), $R^{2d}CON(R^{11})$—, $R^{2d}OCON(R^{11})$—, $R^{2d}CO$-O-, $R^{2d}SO_2N(R^{11})$—, (where $R^{2d}$ is Het as defined above, aryl as defined above, or $C_1$–$C_4$-alkyl or $C_2$–$C_4$-alkenyl substituted with Het, Het-O, aryl, or aryl-O-, each as defined above),

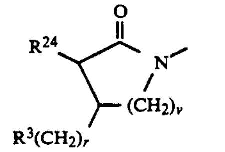

or

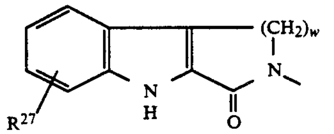

(where v is 1-to-3, w is 1 or 2, $R^{27}$ is $C_1$–$C_4$-alkyl, amino, mono- or di-$C_1$–$C_4$-alkylamino, —OH, $C_1$–$C_4$-alkoxy, —$CO_2H$, —$CO_2$—$C_1$–$C_4$-alkyl, —$CONR^{2a}R^{2b}$, —$CF_3$, halo, —NHCO—O—$C_1$–$C_4$-alkyl, —$N(C_1$–$C_4$-alkyl)CO—O—$C_1$–$C_4$-alkyl, —NH-CO—$C_1$–$C_4$-alkyl or —$N(C_1$–$C_4$-alkyl)CO—$C_1$–$C_4$-alkyl, $R^3$ and r are as defined above, $R^{24}$ is hydrogen, $C_1$–$C_4$-alkyl or is A-N(H)- where A is independently selected from the definition of A as defined above);

G is $R^{20}$—$S(O)_m$— (where m is 0-to 2 and $R^{20}$ is $C_3$–$C_7$-cycloalkyl, aryl as defined above, Het as defined above or $C_1$–$C_4$-alkyl optionally substituted with one or two substituents chosen from the group consisting of $C_1$–$C_4$-alkoxy, —OH, —$CO_2H$, —$CO_2$—$C_1$–$C_4$-alkyl, —$NH_2$, —$NH(C_1$–$C_4$-alkyl), —$N(C_1$–$C_4$-alkyl$)_2$ and ($C_1$–$C_4$-alkyl)CO—O—), $R^{17}R^{18}NSO_2$— (where $R^{17}$ and $R^{18}$ are as defined above), $R^{2e}(CH_2)_r$—$N(R^{2a})$—$SO_2$ where r, $R^{2a}$, and $R^{2e}$ are as defined above 1 or $R^{2e}(CH_2)r$—$N(R^{2a})$ —CO— where, r, $R^{2a}$, and $R^{2e}$ are as defined above; $R^{20}CO$- (where $R^{20}$ is as defined above), $R^{20}OCO$— (where $R^{20}$ is as defined above) or —$CH(OH)CH_2$Het (where Het is defined above);

A and B together may be —J—$CH[(CH_2)_r$—$R^3]$—K—;

K is
—$CH_2$—,
—CH(OH)—,
—CO—,
—NH—,
—O—,
—S—,
—SO—,
—$SO_2$—,
—NO—,
—P(O)O—;

J is $R^{28}$—CO—$(CH_2)_d$ (where d is 0-to-4, $R^{28}$ is —OH, —O—$C_1$–$C_6$-alkyl, —$NR^{18}R^{18}$, Het) $R^{29}$ —$SO_2$— (where $R^{29}$ is —$C_1$–$C_4$-alkyl, aryl, Het), $R^{30}$ (where $R^{30}$ is aryl, Het, $C_1$–$C_4$-alkyl optionally substituted with aryl, Het, —$CO_2H$, —$CO_2$—$C_1$–$C_4$-alkyl, —$SO_2$—$C_1$–$C_4$-alkyl, —$SO_2$Ar, —$SO_2$Het), $R^{30}$—N-H—CO— where $R^{30}$ is as defined above;

$R^1$ is $C_1$–$C_4$-alkyl, aryl as defined above, unsubstituted, di-, or trisubstituted $C_3$–$C_7$-cycloalkyl (where the substituents is/are selected from the group consisting of $C_1$–$C_4$-alkyl, trifluoromethyl, —OH, $C_1$–$C_4$-alkoxy, or halo) or a 5- or 6-membered ring unsaturated heterocycle containing one or two heteroatoms selected from the group consisting of N, O or S, optionally substituted with one or two substituents (where the substituents is/are selected from the group consisting of $C_1$–$C_4$-alkyl, $C_1$–$C_4$-alkoxy, halo, —$NH_2$ or —OH);

$R^{15}$ is $C_1$–$C_4$-alkyl, aryl as defined above, imidazol-4-yl, thiazol-4-yl or thiazol-5-yl;

D is a single bond or is
—$N(R^{25})$CO—,
—$CON(R^{25})$—,
—NH—CO—NH—,
—NH—$SO_2$—NH—,
—$SO_2$—NH—,
—NH—$SO_2$—,
—CO—O—,
—O—CO—,
—O—CO—NH—,
—SO—,
—$SO_2$—,
—O—,
—S—,
—NH—CO—O,
—CH=CH—,
—CO—, or
—CH(OH)—, (where $R^{25}$ is —H or $C_1$–$C_4$-alkyl and the asymmetrical groups are inserted into formula I clockwise from left to right);

n is 0-to-1;
s is 0-to-1;
t is 1-to-4;

Z is —$NH_2$, —OH, —$OPO_3H_2$, —$OCOR^{22}$, —O-CO—$OR^{22}$ (where $R^{22}$ is 5-indanyl or $C_1$–$C_6$-alkyl optionally substituted with Ph, —$SO_3H$, —$CO_2H$, —$PO_3H_2$, —$NH_2$, —$NH(C_1$–$C_4$-alkyl), —$N(C_1$–$C_4$-alkyl$)_2$, —$N(C_1$–$C_4$-alkyl$)_3^+X^-$ where $X^-$ is defined above), —$OCHR^{22a}$—$OCOR^{22b}$ (where $R^{22a}$ and $R^{22b}$ are $C_1$–$C_4$-alkyl),

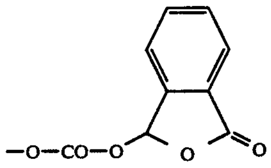

or —$OCOCH_2(OCH_2CH_2)_x$—O—$C_1$–$C_4$-alkyl or —O—CO—O—$(CH_2CH_2O)_x$-$C_1$–$C_4$-alkyl (where x is defined above);

W is —$NR^{23}$— (where $R^{23}$ is —H or $C_1$–$C_4$-alkyl) or —O—;

V is: —Y—$(CH_2)_x$-$[CH(R^5)]_y$—$(CH_2)_z$—$R^{10}$
where Y=O, NH, N—$C_1$–$C_4$-alkyl, or is absent; x is 0-to-1, y is 0-to-1, z is 0-to-4,
$R^5$ is H, $C_1$–$C_4$ alkyl, $C_3$–$C_7$ cycloalkyl, aryl as defined above or Het as defined above, and
$R^{10}$ is hydrogen, —OH, aryl as defined above, Het as defined above, —$NH_2$, —$NR^{17}R^{18}$, —$NHR^{18}$, —$N(R^{17}R^{18}R^{19})^+$ $X^-$, (where $R^{17}$, $R^{18}$, $R^{19}$ and X− are as defined above), $-S(O)_m-R^{26}$ (where m is 0-to-2 and $R^{26}$ is Het as defined above, aryl as defined above, or $C_1$-$C_4$-alkyl optionally substituted with a substituent chosen from among the group consisting of aryl as defined above, Het as defined above, $-NH_2$, —OH, —NH—$C_1$-$C_4$-alkyl, and $-N(C_1$-$C_4$-alkyl$)_2$), $-SO_2NH_2$, $-SO_2NR^{17}R^{18}$ (where $R^{17}$ and $R^{18}$ are as defined above), $-SO_2NHR^{18}$ (where $R^{18}$ is as defined above),

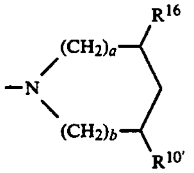

(where a=1 to 2, b=0 to 1, $R^{16}$=—H, —OH, $C_1$-$C_4$-alkyl, aryl, arylthio or aryloxy where aryl is defined above, and $R^{10'}$ is $R^{10}$ as defined above absent the cyclic moieties containing $R^{10'}$),

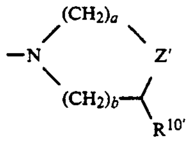

(where a, b and $R^{10'}$ are as defined above; and Z' is O, S, SO, $SO_2$, or NH),

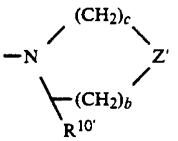

(where b, $R^{10}$, and Z' are as defined above, and c is 2 to 3), and

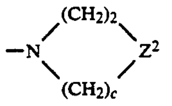

(where c is as defined above and $Z^2$ is $NR^{18}$ or $N(R^{17}R^{18})^+$ X−, where $R^{17}$, $R^{18}$ and X− are as defined above).

Heterocyclic substituents in which nitrogen is the heteroatom are preferred, and of these, those containing a single nitrogen atom are preferred. Fully saturated heterocyclic substituents are also preferred. Thus, piperidine is a preferred heterocyclic substituent. Other preferred heterocyclic substituents are: quinuclidinyl, pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

The term "halo" means fluoro, chloro, bromo and iodo. Among substituents for A, B, $R^1$, $R^{11}$ $R^{15}$, V and Z, preferred groups are recognized as follows.

Preferred A are:

Boc—, EtOC—, —i-$PrSO_2$—, $CH_3(OCH_2CH_2)_3OCO$—,

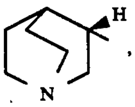, 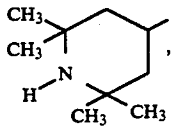, 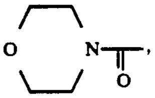

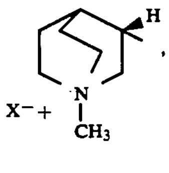, 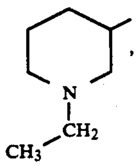

t-Bu—$Ch_2$—CO—NH—$(CH_2)_2OCO$—

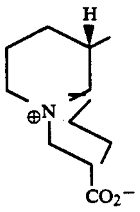

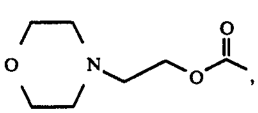, 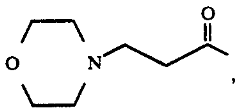,

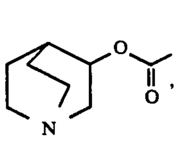, 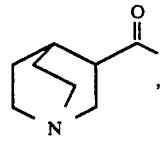,

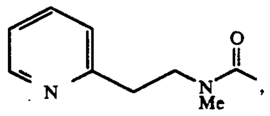,

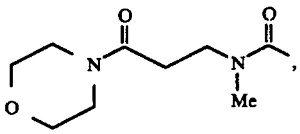,

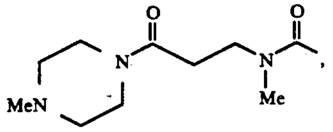,

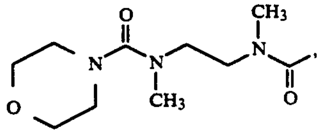

-continued
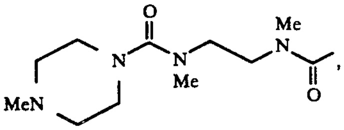 , or 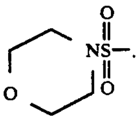
Preferred B are:
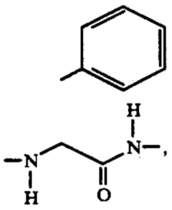 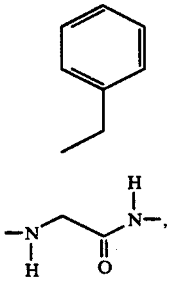
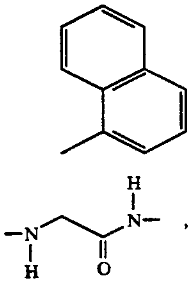 , 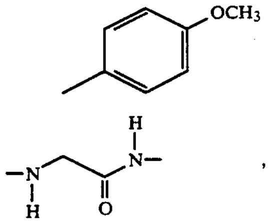 ,
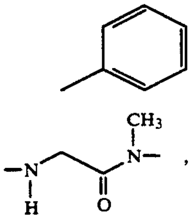 , 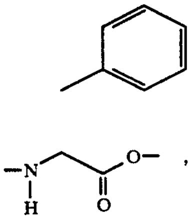 ,
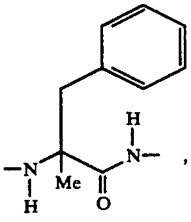 , 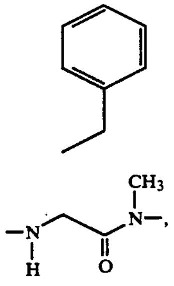
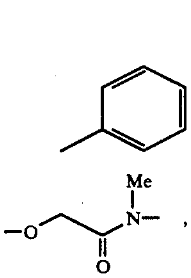 , 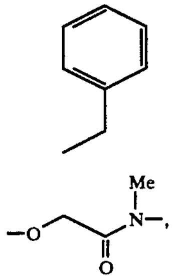
-continued
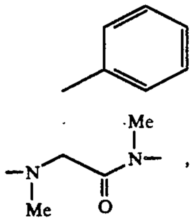 , 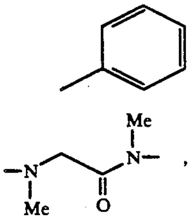 ,
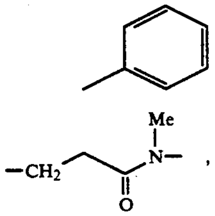 , 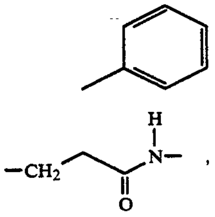 ,
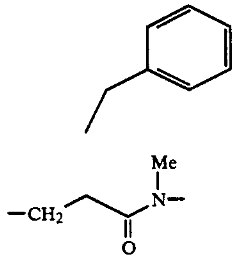 or 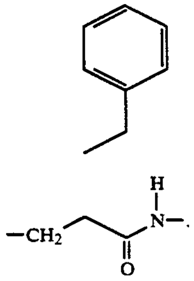
Preferred A and B taken together are:
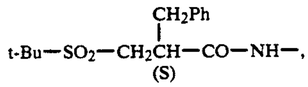
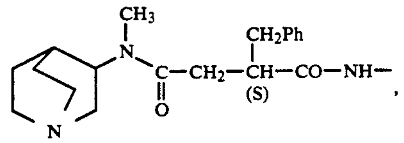 ,
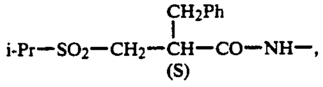
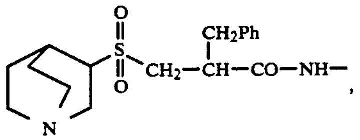 ,
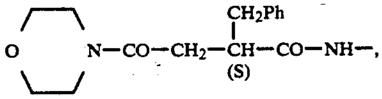
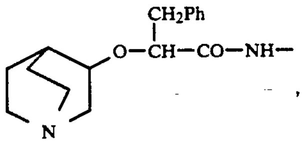 , -continued
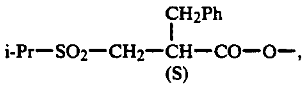
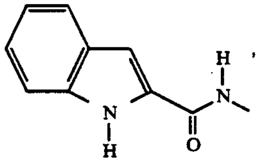
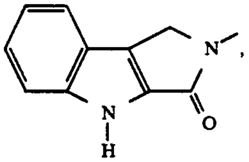
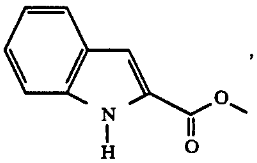
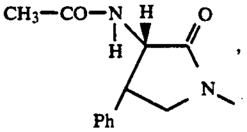
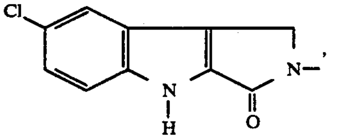
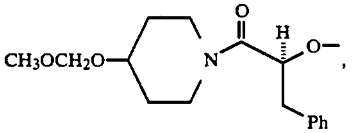
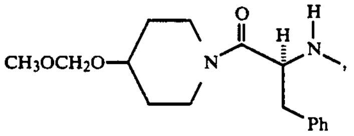
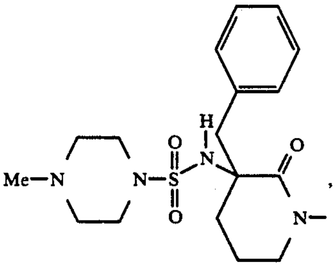
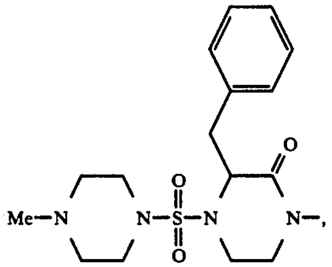
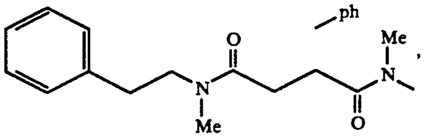
-continued
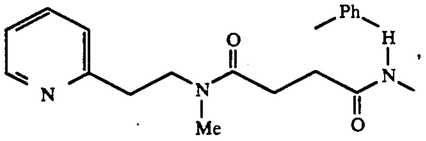
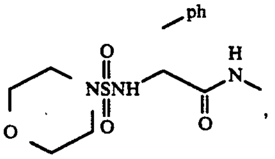
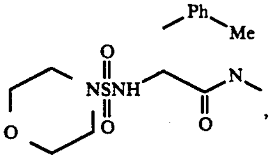
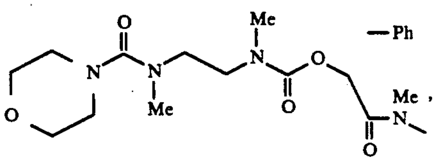
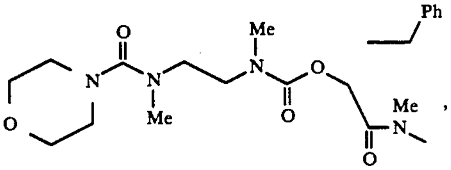
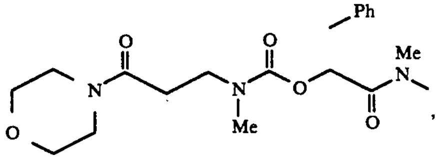
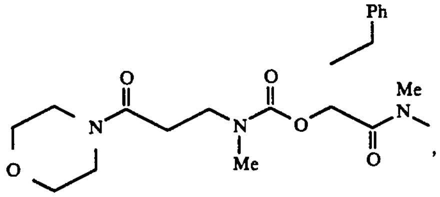
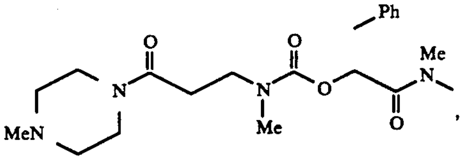
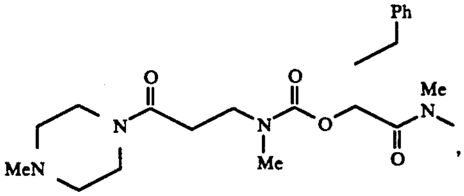
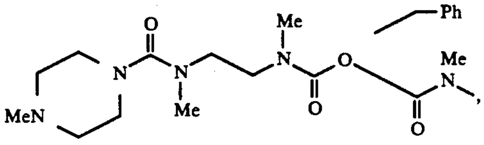

-continued

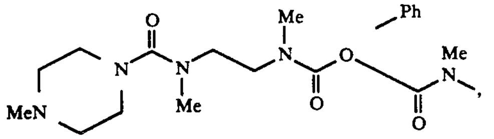

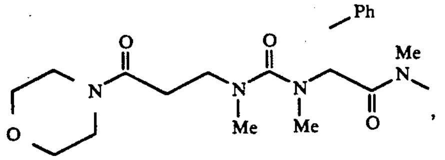

, or

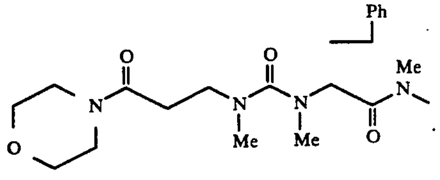

Preferred V are:

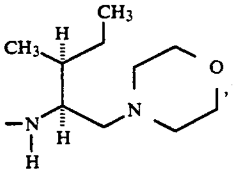

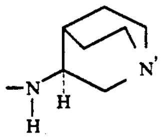

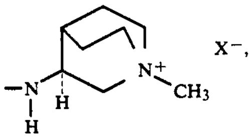

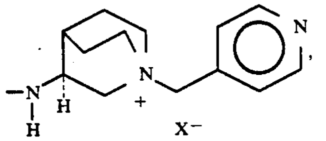

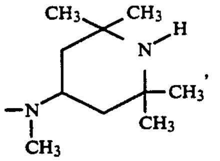

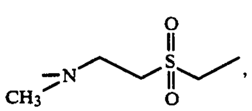

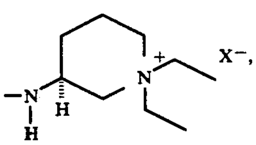

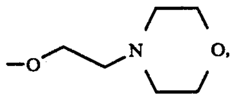

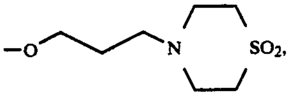

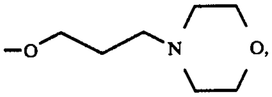

-continued

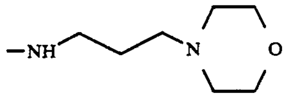

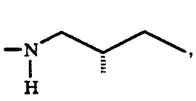

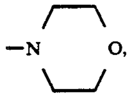

$-OCH_3$,

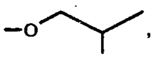

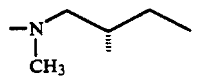

and

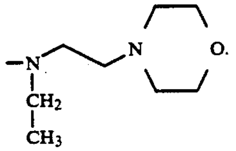

Preferred $R^{15}$ are —H and —$CH_3$, a preferred $R^1$ is cyclohexyl, preferred $R^{11}$ is H or —$CH_3$ and preferred Z are —OH, —$OCOCH_2CH_2CO_2H$, —$OCOCH_2N$($C_1$-$C_4$-alkyl)$_2$, —OCO—$CH_2NH_2$, —O-$COCH_2CH_2NH_2$, —OCO($C_1$-$C_4$-alkly), —$NH_2$, —O-COCH(n-Bu)$NH_2$, —OCOCH(i-Pr)$NH_2$, —OCO-O$(CH_2CH_2O)_3CH_3$ —$OPO_3H_2$ and —$OCOCH_2CH_2PO_3H_2$.

Among the preferred compounds having the preferred substituents for A, B, V, $R^1$, $R^{11}$, $R^{15}$ and Z as defined in the foregoing paragraphs are those of the formula II. (Herein, all substituents are read into their respective generic structures clockwise from left to right).

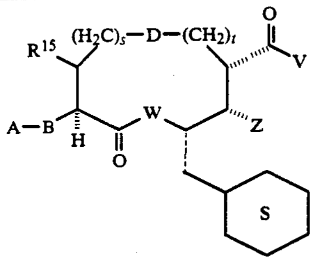

(II)

in which s, D, W and t are:

| s | D | W | t |
|---|---|---|---|
| 1 | —CONH— | —NH— | 4 |
| 1 | —CONH— | —NH— | 3 |
| 1 | —CO—O— | —NH— | 4 |
| 1 | —CO—O— | —NH— | 3 |
| 0 | —NH—CO— | —NH— | 5 |
| 0 | —NHCONH— | —NH— | 4 |
| 1 | —$SO_2$NH— | —NH— | 4 |
| 1 | —$SO_2$NH— | —NH— | 3 |
| 0 | —OCO— | —NH— | 4 |
| 0 | —OCO— | —NH— | 5 |
| 1 | —CONH— | —O— | 4 |
| 1 | —CONH— | —O— | 3 |
| 1 | —COO— | —O— | 4 |
| 1 | —COO— | —O— | 3 |
| 0 | —OCO— | —O— | 4 |
| 0 | —OCO— | —O— | 5 |
| 0 | —S— | —NH— | 5 |
| 0 | —S— | —NH— | 6 |
| 0 | —S— | —O— | 5 |

-continued
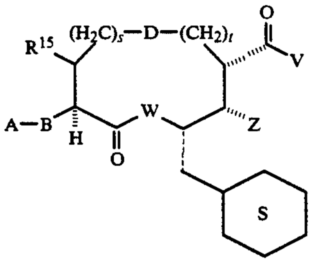
(II)
in which s, D, W and t are:
| s | D | W | t |
|---|---|---|---|
| | | | |
|---|---|---|---|
| 0 | —S— | —O— | 6 |
The preferred compounds of the present invention include those in Tables 1-19:
TABLE 1
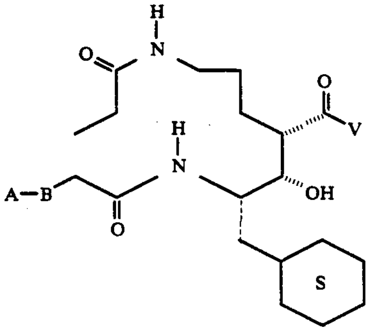
| Number | A—B | V |
|---|---|---|
| 11-1 | Boc—Phe—NH— | —NH-2(S)-methylbutyl |
| 11-2 | Boc—Phe—NH— | —OEt |
| 11-3 | Boc—Phe—NH— | —O-isobutyl |
| 11-4 | 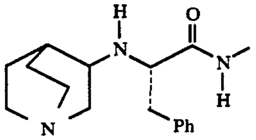 | 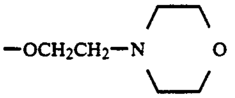 |
| 11-5 | Boc—Phe—NH— | 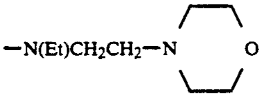 |
| 11-6 | 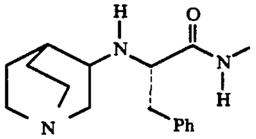 | —O-isobutyl |
| 11-7 | 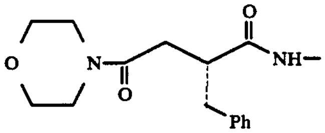 | 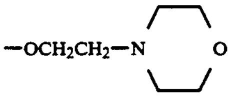 |
| 11-8 | 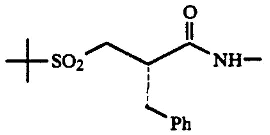 | —O-i-Pr |
| 11-9 | 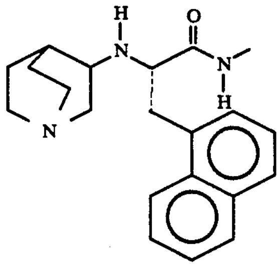 | —O-i-Pr |

TABLE 1-continued
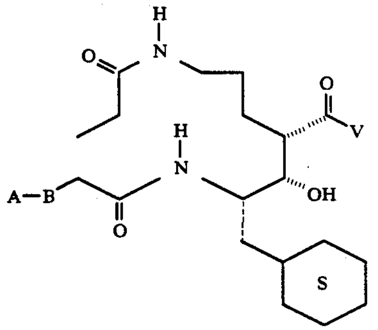
| Number | A—B | V |
|---|---|---|
| 11-10 | 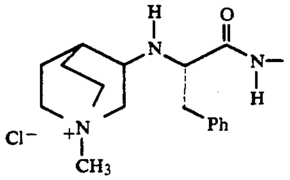 | —O-i-Pr |
| 11-11 | 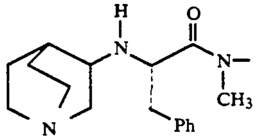 | —O-i-Pr |
| 11-12 | 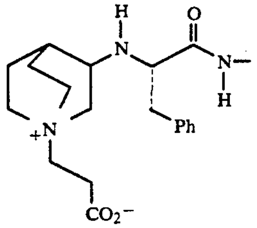 | —O-i-Pr |
| 11-13 | 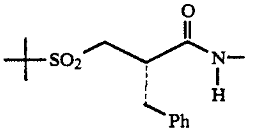 | 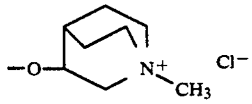 |
| 11-14 | 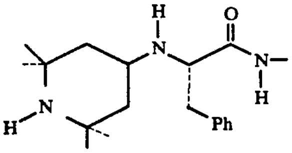 | —O-i-Pr |
| 11-15 | 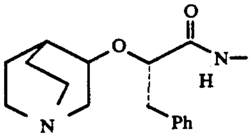 | —O-i-Pr |
| 11-16 | 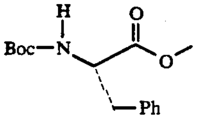 | —O-i-Pr |

TABLE 1-continued
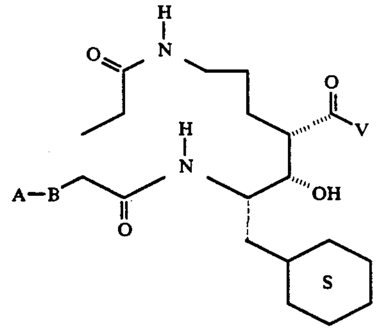
| Number | A—B | V |
|---|---|---|
| 11-17 | 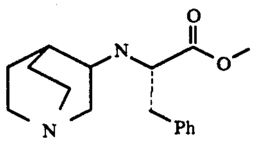 | 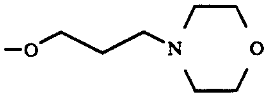 |
| 11-18 | 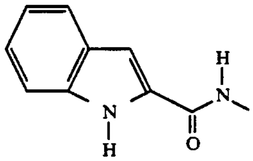 | 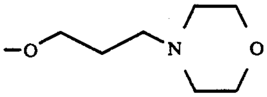 |
| 11-19 | 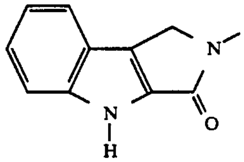 | 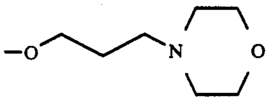 |
| 11-20 | 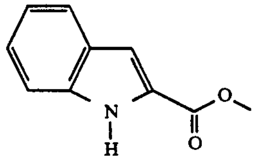 | 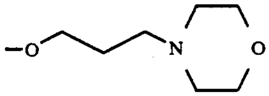 |
| 11-21 | 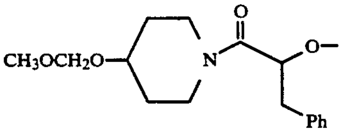 | 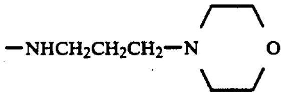 |
| 11-22 | 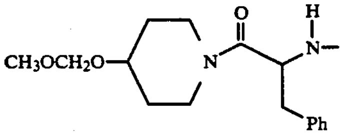 | 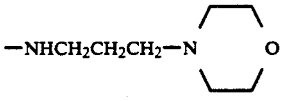 |

TABLE 2
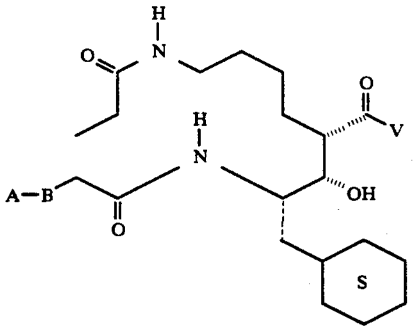
| Number | A—B | V |
| --- | --- | --- |
| 18-1 | Boc—Phe—NH— | —$OCH_3$ |
| 18-2 | Boc—Phe—NH— | —NH-2(S)-methylbutyl |
| 18-3 | 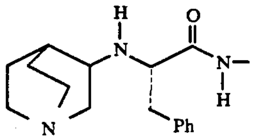 | —O-i-Pr |
| 18-4 | 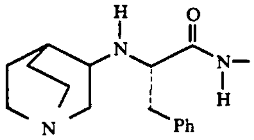 | 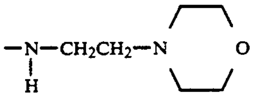 |
| 18-5 | 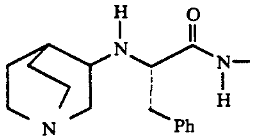 | 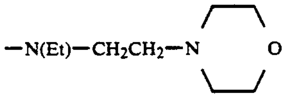 |
| 18-6 | 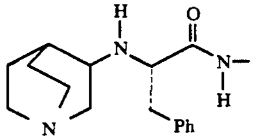 | 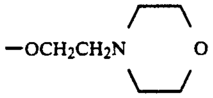 |
| 18-7 | 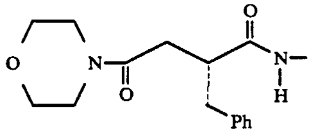 | —O-i-Pr |
| 18-8 | 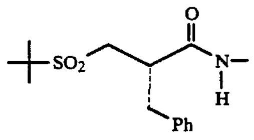 | —O-i-Bu |
| 18-9 | 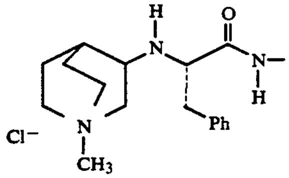 | —O-i-Pr |
| 18-10 | 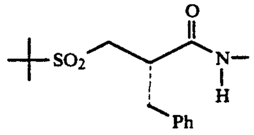 | 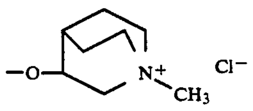 |

TABLE 2-continued
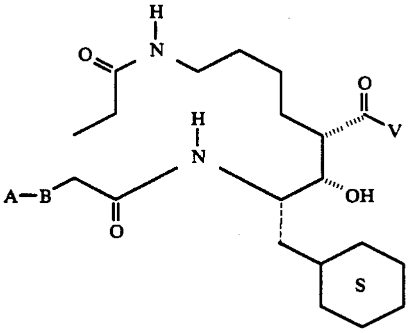
| Number | A—B | V |
|---|---|---|
| 18-11 | 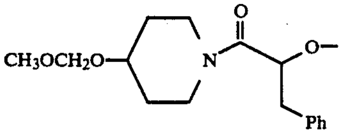 | 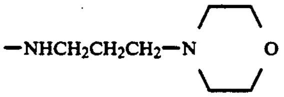 |
| 18-12 | 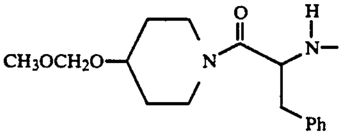 | 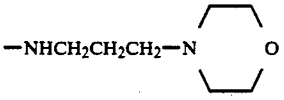 |
TABLE 3
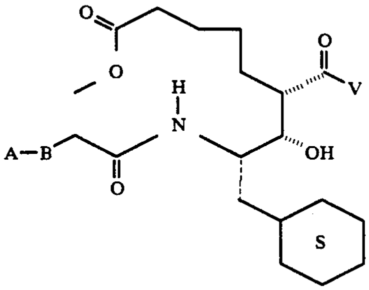
| Number | A—B | V |
|---|---|---|
| 25-1 | Boc—Phe—NH | —O-i-Pr |
| 25-2 | Boc—Phe—NH | —NH-2(S)-methylbutyl |
| 25-3 | Cbz—NH— | —O-i-Bu |
| 25-4 | 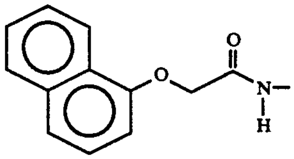 | —O-i-Pr |
| 25-5 | 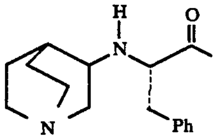 | —O-i-Pr |
| 25-6 | 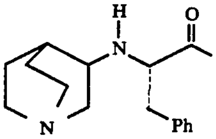 | 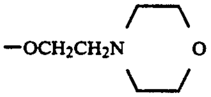 |

TABLE 3-continued
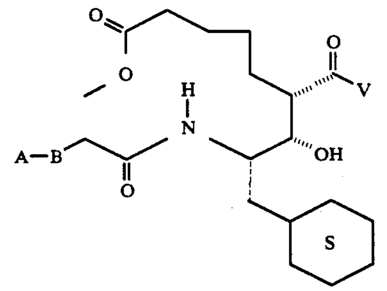
| Number | A—B | V |
| --- | --- | --- |
| 25-7 | 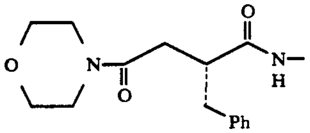 | 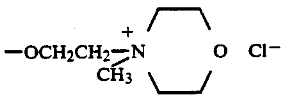 |
| 25-8 | 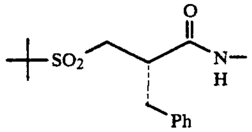 | 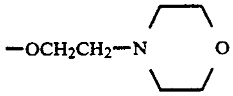 |
| 25-9 | 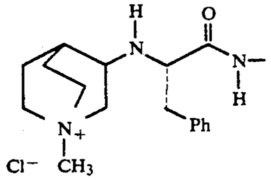 | —O-i-Pr |
| 25-10 | 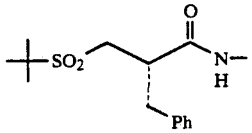 | 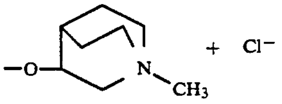 |
| 25-11 | 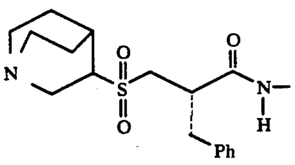 | 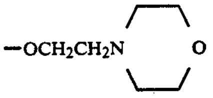 |
| 25-12 | 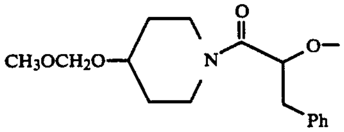 | 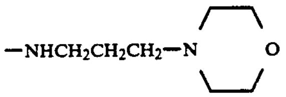 |
| 25-13 | 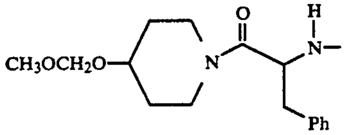 | 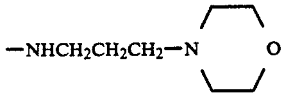 |

TABLE 4
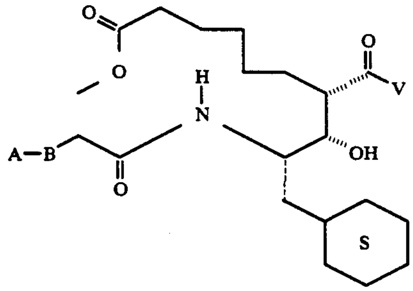
| Number | A—B | V |
|---|---|---|
| 42 | Boc—Phe—NH— | —OEt |
| 43 | Boc—Phe—NH— | —NH-2(S)-methylbutyl |
| 44 | Cbz | —OCH2CH2N 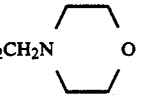 |
| 45 | 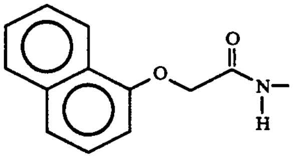 | —O-i-Pr |
| 46 | 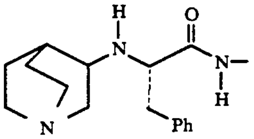 | —O-i-Pr |
| 47 | 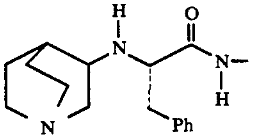 | —OCH2CH2—N 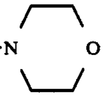 |
| 48 | 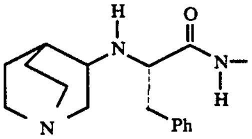 | —OCH2Ph |
| 49 | 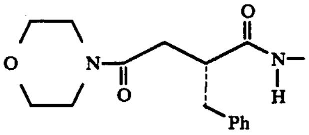 | —OCH2CH2—N 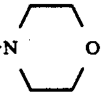 |
| 50 | 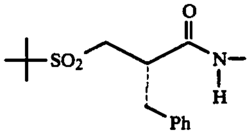 | —O-i-Pr |
| 51 | 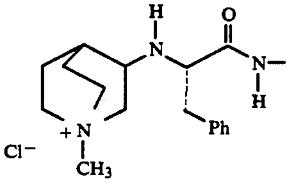 | —O-i-Pr |

TABLE 4-continued
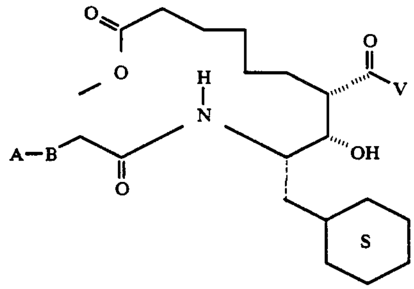
| Number | A—B | V |
|---|---|---|
| 52 | 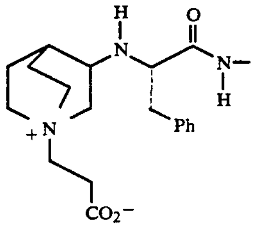 | —O-i-Pr |
| 53 | 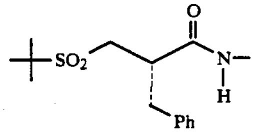 | 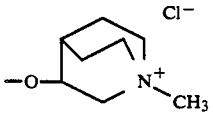 |
| 54 | 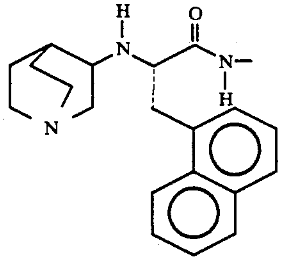 | 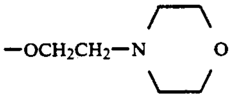 |
| 54A | 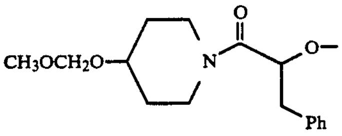 | 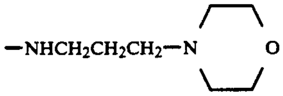 |
| 54B | 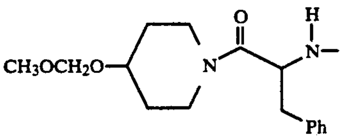 | 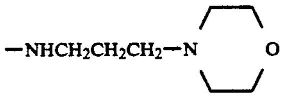 |

TABLE 5
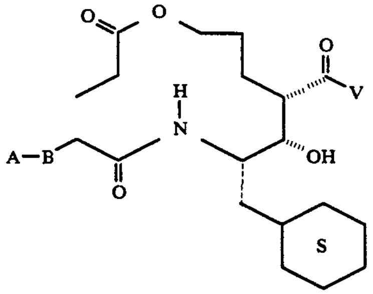
| Number | A—B | V |
|---|---|---|
| 55 | Boc—Phe—NH— | —OEt |
| 56 | Boc—Phe—NH— | —NH-2(S)-methylbutyl |
| 57 | Cbz | —OCH2CH2N 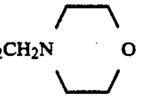 |
| 58 | 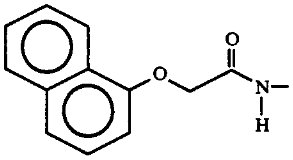 | —O-i-Pr |
| 59 | 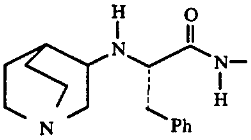 | —O-i-Pr |
| 60 | 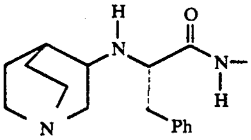 | —OCH2CH2—N 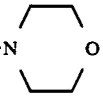 |
| 61 | 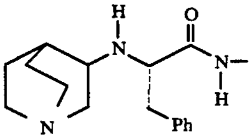 | —OCH2Ph |
| 62 | 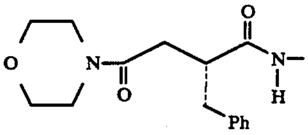 | —OCH2CH2N 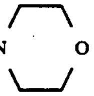 |
| 63 | 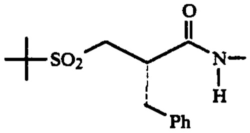 | —O-i-Pr |
| 64 | 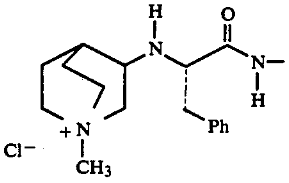 | —O-i-Pr |

TABLE 5-continued
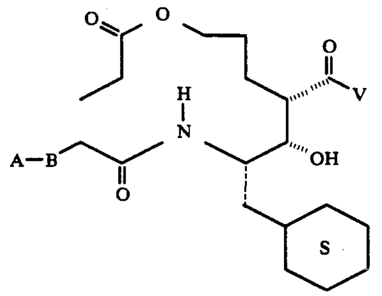
| Number | A—B | V |
|---|---|---|
| 65 | 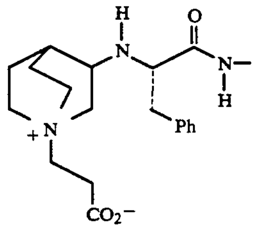 | —O-i-Pr |
| 66 | 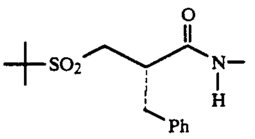 | 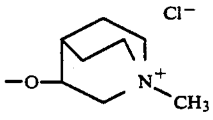 |
| 67 | 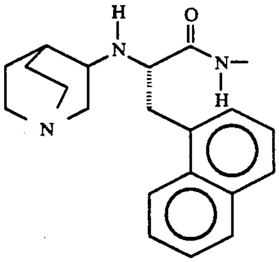 | 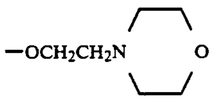 |
| 67A | 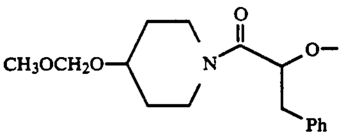 | 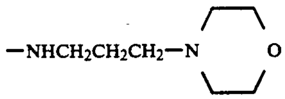 |
| 67B | 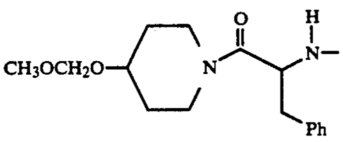 | 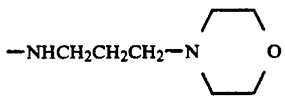 |

TABLE 6
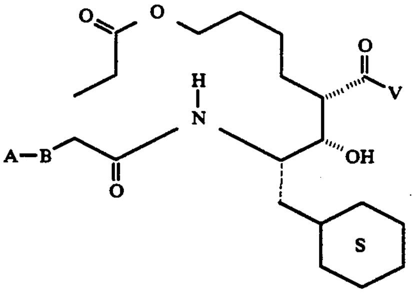
| Number | A—B | V |
|---|---|---|
| 68 | Boc—Phe—NH— | $—OCH_3$ |
| 69 | Boc—Phe—NH— | —OEt |
| 70 | 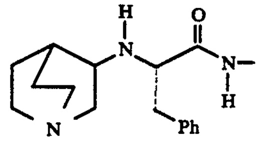 | —O-i-Pr |
| 71 | 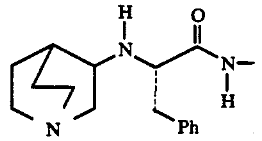 | 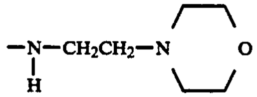 |
| 72 | 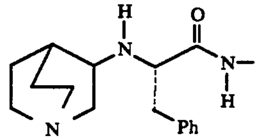 | 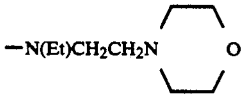 |
| 73 | 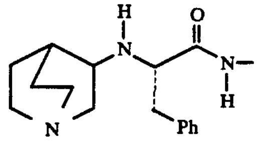 | 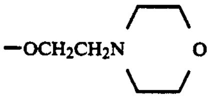 |
| 74 | 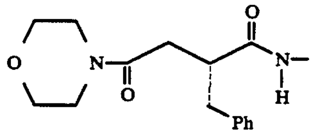 | —O-i-Pr |
| 75 | 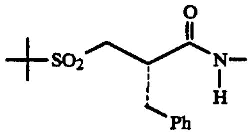 | —O-i-Bu |
| 76 | 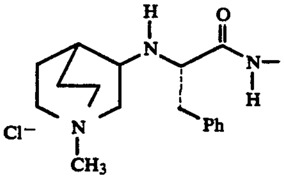 | —O-i-Pr |
| 77 | 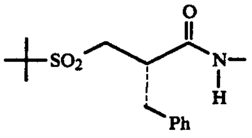 | 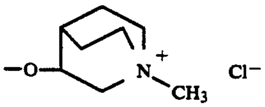 |

TABLE 6-continued
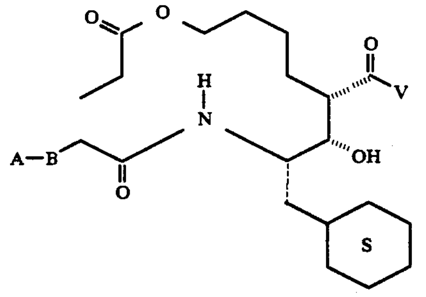
| Number | A—B | V |
|---|---|---|
| 77A | 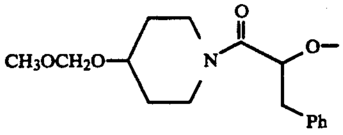 | 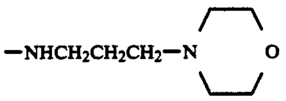 |
| 77B | 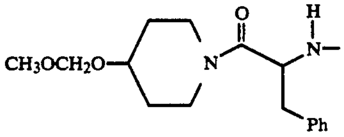 | 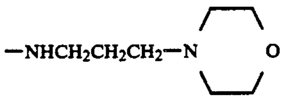 |
TABLE 7
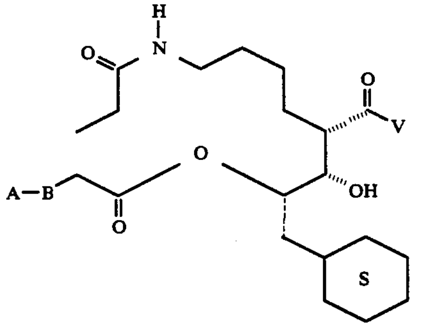
| Number | A—B | V |
|---|---|---|
| 87 | Ac—Phe—NH— | $-OCH_3$ |
| 93 | Boc—Phe—N(H)— | —N(H)-n-butyl |
| 94 | Ac—Phe—NH— | —OEt |
| 95 | 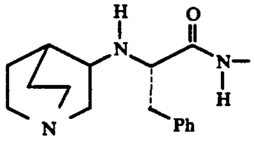 | —O-i-Pr |
| 96 | 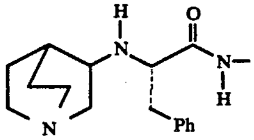 | 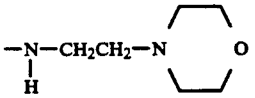 |
| 97 | 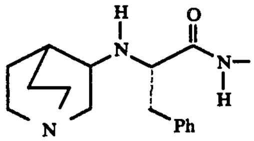 | 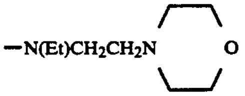 |

TABLE 7-continued
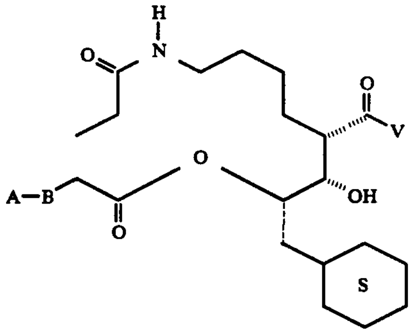
| Number | A—B | V |
|---|---|---|
| 98 | 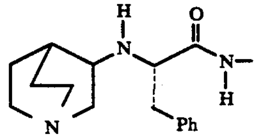 | 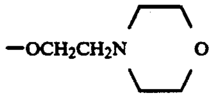 |
| 99 | 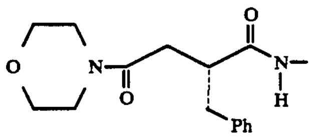 | —O-i-Pr |
| 100 | 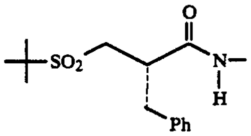 | —O-i-Bu |
| 101 | 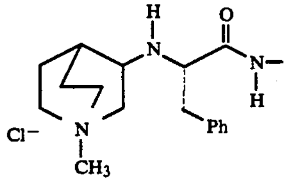 | —O-i-Pr |
| 102 | 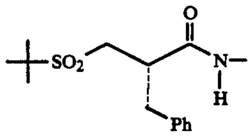 | 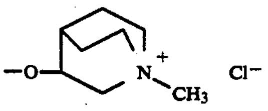 |
| 102A | 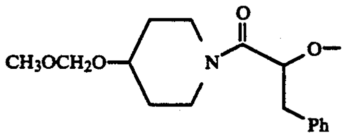 | 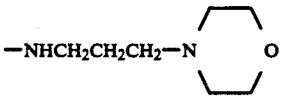 |
| 102B | 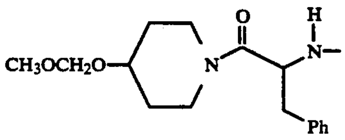 | 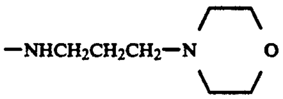 |

TABLE 8
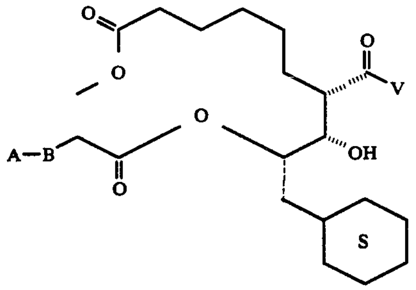
| Number | A—B | V |
|---|---|---|
| 109 | Ac—Phe—NH— | —O-i-butyl |
| 114 | Boc—Phe—NH— | —N-n-butyl<br>H |
| 115 | Cbz | 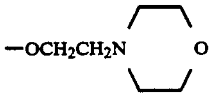 |
| 116 | 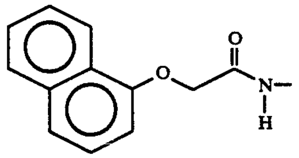 | —O-i-Pr |
| 117 | 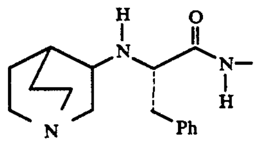 | —O-i-Pr |
| 118 | 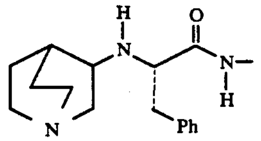 | 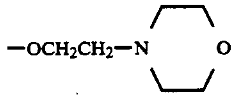 |
| 119 | 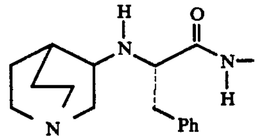 | $-OCH_2Ph$ |
| 120 | 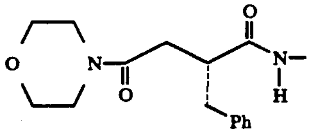 | 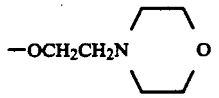 |
| 121 | 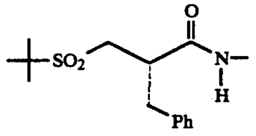 | —O-i-Pr |
| 122 | 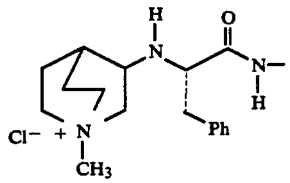 | —O-i-Pr |

TABLE 8-continued
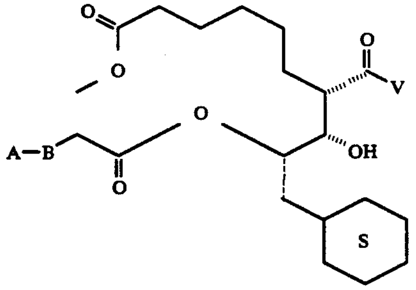
| Number | A—B | V |
|---|---|---|
| 123 | 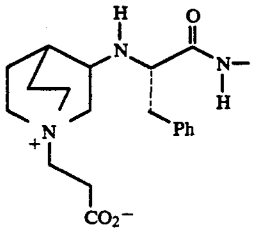 | —O-i-Pr |
| 124 | 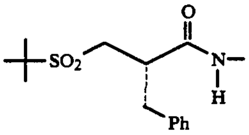 | 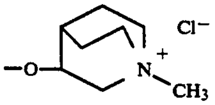 |
| 125 | 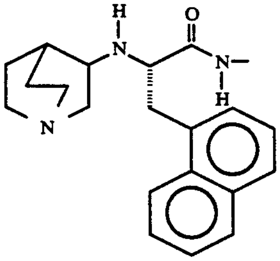 | 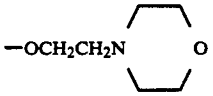 |
| 125A | 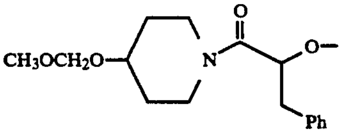 | 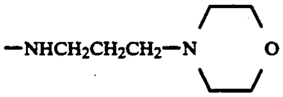 |
| 125B | 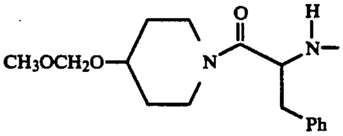 | 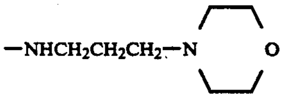 |

TABLE 9
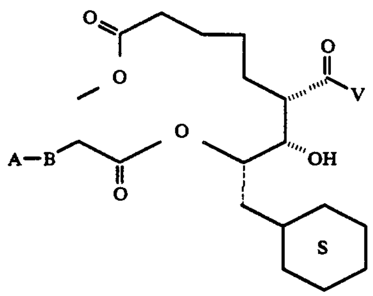
| Number | A—B | V |
|---|---|---|
| 126 | Boc—Phe—NH | —O-i-Pr |
| 127 | Boc—Phe—NH | —NH-2(S)-methylbutyl |
| 128 | Cbz—NH— | —O-i-Bu |
| 129 | 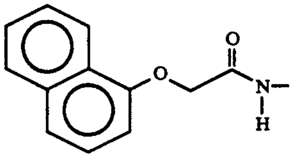 | —O-i-Pr |
| 130 | 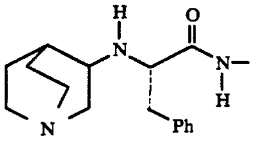 | —O-i-Pr |
| 131 | 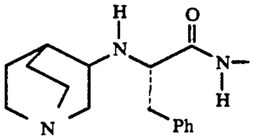 | 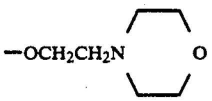 |
| 132 | 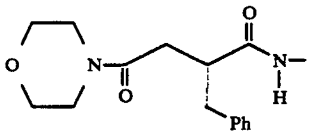 | 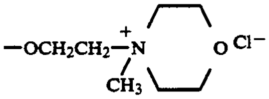 |
| 133 | 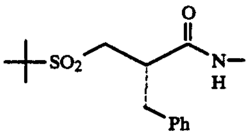 | 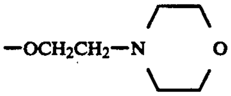 |
| 134 | 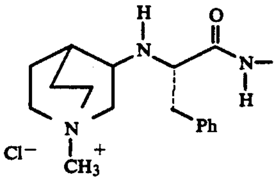 | —O-i-Pr |
| 135 | 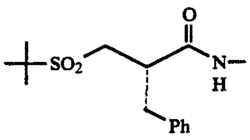 | 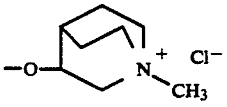 |

TABLE 9-continued
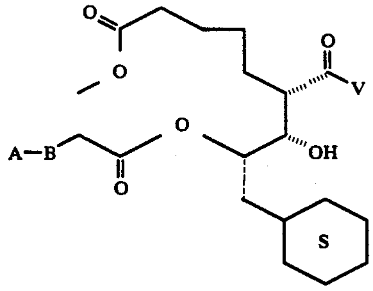
| Number | A—B | V |
|---|---|---|
| 136 | 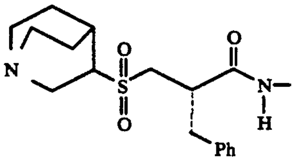 | 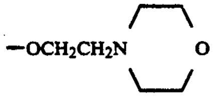 |
| 137 | 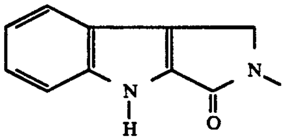 | —O-i-Pr |
| 137A | 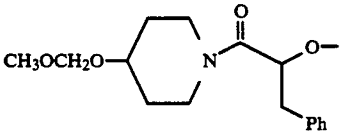 | 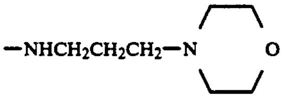 |
| 137B | 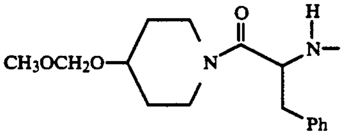 | 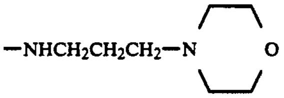 |
TABLE 10
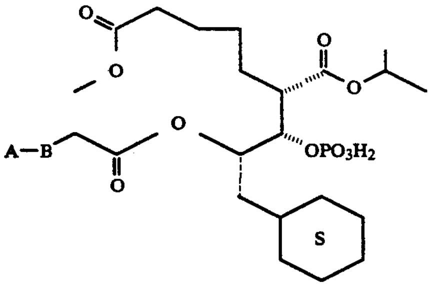
| Number | A—B |
|---|---|
| 175 | 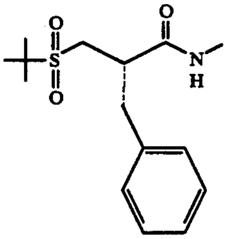 |
TABLE 10-continued
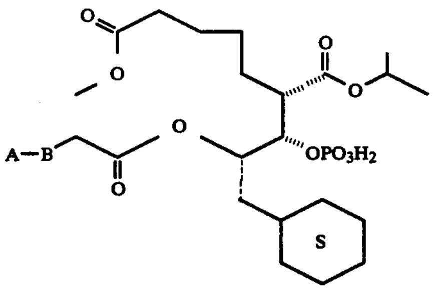
| Number | A—B |
|---|---|
| 176 | 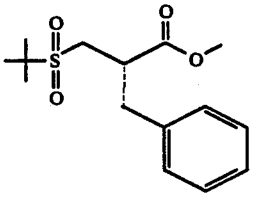 |

TABLE 10-continued
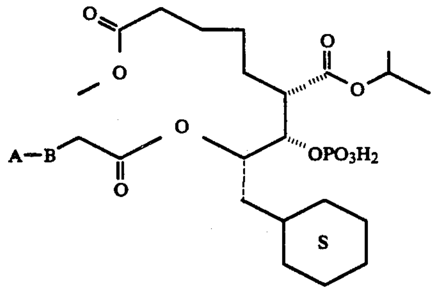
| Number | A—B |
|---|---|
| 177 | 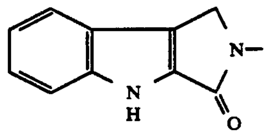 |
| 178 | 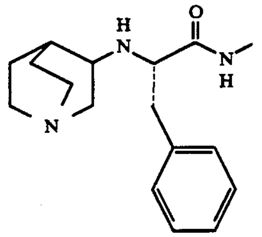 |
| 179 | 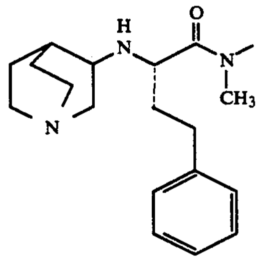 |
TABLE 11
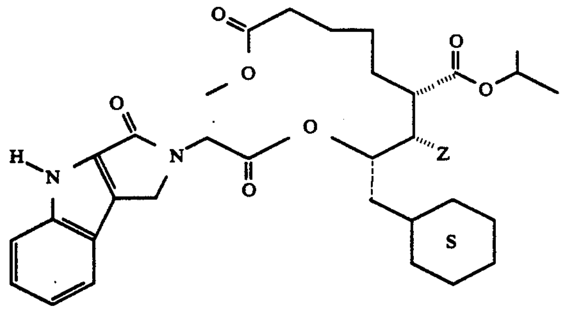
| NUMBER | Z |
|---|---|
| 180 | $-OCOCH_3$ |
| 181 | $-OCOCH_2CH_2CO_2H$ |
| 182 | 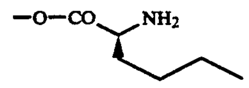 |
| 183 | $-OCOCH_2CH_2NH_2$ |
| 184 | $-O-COO-(CH_2CH_2O)_3CH_3$ |
| 185 | $-OCOCH_2CH_2N(CH_3)_3{}^{+}Cl^{-}$ |
TABLE 12
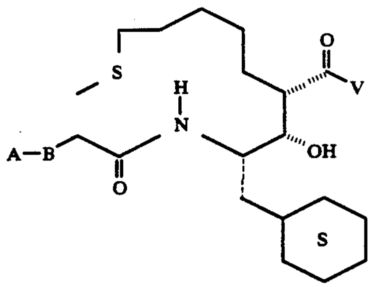
| Number | A—B | V |
|---|---|---|
| 186 | Boc—Phe—NH— | $-OCH_3$ |
| 187 | Boc—Phe—NH— | —OEt |
| 188 | 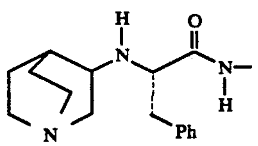 | —O-i-Pr |

TABLE 12-continued
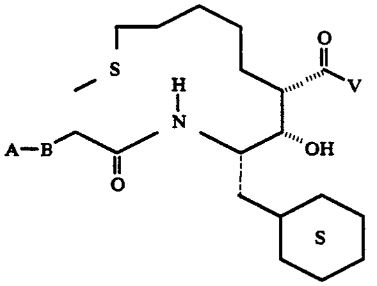
| Number | A—B | V |
|---|---|---|
| 189 | 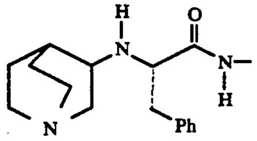 | 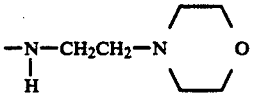 |
| 190 | 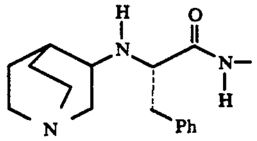 | 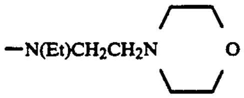 |
| 191 | 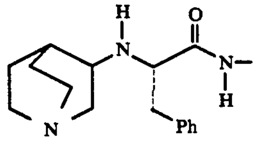 | 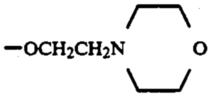 |
| 192 | 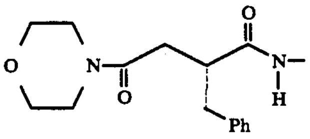 | —O-i-Pr |
| 193 | 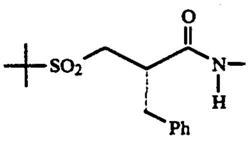 | —O-i-Bu |
| 194 | 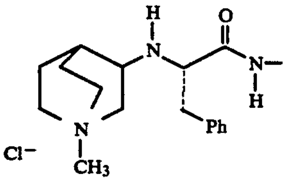 | —O-i-Pr |
| 195 | 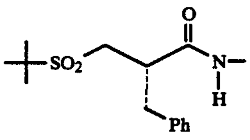 | 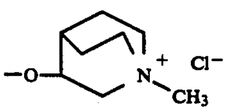 |
| 196 | 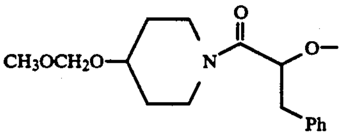 | 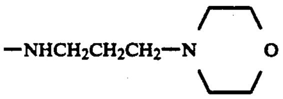 |

TABLE 12-continued
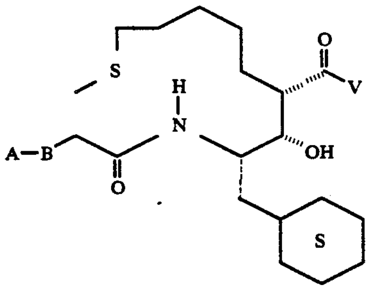
| Number | A—B | V |
|---|---|---|
| 197 | 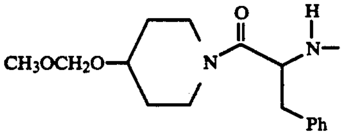 | 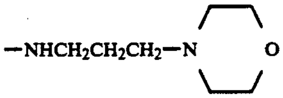 |
TABLE 13
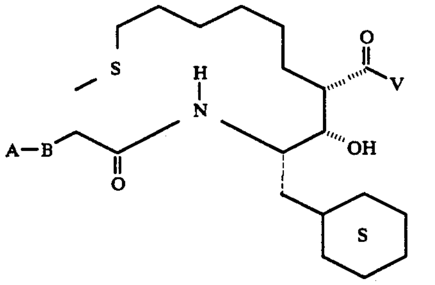
| Number | A—B | V |
|---|---|---|
| 198 | Boc—Phe—NH— | —$OCH_3$ |
| 199 | Boc—Phe—NH— | —OEt |
| 200 | 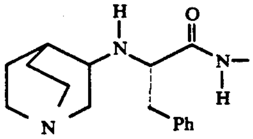 | —O-i-Pr |
| 201 | 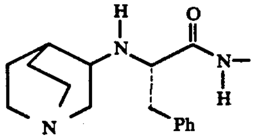 | 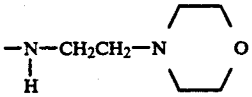 |
| 202 | 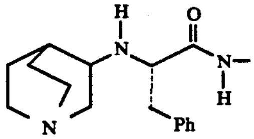 | 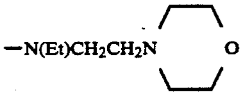 |
| 203 | 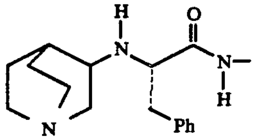 | 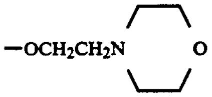 |

TABLE 13-continued
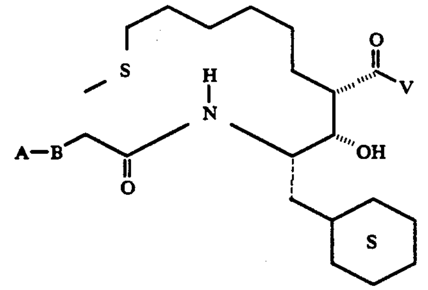
| Number | A—B | V |
|---|---|---|
| 204 | 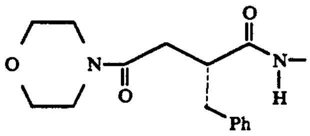 | —O-i-Pr |
| 205 | 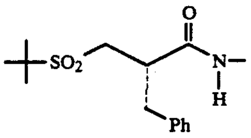 | —O-i-Bu |
| 206 | 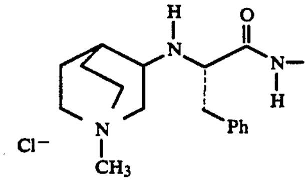 | —O-i-Pr |
| 207 | 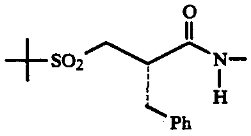 | 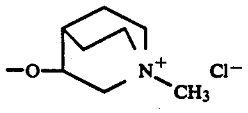 |
| 208 | 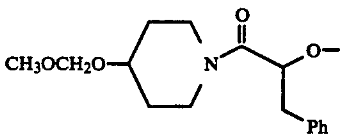 | 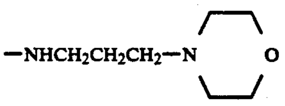 |
| 209 | 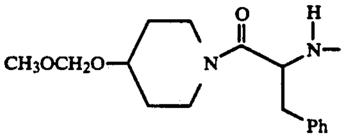 | 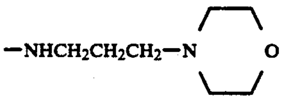 |

TABLE 14
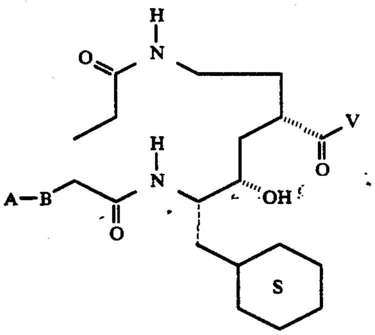
| Number | A—B | V |
|---|---|---|
| 210 | Boc—Phe—NH— | —NH-2(S)-methylbutyl |
| 211 | Boc—Phe—NH— | —OEt |
| 212 | Boc—Phe—NH— | —O-isobutyl |
| 213 | 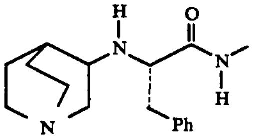 | 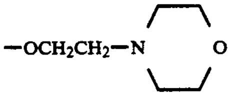 |
| 214 | Boc—Phe—NH— | 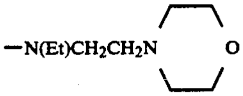 |
| 215 | 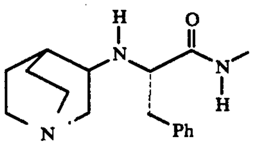 | —O-isobutyl |
| 216 | 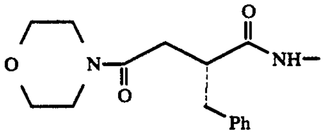 | 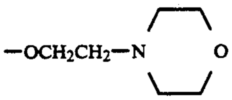 |
| 217 | 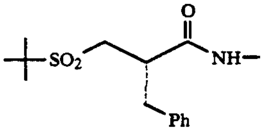 | —O-i-Pr |
| 219 | 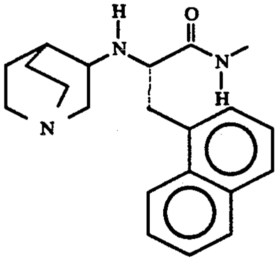 | —O-i-Pr |
| 219 | 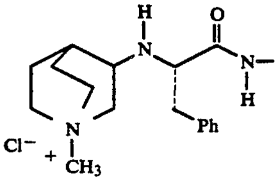 | —O-i-Pr |

TABLE 14-continued
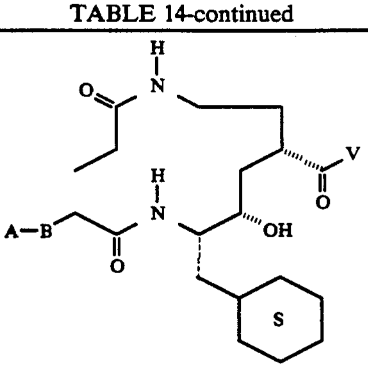
| Number | A—B | V |
|---|---|---|
| 220 | 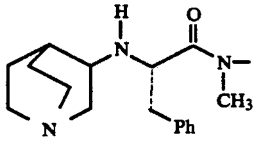 | —O-i-Pr |
| 221 | 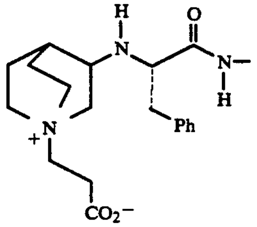 | —O-i-Pr |
| 222 | 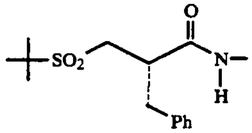 | 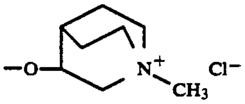 |
| 223 | 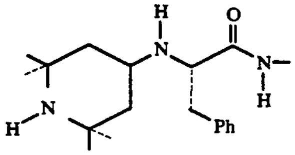 | —O-i-Pr |
| 224 | 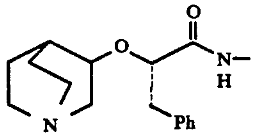 | —O-i-Pr |
| 225 | 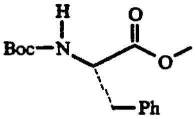 | —O-i-Pr |
| 226 | 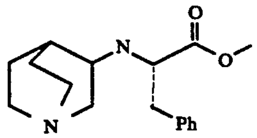 | 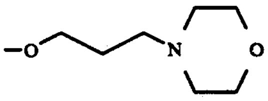 |
| 227 | 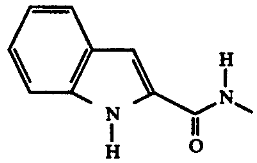 | 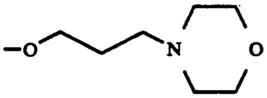 |

TABLE 14-continued
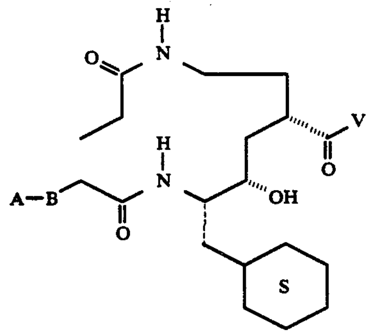
| Number | A—B | V |
|---|---|---|
| 228 | 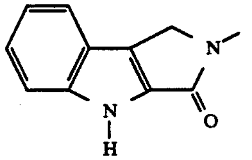 | 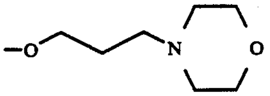 |
| 229 | 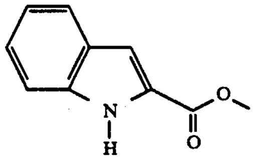 | 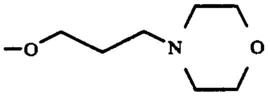 |
| 230 | 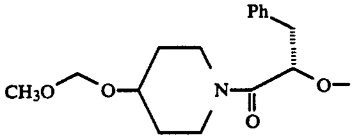 | 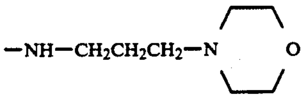 |
| 231 | 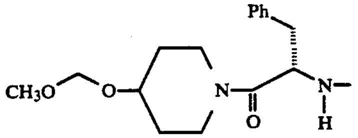 | 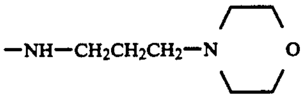 |
TABLE 15
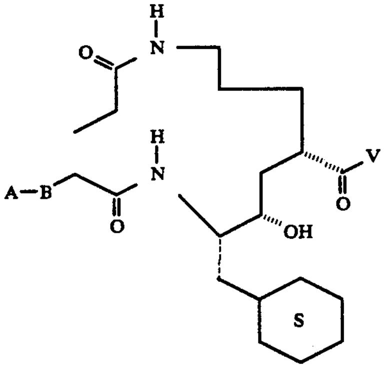
| Number | A—B | V |
|---|---|---|
| 232 | Boc—Phe—NH— | $-OCH_3$ |
| 233 | Boc—Phe—NH— | —NH-2(S)-methylbutyl |

TABLE 15-continued
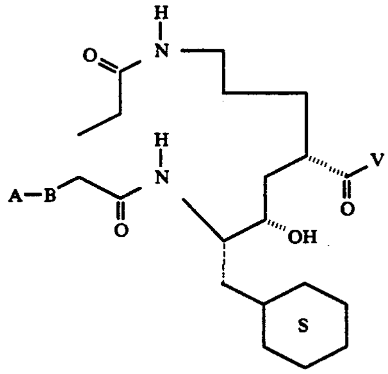
| Number | A—B | V |
|---|---|---|
| 234 | 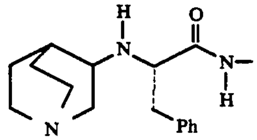 | —O-i-Pr |
| 235 | 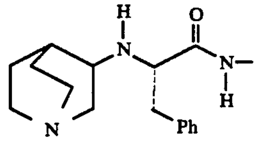 | 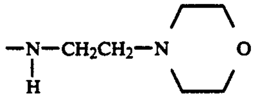 |
| 236 | 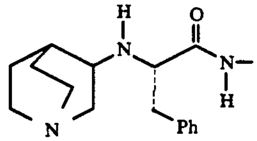 | 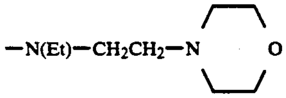 |
| 237 | 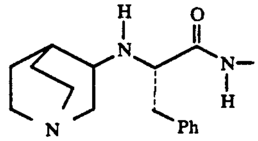 | 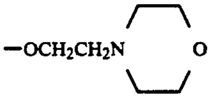 |
| 238 | 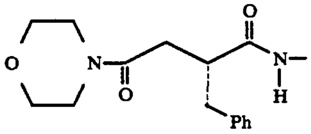 | —O-i-Pr |
| 239 | 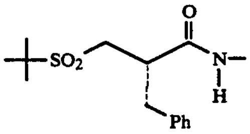 | —O-i-Bu |
| 240 | 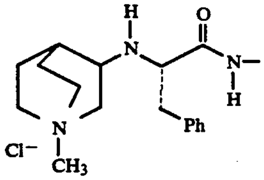 | —O-i-Pr |
| 241 | 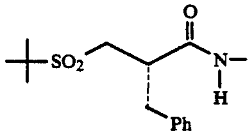 | 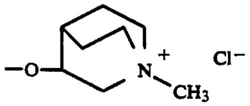 |

TABLE 15-continued
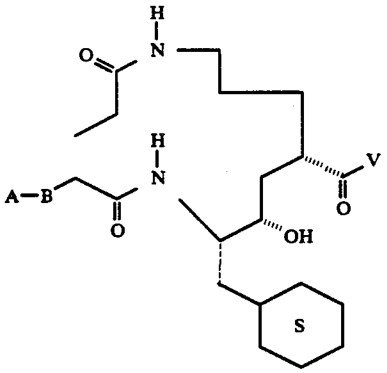
| Number | A—B | V |
|---|---|---|
| 242 | 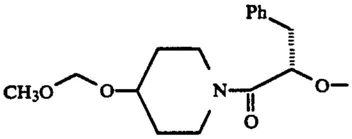 | 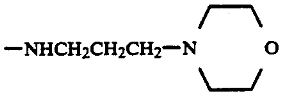 |
| 243 | 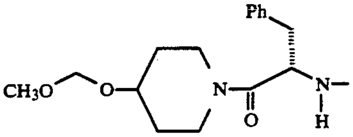 | 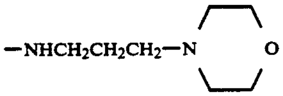 |
TABLE 16
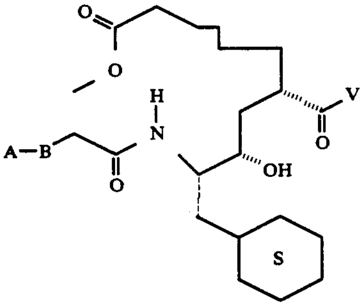
| Number | A—B | V |
|---|---|---|
| 244 | Boc—Phe—NH | —O-i-Pr |
| 245 | Boc—Phe—NH | —NH-2(S)-methylbutyl |
| 246 | Cbz—NH— | —O-i-Bu |
| 247 | 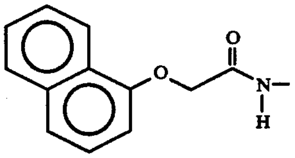 | —O-i-Pr |
| 248 | 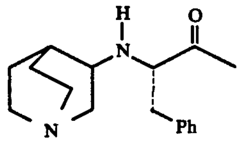 | —O-i-Pr |
| 249 | 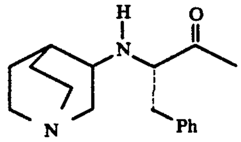 | 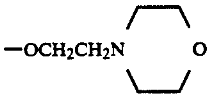 |

TABLE 16-continued
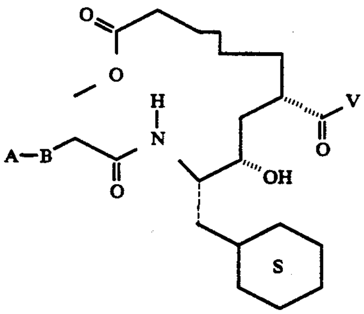
| Number | A—B | V |
|---|---|---|
| 250 | 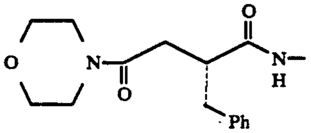 | 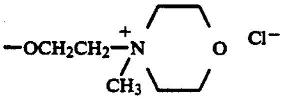 |
| 251 | 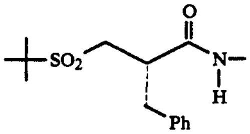 | 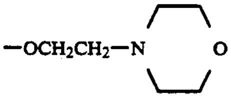 |
| 252 | 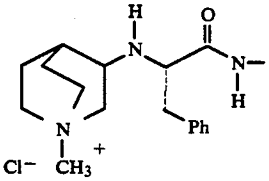 | —O-i-Pr |
| 253 | 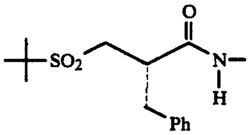 | 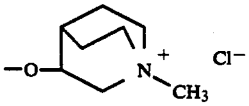 |
| 254 | 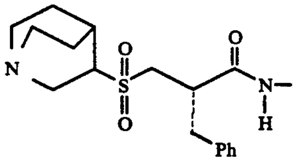 | 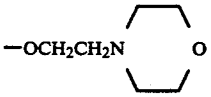 |
| 255 | 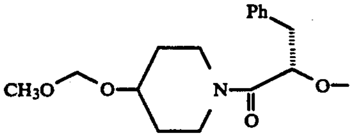 | 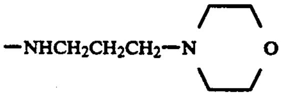 |
| 256 | 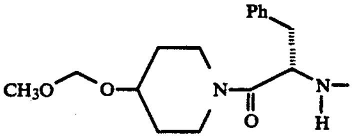 | 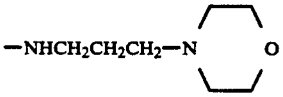 |

TABLE 17
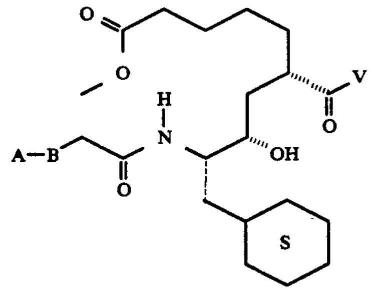
| Number | A—B | V |
|---|---|---|
| 257 | Boc—Phe—NH— | —OEt |
| 258 | Boc—Phe—NH— | —NH-2(S)-methylbutyl |
| 259 | Cbz | 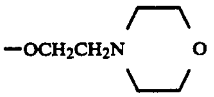 |
| 260 | 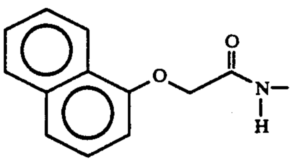 | —O-i-Pr |
| 261 | 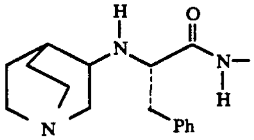 | —O-i-Pr |
| 262 | 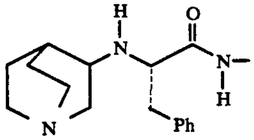 | 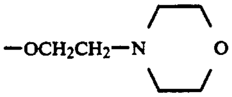 |
| 263 | 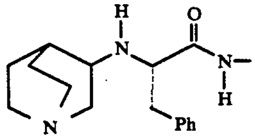 | —OCH$_2$Ph |
| 162 | Boc—Phe—NH— | 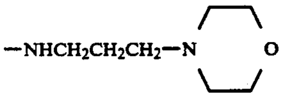 |
| 264 | 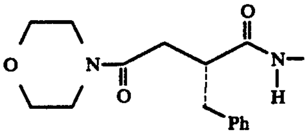 | 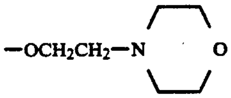 |
| 265 | 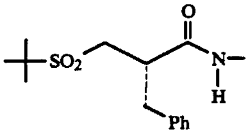 | —O-i-Pr |

TABLE 17-continued
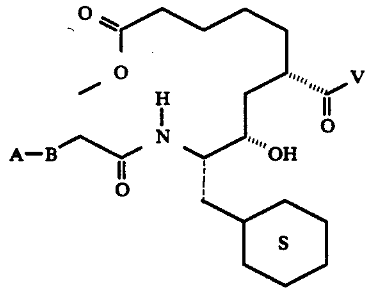
| Number | A—B | V |
|---|---|---|
| 266 | 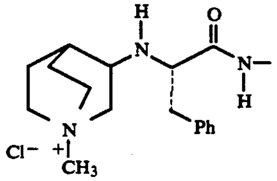 | —O-i-Pr |
| 267 | 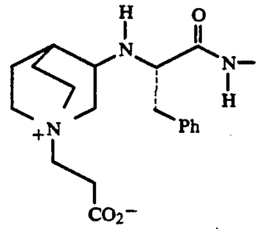 | —O-i-Pr |
| 268 | 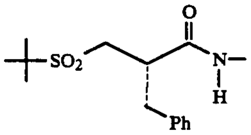 | 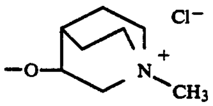 |
| 269 | 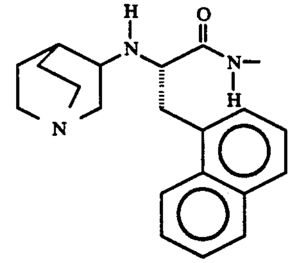 | 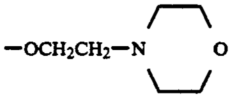 |
| 168 | 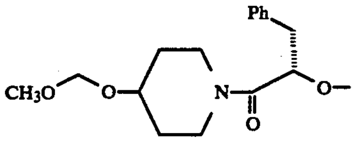 | 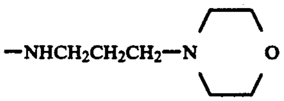 |
| 169 | 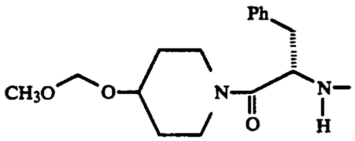 | 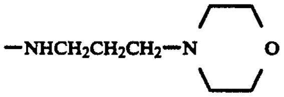 |

TABLE 18
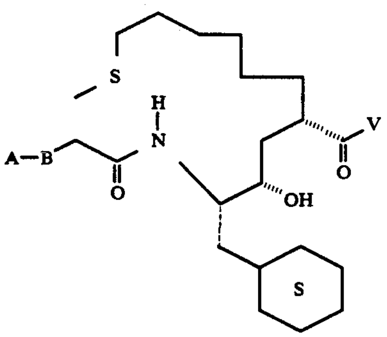
| Number | A—B | V |
|---|---|---|
| 270 | Ac—Phe—NH— | —O-i-butyl |
| 271 | Boc—Phe—NH— | $-\underset{H}{N}$-n-butyl |
| 272 | Cbz | 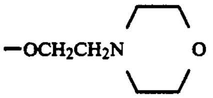 |
| 273 | 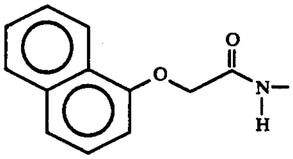 | —O-i-Pr |
| 274 | 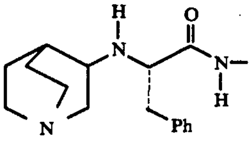 | —O-i-Pr |
| 275 | 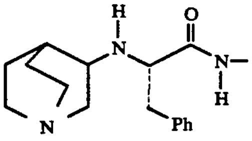 | 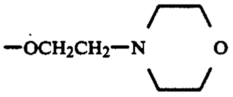 |
| 276 | 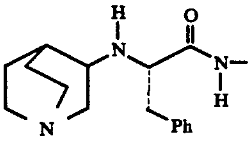 | $-OCH_2Ph$ |
| 277 | 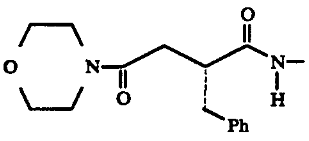 | 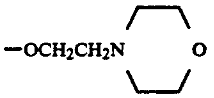 |
| 278 | 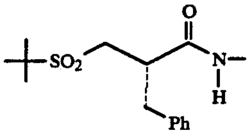 | —O-i-Pr |

TABLE 18-continued
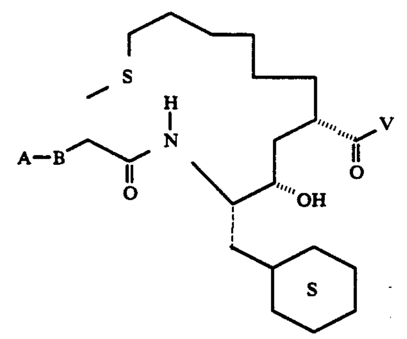
| Number | A—B | V |
|---|---|---|
| 279 | 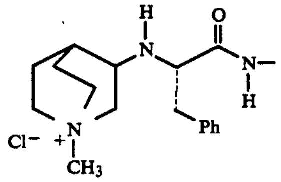 | —O-i-Pr |
| 280 | 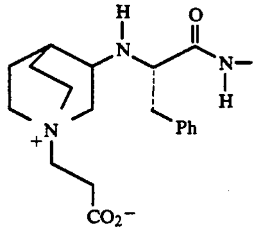 | —O-i-Pr |
| 281 | 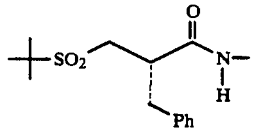 | 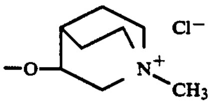 |
| 282 | 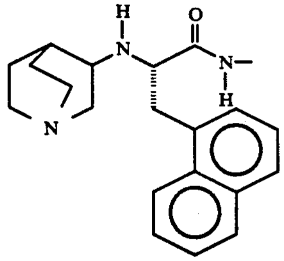 | 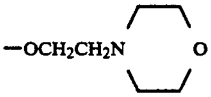 |
| 283 | 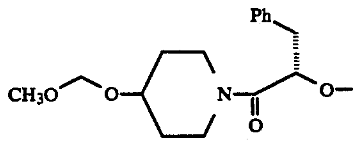 | 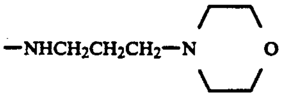 |
| 284 | 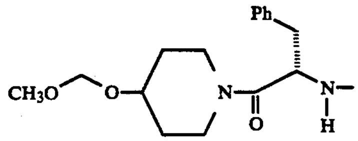 | 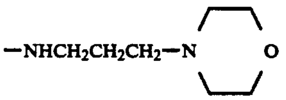 |

TABLE 19
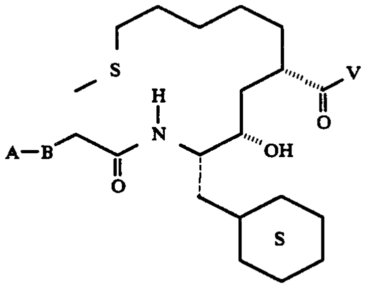
| Number | A—B | V |
|---|---|---|
| 285 | Boc—Phe—NH | —O-i-Pr |
| 286 | Boc—Phe—NH | —NH-2(S)-methylbutyl |
| 287 | Cbz—NH— | —O-i-Bu |
| 288 | 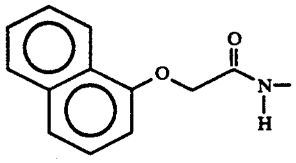 | —O-i-Pr |
| 289 | 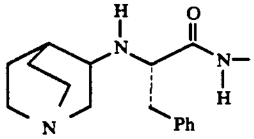 | —O-i-Pr |
| 290 | 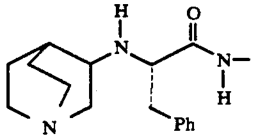 | 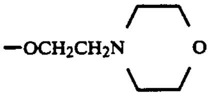 |
| 291 | 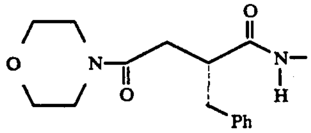 | 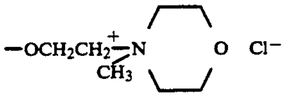 |
| 172 | Boc—Phe—NH | 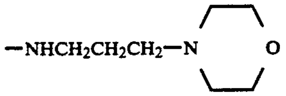 |
| 292 | 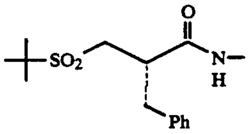 | 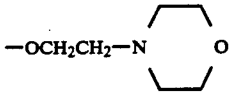 |
| 293 | 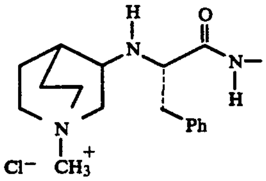 | —O-i-Pr |
| 294 | 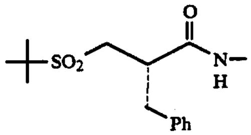 | 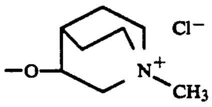 |

TABLE 19-continued
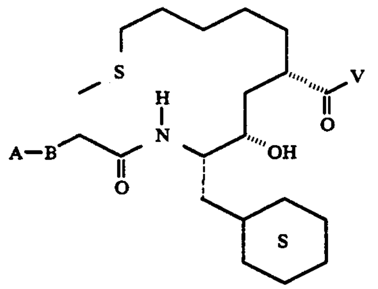
| Number | A—B | V |
| --- | --- | --- |
| 295 | 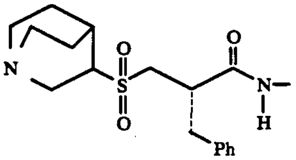 | 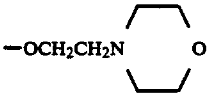 |
| 296 | 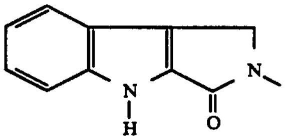 | —O-i-Pr |
| 297 | 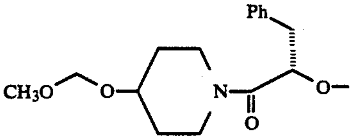 | 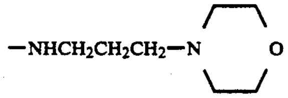 |
| 174 | 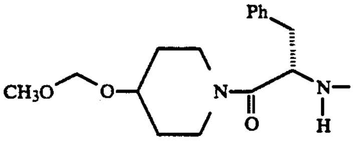 | 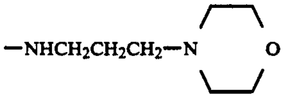 |
| 298 | 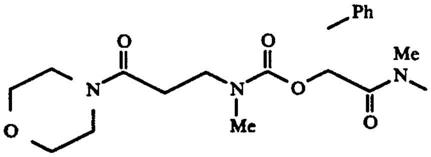 | 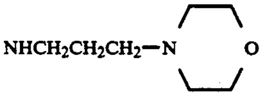 |
| 299 | 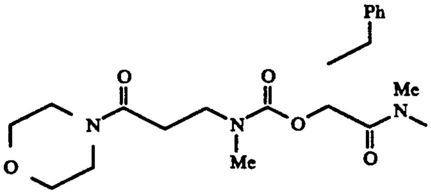 | 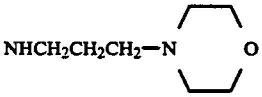 |
| 300 | 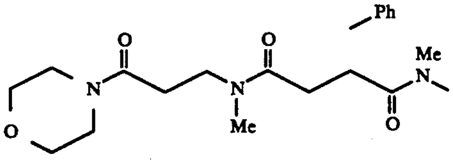 | 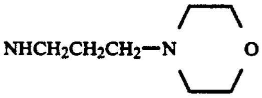 |

TABLE 19-continued
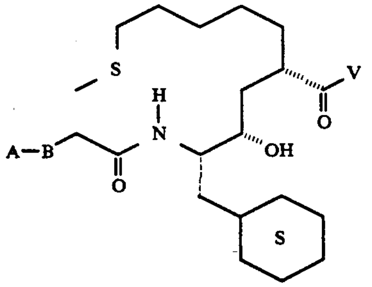
| Number | A—B | V |
|---|---|---|
| 301 | 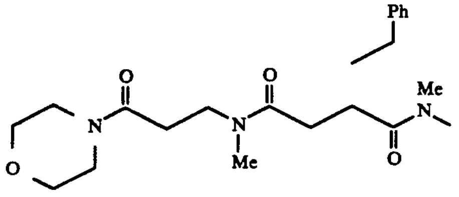 | 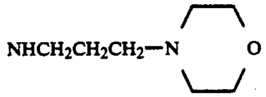 |
| 302 | 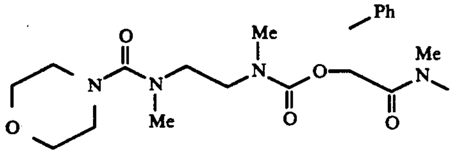 | 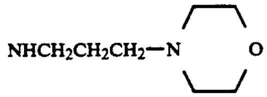 |
| 303 | 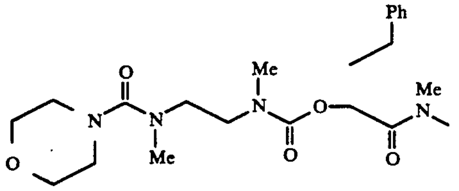 | 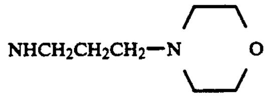 |
| 304 | 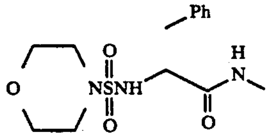 | 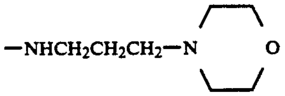 |
| 305 | 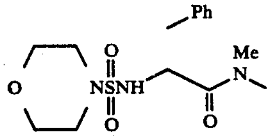 | 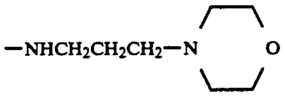 |
| 306 | 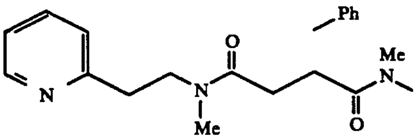 | 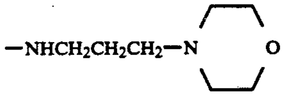 |
| 307 | 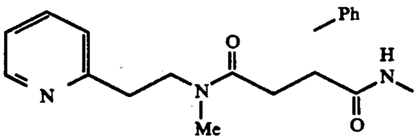 | 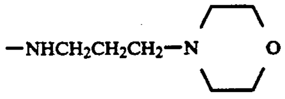 |
As can be seen, a unique aspect and essential feature of the present invention is the incorporation of cyclic elements into the inhibitors thereby inparting enhanced oral absorption.
The abbreviations used herein have the following meaning:

| Abbreviated Designation | |
|---|---|
| | Amino Acid/Residue |
| ACHPA | (3S,4S)-4-amino-5-cyclohexyl-3-hydroxypentanoic acid |
| HomoPhe | 2(S)-amino-4-phenylbutyric acid |
| Ile | L-isoleucine |
| Glu | L-glutamate |
| Ser | L-serine |
| (p-MeO)Phe | L-para-methoxyphenylalanine |
| Phe | L-phenylalanine |
| Nal | 3-(1-naphthyl)-alanine |
| Tyr | L-tyrosine |
| | Protecting Group |
| BOC(Boc) | t-butyloxycarbonyl |
| CBZ(Cbz) | benzyloxycarbonyl(carbobenzoxy) |
| DNP | 2,4-dinitrophenyl |
| IPOC | isopropyloxycarbonyl |
| FMOC(Fmoc) | 9-fluorenylmethyloxycarbonyl |
| TBDMSi | t-butyldimethylsilyl |
| TBDMSiCl | t-butyldimethylsilylchloride |
| | Activating Group |
| HBT(HOBt) | 1-hydroxybenzotriazole hydrate |
| HOSu | N-hydroxysuccinimide |
| | Condensing Agent |
| DCCI (DCC) | dicyclohexylcarbodiimide |
| DPPA | diphenylphosphorylazide |
| | Amino Acid/Residue |
| EDC | 1-(3-dimethylaminopropyl)-3-ethyl-carbodiimide hydrochloride |
| | Reagent |
| $(BOC)_2O$ | di-t-butyl dicarbonate |
| DIBAL | diisobutylaluminum hydride |
| DIPEA | diisopropylethylamine |
| DMAP | 4-(dimethylamino)pyridine |
| TEA | triethylamine |
| TFA | trifluoroacetic acid |
| LAH | lithium aluminum hydride |
| LDA | lithium diisopropylamide |
| MCPBA | 3-chloroperoxybenzoic acid |
| NMM | N-methyl morpholine |
| PPTS | pyridinium para-toluenesulfonate |
| TBAF | tetra-n-butylammonium fluoride |
| TsOH | p-toluene sulfonic acid |
| | Solvent |
| HOAc (AcOH) | acetic acid |
| DMF | dimethylformamide |
| DMSO | dimethyl sulfoxide |
| EtOAc | ethyl acetate |
| EtOH | ethanol |
| $Et_2O$ | ether |
| MeOH | methanol |
| THF | tetrahydrofuran |
| Hex(hex) | hexane |
| rt | room temperature |

The Formula I compounds can be used in the form of salts derived from inorganic or organic acids and bases when there is an acidic or basic function. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobrimide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides: dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel compounds of the present invention possess an excellent degree of activity in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection of infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The peptides of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 2 to 35 grams per day are useful in the treatment of the above indicated conditions. For example, renin-associated hypertension and hyperaldosteronism are effectively treated by the administration of from 30 milligrams to 0.5 grams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, the compounds of the invention are useful in treating hypertension. They are also of value in the management of acute and chronic congestive heart failure. These compounds may also be expected to be useful in the treatment of secondary hyperaldosteronism, primary and secondary pulomary hyperaldosteronism, primary and secondary pulomary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperplasia, and to minimize the atherosclerotic process. The application of the compounds of this invention for these and similar disorders will be apparent to those skilled in the art.

The compound so of this invention are also useful to treat elevated intraocular pressure and to enhance retinal blood flow and can be administered to patients in need of such treatment with typical pharmaceutical formulations such as tablets, capsules, injectables and thelike as well as topical ocular formulations in the form of solution, ointments, inserts, gel, and the like. Pharamecutical formulations prepared to treat intraocular pressure would typically contain about 0.1% to 15% by weight, preferably 0.5% to 2% by weight, of a compound of this invention.

Thus, in accordance with the present invention there is further provided a pharmaceutical composition for treating renin-associated hypertension and hyperaldosteronism, comprising a pharmaceutical carrier and a therapeutically effective amount of Compound I.

The renin inhibitory compound of the present invention may also be utilized in diagnostic methods for the purpose of establishing the significance of renin as a causative or contributory factor in hypertension or hyperaldosteronism in a particular patient. For this purpose the novel peptides of the present invention may be administered in a single dose of from 0.1 to 10 mg per kg of body weight.

Both in vivo and in vitro methods may be employed. In the vivo method, a novel compound of the present invention is administered to a patient, preferably by intravenous injection, although parenteral administration is also suitable, at a hypotensive dosage level and as a single dose, and there may result a transitory fall in blood pressure. This fall in blood pressure, if it occurs, indicates supranormal plasma renin levels.

An in vitro method which may be employed involves incubating a body fluid, preferably plasma, with a novel compound of the present invention and, after deproteinization, measuring the amount of angiotensin II produced in nephrectomized, pentolinium-treated rats. Another in vitro method involves mixing the plasma or other body fluid with a novel compound of the present invention and injecting the mixture into a test animal. The difference in pressor response with and without added peptide is a measure of the renin content of the plasma.

The following method was used for in vitro evaluation of the renin inhibitors of Formula I: The human plasma renin $IC_{50}$ values for inhibitors of Formula I were determined at pH 7.4 following the procedure described in J. Boger, L. S. Payne, D. S. Perlow, N. S. Lohr, M. Poe, E. H. Blaine, E. H. Ulm, T. W. Schorn, B. I. Lamont, T. Y. Lin, M. Kawai, D. H. Rich and D. F. Veber, J. Med. Che., 28, 1779 (1985).

The following methods were used for in vivo evaluation of the renin inhibitors of Formula I: Intravenous evaluation of renin inhibitors in concious sodium-deficient Rhesus monkeys: Rhesus monkeys, male and female, weighing 2.6–4.5 Kg, were surgically prepared with chronic arterial and venous catheters and vascular access ports for direct monitoring of mean arterial pressure (MAP) and heart rate (HR). The animals were maintained on a low sodium diet (1.2 mmol Na/day) plus friut for a week, and administered LASIX (furosemide) at 2.5 mg/Kg, intramuscularly the evening prior to the experiment. The animals had been trained to sit quietly in the chairs with water ad libium for the duration of the experiment. The inhibitors were administered by bolus injection using 0.5% acetic acid-5% dextrose in water as the vehicle (0.4 ml/Kg), and MAP and HR were measured. Blood samples were withdrawn at different time intervals beginning at the nadir of hypotensive response. PRA was determined as described above. The responsiveness of the animal during the experiment was verified with the standard inhibitor, SCRIP (Iva-His-Pro-Phe-His-Sta-Leu-Phe-$NH_2$, $IC_{50}=3.7$ nM). The i.v. dose of the standard inhibitor required to lower blood pressure by 50% of the maximal response was determined ($ED_{50}=0.039$ umoles/Kg). Inhibitors were tested at doses which were derived by comparing their $IC_{50}$ values to that of SCRIP. A projected $ED_{50}$ dose for each inhibitor was calculated using the following furmula: $ED_{50}$ (Test Inhibitor, umoles/Kg)$=ED_{50}$ (SCRIP)$\times$[$IC_{50}$ (Test Inhibitor)/$IC_{50}$ (SCRIP)], where the $IC_{50}$ values were determined against human plasma renin. In order to assure initial complete inhibition of endogenous monkey renin after i.v. administration, a multiple of projected $ED_{50}$ dose was chosen for each inhibitor. Percent inhibition of monkey PRA, changes in MAP and HR were calculated and plotted against time. The data points are averages of two or more monkey experiments. Protocol for oral administration of renin inhibitors in conscious sodium-deficient Rhesus monkeys: Rhesus monkeys of either sex were surgically prepared and sodium depleted for administration of compounds orally, as described above. The animals were fitted with a nasogastric feeding tube for oral administration of inhibitors. The inhibitors were administered orally as a solution (2.5 ml/Kg) in 0.1M citric acid, and MAP and HR were measured over time. Plasma samples were collected at different time intervals up to 6 hours, and plasma renin activity (PRA) (ng AI/ml/hr) was determined using the RIA method (Travenol genetech's RIA Kit). Percent inhibition of primate PRA and peak changes in MAP and HR were calculated. All data points are an average of 2–5 monkey experiments.

The compounds of the present invention are prepared using methods such as those described below and illustrated in the following reaction schemes (I, II & III).

The following carboxylic acids, useful in preparing macrocyclic inhibitors of Formula I may be prepared by methods described in the following references:

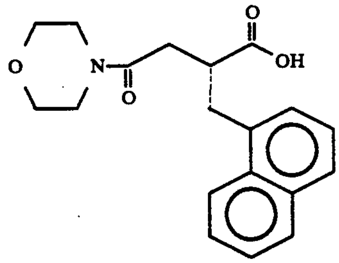

K. Iizuka et al., J. Med. Chem., 31, 704 (1988)

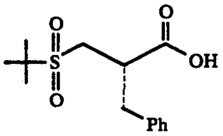

P. Buhlmayer et al., J. Med. Chem., 31 1839 (1988)

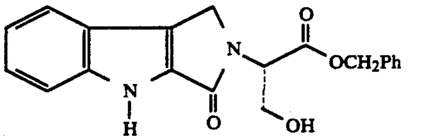

D. J. Kempf et al., "Design and Synthesis of Rigid Heterocyclic Phenylalamine Replacements for Incorporation into Renin Inhibitors," Proceedings of 11th Am. Peptide Symposium, Salk institute, University of California, San Diego, July 9-14, 1989, ESCOM Scientific Publishers, BV Leiden, The Netherlands.

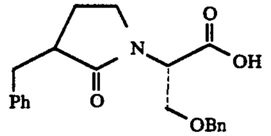

S. Thaisrivongs et al., J. Med. Chem., 31, 1371 (1988).

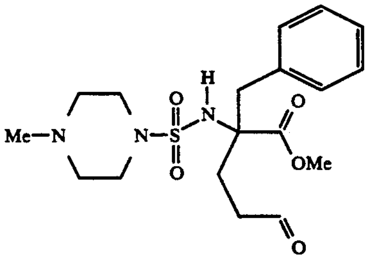

B. De, et. al., European Patent Application No. EP0365992, published May 2, 1990.

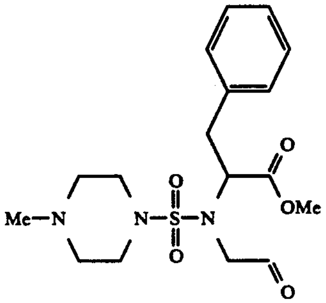

B. De, et. al., European Patent Application No. EP0365992, published May 2, 1990.

-continued

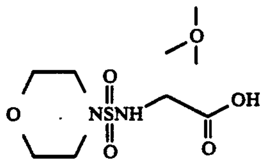

J. M. Hamby et. al. EP0380805 A1, published Aug. 8, 1990.

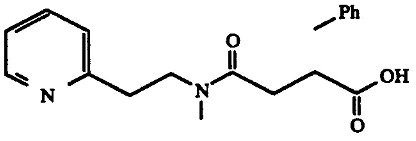

S. H. Rosenberg et. al. EP0410260 A2 published Jan. 30, 1991.

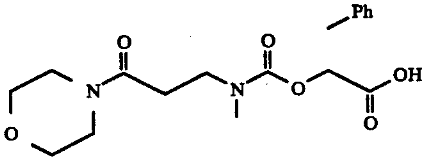

K. Hemmi et. al. USP 4,921,855 published May 1, 1990.

Preparation of Macrocyclic Renin Inhibitors of Formula I in which D=—CONH—, W=—NH—, s=1, n=0 and t=3

Scheme I illustrates the preparation of macrocylic renin inhibitors of formula I in which D=—CONH—, W=—NH—, s=1, n=0 and t=3. A 2-substituted ACHPA, protected as the acetonide derivative (4; V=—OH) is prepared as shown, using the chiral oxazolidinone 2 and the optically active aldehyde 1. This 2-substituted ACHPA analog, may be esterified, for example to the methyl ester by treatment with ethereal diazomethane, or converted to amide derivatives 4 using standard procedures for amide formation. As shown in Scheme I, the olefinic side chain of the resulting analog 5 is transformed to yield the protected amino derivative 8. Removal of the Boc and acetonide protecting groups from 8, and coupling of the resulting free amino group with a protected analog of glutamic acid, yields the cyclization precursor 9, which after hydrogenolytic removal of the Cbz and benzyl ester protecting groups, is cyclized to give macrocycle 10. Other amides and esters prepared from 4 (V=—OH) may likewise be used to prepare macrocyclic analogs 10 using similar procedures. Alternatively, 10 (V=—$OCH_3$) may be prepared, and after hydrolysis of the C-terminal ester group, the resulting carboxylic acid 10 (V=—OH) used to prepare other esters and amides using standard coupling procedures, for example, using EDC and DMAP. After removal of the Boc protecting group from 10, the resulting amino derivative is coupled with carboxylic acids, acid chlorides, or sulfonyl chlorides using standard coupling procedures to yield macrocycles 11.

SCHEME I

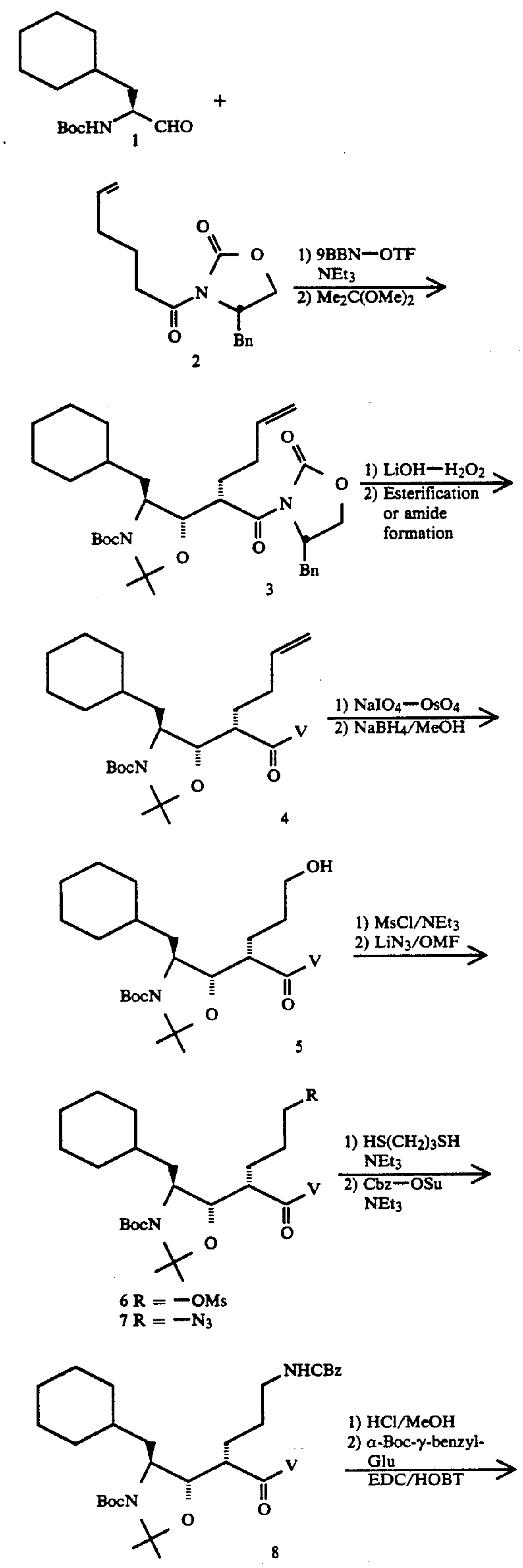

1

2

3

4

5

6 R = —OMs
7 R = —$N_3$

8

-continued

SCHEME I

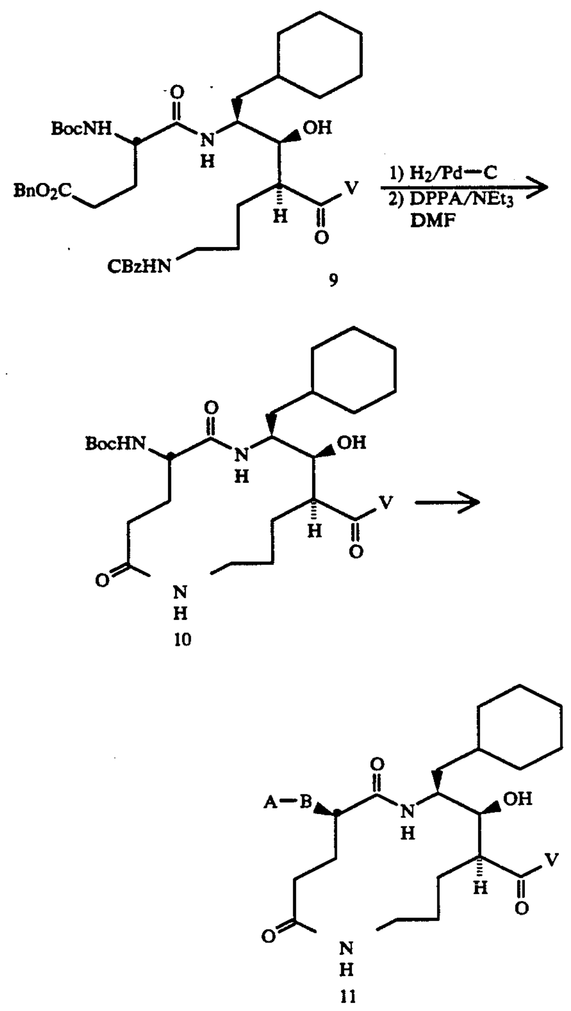

9

10

11

Preparation of imide 2

To a solution of 5-hexenoic acid (1.61 g; 14.17 mmol) in dry THF (50 mL) cooled to −78° C. under nitrogen was added $Et_3N$ (2.36 mL; 1.2 equiv.) and pivaloyl chloride (1.75 mL; 1.0 equiv.). The resultant white slurry was stirred at −78° C. for 10 minutes then warmed to 0° C. and stirred for 20 minutes. While the above slurry was stirring, to a solution of (S)-(−)-4-benzyl-2-oxazolidinone (2.09 g; 11.81 mmol) in a separate flask in dry THF (40 mL) under nitrogen cooled to −78° C. was added 1.6M n-BuLi (8.12 mL; 1.1 equiv.). This second solution was stirred for 30 minutes at −78° C. and then added through a cannula to the first solution and the entire mixture was stirred at −78° C. for 10 minutes and then at 0° C. for 30 minutes. The reaction was quenched with a sat'd solution of $NH_4Cl$ and the volatiles were removed in vacuo. The residue was taken up in ether and the organic was washed with 1N NaOH (3×15 mL), 0.5N HCl (2×10 mL) and brine. The organic was dried over anhydrous $MgSO_4$ and concentrated in vacuo. The product was purified by flash chromatography on a silica column eluting with Hex-/EtOAc (6:1) to yield 2.78 g (90%) of imide 2. $^1H$ NMR (300 MHz, $CDCl_3$) δ 1.82 (m, 2H), 2.18 (q, 2H), 2.77

(dd, 1H), 2.95 (m, 2H), 3.30 (dd, 1H), 4.18 (m, 2H), 4.67 (m, 1H), 5.00 (dd, 1H), 5.07 (dd, 1H), 5.84 (m, 1H), 7.19–7.27 (comp, 5H).

Preparation of acetonide 3

To a solution of imide 2 (1.64 g; 6.28 mmol) in dry $CH_2Cl_2$ (12 mL) cooled to 0° C. under nitrogen was added a 0.5M solution of 9-BBN-OTf in hexanes (12.6 mL; 1.0 equiv.) very slowly through a syringe (throughout 10 minutes). To the resultant yellow solution was slowly added $NEt_3$ (1.04 mL; 1.2 equiv.) at which time the color faded to very faint yellow. After stirring the mixture for 30 minutes at 0° C. a solution of aldehyde 1 (890 mg; 3.49 mmol) in $CH_2Cl_2$ (2 mL) was added through a cannula. After stirring at 0° C. for 30 minutes the reaction was quenched at 0° C. with pH 7 buffer (6 mL) and MeOH (18 mL). To this mixture stirring at 0° C. was added a 2:1 $MeOH/H_2O_2$ solution (18 mL) very slowly throughout 1 hr. The mixture was allowed to come to room temperature and the volatiles were removed in vacuo. The remaining residue was extracted with ether, washed with brine, dried over $MgSO_4$ and concentrated in vacuo providing crude product. To a solution of the crude aldol adduct in $CH_2Cl_2$ (10 mL) was added dimethoxypropane (2 mL) and a catalytic amount of TsOH (60 mg). After stirring for 2 hours the mixture was diluted with ether (100 mL) and washed with sat'd $NaHCO_3$ solution and brine. The organic was dried over anhydrous $MgSO_4$ and concentrated in vacuo. The product was purified by flash chromatography on a silica column eluting with Hex/EtOAc (10:1) to yield 1.23 g (63%) of acetonide 3. $^1H$ NMR (300 MHz, $CDCl_3$) δ 0.81–1.05 (comp m, 2H), 1.15–1.38 (comp, 5H), 1.48 (s, 12H), 1.52 (s, 3H), 1.65 (bs, 6H), 2.01 (comp m, 2H), 2.15 (comp m, 2H), 2.69 (dd, 1H), 3.36 (bd, 1H), 3.71 (bm, 1H), 4.00 (bs, 1H), 4.18 (bs, 2H), 4.33 (bs, 1H), 4.60 (bm, 1H), 5.00 (dd, 1H), 5.05 (dd, 1H), 5.82 (comp m, 1H), 7.20–7.38 (comp, 5H); FAB mass spectrum, m/e 623 (m+H+54, calcd for $C_{33}H_{48}N_2O_6$, 623). Anal. Calcd. for $C_{33}H_{48}N_2O_6$: C, 69.69; H, 8.51; N, 4.93. Found: C, 69.70; H, 8.46; N, 4.93.

Preparation of amide 4 (V=—NH—2(S)-methylbutyl)

To a solution of acetonide 3 (231 mg; 0.407 mmol) in a 3:1 $THF/H_2O$ mixture (8 mL) cooled to 0° C. was added 30% $H_2O_2$ (375 μL; 8 equiv.) and LiOH-$H_2O$ (35 mg; 2 equiv.). The reaction was stirred at 0° C. for 6 hours then at 5° C. for 2 days. The reaction was quenched with a solution of $Na_2SO_3$ (400 mg) in $H_2O$ (3 mL) and the volatiles were removed in vacuo. The residue was taken up in EtOAc, washed with 10% citric acid solution, brine and concentrated in vacuo. To a solution of the crude acid 4 (V=—OH) in dry $CH_2Cl_2$ (2 mL) cooled to 0° C. under nitrogen was added 2(S)-methyl-butyl amine (95 μL; 2.0 equiv.), HOBT (109 mg; 2.0 equiv.) and EDC (156 mg; 2.0 equiv.). The reaction was allowed to warm to room temperature while stirring. After stirring for 2 days additional amine (95 μL; 2.0 equiv.) and EDC (156 mg; 2.0 equiv.) were added. After a total of 4 days the mixture was diluted with ether, washed with 0.5N HCl, 1.0N NaOH and brine. The organic phase was dried over anhydrous $MgSO_4$ and concentrated in vacuo. The product was purified by flash chromatography on a silica column eluting with Hex/EtOAc (10:1 to 3:1) to yield 157 mg (81%) of amide 4. $^1H$ NMR (300 MHz, $CDCl_3$) δ 0.75–0.98 (comp, 7H), 1.10–1.21 (comp, 5H), 1.49 (s, 12H), 1.50–2.00 (comp, 17H), 2.21 (m, 2H), 3.12 (bt, 2H), 3.75 (bm, 1H), 4.01 (d, 1H), 4.98 (dd, 1H), 5.03 (dd, 1H), 5.56 (bs, 1H), 5.77 (comp m, 1H); FAB mass spectrum, m/e 533 (m+H+54, calcd for $C_{28}H_{50}N_2O_4$, 533). Anal. Calcd. for $C_{28}H_{50}N_2O_4$: C, 70.25; H, 10.53; N, 5.85. Found: C, 70.04; H, 10.59; N, 5.80.

Preparation of alcohol 5 (V=—NH-2(S)-methylbutyl)

To a solution of amide 4 (V=—NH-2(S)-methylbutyl) (384 mg; 0.803 mmol) in dry THF at room temperature was added a 2.5% w/v solution of $OsO_4$ (250 μL) and $NaIO_4$ (344 mg; 2.0 equiv.) in $H_2O$ (6 mL). After 3 hours the mixture was diluted with ether/EtOAc washed with $H_2O$, a sat'd solution of $Na_2SO_3$, and brine. The organic was dried over anhydrous $MgSO_4$ and concentrated in vacuo. The residue was dissolved in MeOH (3 mL) the solution was cooled to 0° C. and $NaBH_4$ (29 mg; 1.0 equiv.) was added. After several minutes TLC analysis (1:1 EtOAc/Hex) indicated the reaction was complete. The mixture was diluted with EtOAc, washed with a sat'd solution of $NH_4Cl$ and brine. The organic was dried over anhydrous $MgSO_4$ and concentrated in vacuo. The product was purified by flash chromatography on a silica column eluting with EtOAc/hex (1.2:1 to 6:1) to yield 234 mg (60%) of alcohol 5. $^1H$ NMR (300 MHz, $CDCl_3$) δ 0.78–1.03 (comp, 7H), 1.10–1.31 (comp m, 5H), 1.49 (s, 12H), 1.38–1.79 (comp, 16H), 1.87 (m, 1H), 2.35 (bm, 1H), 3.12 (bt, 2H), 3.60–3.90 (b comp m, 4H), 4.03 (d, 1H), 5.89 (bs, 1H).

Preparation of mesylate 6 (V=—NH—2(S)-methylbutyl)

To a solution of alcohol 5 (V=—NH—2(S)-methylbutyl) (100 mg; 0.2075 mmol) in $CH_2Cl_2$ (1 mL) cooled to 0° C. under nitrogen was added $Et_3N$ (32 μL; 2.0 equiv.) and MsCl (72 μL; 2.5 equiv.). After several minutes the mixture was diluted with ether, washed with 1.0N NaOH, 0.5N HCl and brine. The organic was dried over anhydrous $MgSO_4$ and concentrated in vacuo to afford 131 mg (>100%) of crude mesylate 6 which appeared quite pure by NMR analysis. $^1H$ NMR characteristic signals (300 MHz, $CDCl_3$) δ 1.51 (s, 12H), 2.30 (bs, 1H), 3.00 (s, 3H), 3.80 (bm, 1H), 4.03 (d, 1H), 4.25 (m, 2H), 5.80 (bs, 1H).

Preparation of azide 7 (V=—NH—2(S)-methylbutyl)

To a solution of mesylate 6 (V=—NH—2(S)—methylbutyl) (131 mg; 0.234 mmol) in dry DMF (1 mL) was added $LiN_3$ (57 mg; 5 equiv.). After stirring at room temperature for 16 hours the mixture was diluted with ether/EtOAc, washed with $H_2O$ and brine. The organic was dried over anhydrous $MgSO_4$ and concentrated in vacuo. The product was purified by flash chromatography on a silica column eluting with Hex/EtOAc (4:1) to yield 100.1 mg (84%) of azide 7. $^1H$ NMR (300 MHz, $CDCl_3$) δ 0.78–0.99 (comp, 7H), 1.10–1.32 (comp, 5H), 1.47 (s, 12H), 1.32–1.79 (comp, 16H), 1.83 (comp m, 1H), 2.22 (bt, 1H), 3.12 (bs, 2H), 3.38 (m, 2H), 4.02 (d, 1H), 5.69 (bs, 1H); Anal. Calcd. for $C_{27}H_{49}N_5O_4$: C, 63.47; H, 9.73; N, 13.79. Found: C, 63.85; H, 9.93; N, 13.55.

Preparation of CBz amine 8 (V=—NH—2(S)-methylbutyl)

To a solution of azide 7 (V=—NH—2(S)-methylbutyl) (59 mg; 0.1163 mmol) in degassed MeOH (0.5 mL) at room temp was added $Et_3N$ (49 μL; 3.0 equiv.) and 1,3-propane dithiol (35 μL; 3.0 equiv.). The reaction was stirred under nitrogen for 2 days then filtered and concentrated in vacuo. The residue was dissolved in THF (1 mL) and $Et_3N$ (49 μL; 3.0 equiv.) and CBz-succinimide (58 mg, 2.0 equiv.) was added. After 1 day the mixture was diluted with EtOAc and washed with 1.0N NaOH and brine. The organic was dried over anhydrous $MgSO_4$ and concentrated in vacuo. The product was purified by flash chromatography on a silica column eluting with Hex/EtOAc (3:1) to yield 68 mg (95%) of CBz amine 8. $^1H$ NMR characteristic signals (300 MHz, $CDCl_3$) δ 0.89–0.97 (comp, 8H), 1.50 (s, 12H), 1.57 (s, 3H), 2.27 (bs, 1H), 3.00–3.30 (comp, 5H), 4.01 (d, 1H), 4.82 (bm, 1H), 5.09 (s, 2H), 5.81 (bm, 1H), 7.35 (m, 5H).

Preparation of benzyl ester 9 (V=—NH—2(S)-methylbutyl)

To CBz amine 8 (V=—NH—2(S)-methylbutyl) (15 mg; 0.0244 mmol) was added a sat'd solution of MeOH/HCl (1 mL) and the mixture was allowed to stand at room temperature for 2 hours and then concentrated in vacuo. The resultant HCl salt was dried at high vacuum over $P_2O_5$ for 2 hours and then dissolved in $CH_2Cl_2$ (1 mL) and $NEt_3$ (6.7 μL; 2.0 equiv.). The resulting solution was cooled to 0° C. and α-Boc-γ-benzyl glutamic acid (16 mg; 2.0 equiv.), HOBT (10 mg; 3.0 equiv.) and EDC (10 mg; 2.0 equiv.) were added. The reaction was allowed to warm slowly to room temperature and after 12 hours was diluted with EtOAc. The mixture was with 0.5N HCl 1.0N NaOH and brine. The organic was dried over anhydrous $MgSO_4$ and concentrated in vacuo. The product was purified by flash chromatography on a silica column eluting with Hex/EtOAc (1:2) to yield 18 mg (93%) of benzyl ester 9. $^1H$ NMR characteristic signals (300 MHz, $CDCl_3$) δ 0.91 (comp, 8H), 1.08–1.30 (comp, 8H), 1.47 (s, 9H), 1.92–2.21 (comp, 4H), 2.49 (q, 2H), 2.85 (d, 1H), 2.96 (m, 1H), 3.15 (q, 2H), 3.26 (m, 2H), 3.61 (bt, 1H), 3.98 (m, 2H), 5.07 (s, 1H), 5.12 (s, 3H), 5.55 (bs, 1H), 6.42 (d, 1H), 7.12 (bt, 1H), 7.37 (comp, 10H).

Preparation of macrocycle 10 (V=—NH—2(S)—methylbutyl)

To a solution of benzyl ester 8 (V=—NH—2(S)-methylbutyl) (18 mg; 0.0227 mmol) in MeOH (2 mL) was added 10% Pd on carbon (15 mg). A hydrogen atmosphere was secured with a balloon, and the reaction was stirred overnight at room temperature. The next day all the starting material had been consumed, and the catalyst was removed by filtration through a plug of celite. The solvent was removed in vacuo and the residue (17 mg) was dissolved in dry DMF (17 mL). This solution was cooled to 0° C. under nitrogen and $Et_3N$ (17 μL; 4.0 equiv.) and DPPA (26 μL; 4 equiv.) were added. The reaction was stirred at 0° C. for 1 hour and then placed in the cold room (ca. 4° C.) for 6 days. The DMF was removed under high vacuum and the residue was taken up in EtOAc and washed with $H_2O$ and brine. The organic was dried over anhydrous $MgSO_4$ and concentrated in vacuo. The product was purified by flash chromatography on a silica column, eluting with EtOAc to EtOAc/MeOH (30:1), to yield 3.1 mg (18%) of macrocycle 10. $^1H$ NMR characteristic signals (300 MHz, $CDCl_3$) δ 0.75–1.03 (comp, 8H), 1.08–1.32 (comp, 10H), 1.44 (s, 9H), 3.01 (s, 2H), 3.15 (bt, 1H), 3.90 (comp m, 1H), 4.19 (m, 1H), 4.32 (bs, 1H), 5.63 (bm, 2H), 5.81 (bs, 1H), 7.68 (bm, 1H); FAB mass spectrum, m/e 553 (m+H, calcd for $C_{29}H_{52}N_4O_6$, 553).

Preparation of Macrocycle 11-1 (A-B=Boc-Phe-NH; V=—NH—2(S)-methylbutyl)

To macrocycle 10 (V=—NH—2(S)-methylbutyl) (4.6 mg; 0.0083 mmol) was added a sat'd solution of MeOH/HCl (1 mL) and the mixture was allowed to stand at room temperature for 1 hour and then concentrated in vacuo. The resultant HCl salt was dried at high vacuum over $P_2O_5$ for 3 hours and then dissolved in $CH_2Cl_2$ (1 mL) and $NEt_3$ (3.5 μL; 3 equiv.). This mixture was cooled to 0° C. under nitrogen and HOBT (5.6 mg; 5 equiv.), Boc-Phe (4.4 mg; 2 equiv.) and EDC (3.0 mg; 2 equiv.) were added. The reaction was allowed to warm to room temperature and stirred overnight. The next day the reaction was diluted with EtOAc and washed with 0.5N HCl, 1.0N NaOH and brine. The organic was dried over anhydrous $MgSO_4$ and concentrated in vacuo. The product was purified by flash chromatography on a silica column eluting with $CH_2Cl_2$/MeOH (80:2 to 80:4) to yield 4.2 mg (72%) of macrocycle 11. $^1H$ NMR characteristic signals (300 MHz, $CD_3OD$) δ 0.78–1.04 (comp, 8H), 1.39 (s, 9H), 2.20–2.42 (comp, 4H), 3.89 (comp m, 1H), 4.31 (comp m, 1H), 4.47 (bs, 1H), 7.29 (comp, 5H), 8.10 (bt, 1H); FAB mass spectrum, m/e 705 (m+H, calcd for $C_{38}H_{56}N_5O_7D_5$, 705).

Preparation of Macrocycle 11-4

The carboxylic acid prepared by treatment of 3 with lithium hydroxide and hydrogen peroxide is esterified by treatment with diazomethane, yielding 4 (V=—$OCH_3$). Procedures similar to those described above are then used to prepare 10 (V=—$OCH_3$). Saponification of ester 10 (V=—$OCH_3$) yields the corresponding carboxylic acid 10 (V=—OH) which is coupled with N-(2-hydroxyethyl)morpholine to afford 10 [V=—$OCH_2CH_2$(morpholin-4-yl)]. The Boc protecting group is then removed this ester by treatment with anhydrous TFA, and the resulting amino analog is coupled with N-(quinuclidin-3(S)-yl)-phenylalanine (27S) using conditions similar to those described above to provide the title compound.

Preparation of Macrocycle 11-7

Using the procedures described above and replacing N-(quinuclidin-3(S)-yl)-phenylalanine with 2-[(morpolin-4-yl)carbonyl]methyl-3-phenylpropionic acid, the title compound may be prepared.

Preparation of Macrocycle 11-8

Using the procedures described above and replacing N-(2-hydroxyethyl)morpholine with isopropanol and replacing N-(quinuclidin-3(S)-yl)-phenylalanine with 2(R)-(t-butylsulfonyl)methyl-3-phenylpropionic acid, the title compound may be prepared.

Preparation of Macrocycle 11-10

Using the procedures described above and replacing N-(2-hydroxyethyl)morpholine with isopropanol and replacing N-(quinuclidin-3(S)-yl)-phenylalanine with N-[(N-methylquinuclidin-3(S)-yl)+$Cl^-$]-phenylalanine hydrochloride (29S), the title compound may be prepared.

Preparation of Macrocycle 11-15

Using the procedures described above and replacing N-(2-hydroxyethyl)morpholine with isopropanol and replacing N-(quinuclidin-3(S)-yl)-phenylalanine with 2(S)-(quinuclidin-3-yl)oxy-3-phenylpropionic acid (38), the title compound may be prepared.

Preparation of Macrocyclic Renin Inhibitors of Formula I in which D=—CONH—, W=—NH—, s=1, n=o and t=4

Scheme II illustrates the preparation of macrocylic renin inhibitors of formula I in which D= —CONH—, W=—NH—, s=1, n=o and t=4. As illustrated in Scheme 1, a 2-substituted ACHPA, protected as the acetonide derivative (4; V=—OH) may be esterified, for example to the methyl ester by treatment with ethereal diazomethane, or converted to amide derivatives 4 using standard procedures for amide formation. As shown in Scheme II, the olefinic side chain of the resulting analog 4 is transformed to yield the protected amino derivative 15. Removal of the Boc and acetonide protecting groups from 15, and coupling of the resulting free amino group with a protected analog of glutamic acid, yields the cyclization precursor 16, which after hydrogenolytic removal of the Cbz and benzyl ester protecting groups, is cyclized to give macrocycle 17. Other amides and esters prepared from 4 (V=—OH) may likewise be used to prepare macrocyclic analogs 17 using similar procedures. Alternatively, 17 (V=—$OCH_3$) may be prepared, and after hydrolysis of the C-terminal ester group, the resulting carboxylic acid 17 (V=—OH) used to prepare other esters and amides using standard coupling procedures. After removal of the Boc protecting group from 17, the resulting amino derivative is coupled with carboxylic acids, acid chlorides, or sulfonyl chlorides using standard coupling procedures to yield macrocycles 18.

SCHEME II

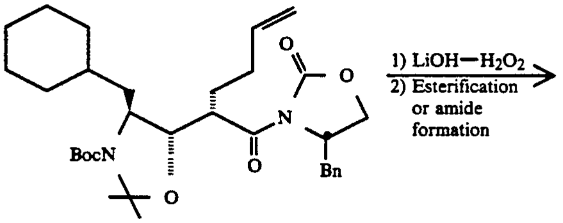

3

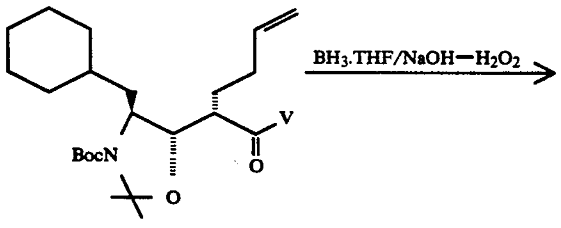

4

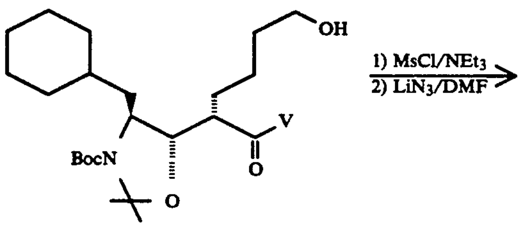

12

-continued

SCHEME II

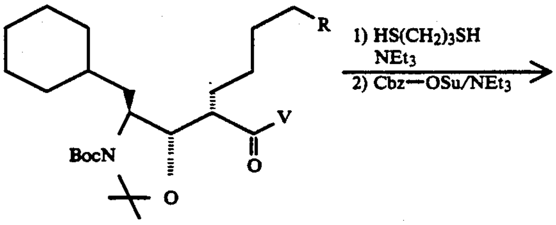

13 R = —OMS
14 R = $N_3$

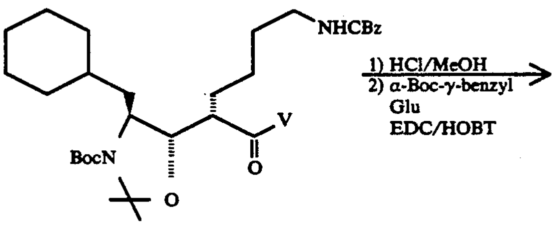

15

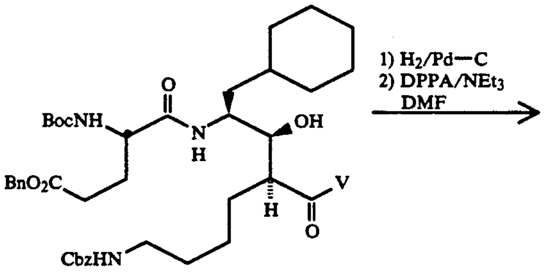

16

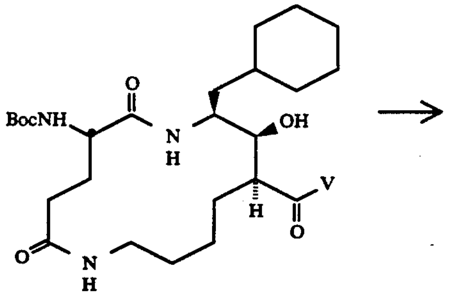

17

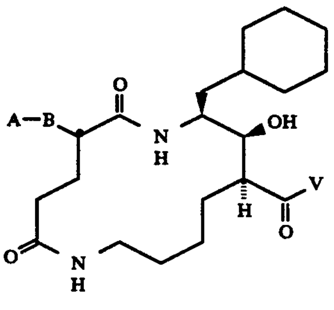

18

Preparation of methyl ester 4 ($V=-OCH_3$)

To a solution of imide 3 (310 mg; 0.546 mmol) in a 3/1 solution of $THF/H_2O$ (10 mL) cooled to 0° C. was added 30% $H_2O_2$ (503 μL; 8 equiv.) and LiOH (46 mg; 2 equiv.). The reaction was stirred for 1 hour at 0° C. and then at 4° C. for four days. The reaction was quenched with $Na_2SO_3$ (350 mg) in $H_2O$ (2 mL) and the volatiles were removed on the rotoevaporator. The residue was taken up in $Et_2O$/EtOAc and washed with a 10% citric acid solution and brine. The organic was dried over anhydrous $MgSO_4$ and concentrated in vacuo. The residue was dissolved in EtOAc and a solution of $CH_2N_2$ was added until the yellow color persisted. A stream of $N_2$ was bubbled in to remove any excess $CH_2N_2$ and the mixture was concentrated in vacuo. The product was purified by flash chromatography on a silica column eluting with Hex/EtOAc (7:1) to yield 210 mg (90%) of methyl ester. $^1H$ NMR characteristic signals (300 MHz, $CDCl_3$) δ 1.48 (s, 9H), 2.65 (bt, 1H), 3.67 (s, 3H), 3.95 (bd, 1H), 5.0 (m, 2H), 5.77 (comp m, 1H).

Preparation of primary alcohol 12 ($V=-NH-2(S)$-methylbutyl)

To a solution of amide 4 ($V=-NH-2(S)$-methylbutyl) (111 mg; 0.238 mmol) in dry THF (2 mL) cooled to 0° C. under $N_2$ was added 1.0M $BH_3$.THF (0.27 mL; 1.1 equiv.) The reaction was stirred for 10 minutes and then 1.0N NaOH was added followed by 30% $H_2O_2$ (240 μL; 9 equiv.). The mixture was stirred for 30 minutes at rt and then extracted with ether (3×25 mL) and washed with sat'd $Na_2SO_3$ and brine. The organic was dried over anhydrous $MgSO_4$ and concentrated in vacuo. The product was purified by flash chromatography on a silica column eluting with Hex/EtOAc (1.3:1) to yield 103 mg (89%) of the title compound. $^1H$ NMR characteristic signals (300 MHz, $CDCl_3$) δ 0.91 (comp m, 6H), 1.48 (s, 3H), 2.22 (dt, 1H), 3.60 (bs, 2H), 4.00 (d, 1H).

Preparation of primary alcohol 12 ($V=-OCH_3$)

To a solution of 4 ($V=-OCH_3$) (204 mg; 0.482 mmol) in dry THF (5 mL) cooled to 0° C. under $N_2$ was added 1.0M $BH_3$.THF (0.53 mL; 1.1 equiv.). The reaction was stirred for 30 minutes at 0° C. and then 1.0N NaOH (0.5 mL) and 30% $H_2O_2$ (0.46 mL) were added. The mixture was allowed to stir at rt for 15 minutes then extracted with $Et_2O$/EtOAc and washed with sat'd $Na_2SO_3$ and brine. The organic was dried over anhydrous $MgSO_4$ and concentrated in vacuo. The product was purified by flash chromatography on a silica column eluting with Hex/EtOAc (2.5:1) to yield 151 mg (71%) of the title compound as a solid with a mp=75° C. $^1H$ NMR characteristic signals (300 MHz, $CDCl_3$) δ 0.76–1.01 (comp m, 4H), 150 (s, 9H), 1.52 (s, 3H), 1.57 (s, 3H), 2.65 (dt, 1H), 3.62 (bm, 2H), 3.70 (s, 3H), 3.95 (bd, 1H). Anal. Calcd. for $C_{24}H_{43}O_6.\frac{1}{2}H_2O$: C, 63.97; H, 9.84; N, 3.11. Found: C, 64.26; H, 10.13; N, 3.14.

Preparation of mesylate 13 ($V=-NH-2(S)$-methylbutyl).

To a solution of alcohol 12 ($V=-NH-2(S)$-methylbutyl) (103 mg; 0.213 mmol) in $CH_2Cl_2$ (1 mL) cooled to 0° C. under $N_2$ was added $NEt_3$ (38 μL; 1.3 equiv.) and MsCl (20 μL; 1.2 equiv.). The reaction, which was complete almost instantly, was diluted with $Et_2O$ and washed with 0.5 N HCl, sat'd $NaHCO_3$ and brine. The organic was dried over anhydrous $MgSO_4$ and concentrated in vacuo to yield 119 mg (99%) of the title compound. $^1H$ NMR characteristic signals (300 MHz, $CDCl_3$) δ 0.93 (comp m, 6H), 1.48 (s, 9H), 1.52 (s, 3H), 1.59 (s, 3H), 2.23 (bt, 1H), 2.98 (s, 3H), 3.12 (bs, 1H), 4.00 (d, 1H), 4.21 (comp m, 2H), 5.67 (bs, 1H).

Preparation of azide 14 ($V=-NH-2(S)$-methylbutyl)

To a solution of mesylate 13 ($V=-NH-2(S)$-methylbutyl) (119 mg; 0.212 mmol) in dry DMF (1 mL) under $N_2$ was added $LiN_3$ (52 mg; 5 equiv.). After stirring at rt for ca. 16 hours the mixture was diluted with ether and washed with $H_2O$ and brine. The organic was dried over anhydrous $MgSO_4$ and concentrated in vacuo. The product was purified by flash chromatography on a silica column eluting with Hex/EtOAc (4:1) to yield 90.6 mg (84%) of the title compound as a solid with a mp=111°-112° C. $^1H$ NMR characteristic signals (300 MHz, $CDCl_3$) δ 0.92 (comp m, 6H), 1.48 (s, 9H), 1.48 (s, 9H), 2.20 (bd, 1H), 3.27 (comp m, 2H), 4.01 (d, 1H), 5.62 (bs, 1H). Anal. Calcd. for $C_{28}H_{51}N_5O_4$: C, 64.46; H, 9.85; N, 13.42. Found: C, 64.58; H, 9.97; N, 13.56.

Preparation of azide 14 ($V=OCH_3$)

To a solution of alcohol 12 ($V=-OCH_3$) (250 mg; 0.567 mmol) in $CH_2Cl_2$ (3 mL) cooled to 0° C. under $N_2$ was added $NEt_3$ (158 μL; 2 equiv.) and MsCl (66 μL; 1.5 equiv.). After 2.5 hours the mixture was diluted with $Et_2O$/EtOAc and washed with 1.0 N NaOH and brine. The organic was dried over anhydrous $MgSO_4$ and concentrated in vacuo. The residue (crude mesylate 17) was dissolved in dry DMF (2.5 mL) and $LiN_3$ (138 mg; 5 equiv.) was added. After stirring at rt for ca. 16 hours the mixture was diluted with ether and washed with $H_2O$ and brine. The organic was dried over anhydrous $MgSO_4$ and concentrated in vacuo. The product was purified by flash chromatography on a silica column eluting with Hex/EtOAc (6:1) to yield 261 mg (96%) of the title compound. $^1H$ NMR characteristic signals (300 MHz, $CDCl_3$) δ 1.49 (s, 9H), 2.63 (dt, 1H), 3.29 (t, 2H), 3.72 (s, 3H), 3.96 (bd, 1H). Anal. Calcd. for $C_{24}H_{42}N_4O_5$: C, 61.78; H, 9.07; N, 12.01. Found: C, 62.23; H, 9.51; N, 11.80.

Preparation of Cbz amine 15 ($V=-NH-2(S)$-methylbutyl)

To a solution of azide 14 ($V=-NH-2(S)$-methylbutyl) (195 mg; 0.374 mmol) in degassed MeOH (1.5 mL) was added $NEt_3$ (156 μL; 3 equiv.) and 1,3 propanedithiol (112 μL; 3 equiv.). The reaction was stirred at rt under $N_2$ for 24 hours. The reaction was diluted with EtOAc and filtered. The filtrate was concentrated in vacuo and the residue was dissolved in dry THF (2 mL) and $NEt_3$ (156 μL; 3 equiv.) and Cbz-hydroxysuccinimide (186 mg; 2 equiv.) were added. The mixture was stirred for 2 days and then diluted with EtOAc/$Et_2O$ and concentrated in vacuo. The product was purified by flash chromatography on a silica column eluting with Hex/EtOAc (3:1 to 2:1) to yield 197 mg (84%) of the title compound. $^1H$ NMR characteristic signals (300 MHz, $CDCl_3$) δ 0.91 (comp m, 6H), 1.48 (s, 9H), 2.20 (bt, 1H), 3.08–3.22 (comp m, 4H), 3.75 (bm, 1H), 4.00 (d, 1H), 4.77 (bs, 1H), 5.08 (d, 2H), 5.67 (bs, 1H), 7.35 (comp m, 5H). Anal. Calcd. for $C_{36}H_{59}N_3O_6$: C, 68.65; H, 9.44; N, 6.67. Found: C, 68.52; H, 9.62; N, 7.03.

Preparation of Cbz amine 15 (V=—$OCH_3$)

To a solution of azide 14 (V=—$OCH_3$) (365 mg; 0.764 mmol) in degassed MeOH (3 mL) was added $NEt_3$ (424 μL; 4 equiv.) and 1,3-propanedithiol (306 μL; 4 equiv.) The reaction was stirred at rt under $N_2$ for 72 hours. The reaction was diluted in dry THF (4 mL) and $NEt_3$ (318 μL; 3 equiv.) and Cbz-hydroxysuccinimide (380 mg; 2 equiv.) were added. The mixture was stirred for 2 days and then diluted with EtOAc/$Et_2O$ and washed with 1N NaOH (3×) and brine. The organic was dried over anhydrous $MgSO_4$ and concentrated in vacuo. The product was purified by flash chromatography on a silica column eluting with Hex/EtOAc (7:1 to 5:1) to yield 408 mg (93%) of the title compound. $^1H$ NMR characteristic signals (300 MHz, $CDCl_3$) δ 1.50 (s, 9H), 2.61 (dt, 1H), 3.18 (q, 2H), 3.68 (s, 3H), 3.72 (bm, 1H), 3.95 (bd, 1H), 4.75 (bs, 1H), 5.10 (s, 2H) 7.35 (comp m, 5H).

Preparation of dipeptide 16 (V=—NH-2(S)-methylbutyl)

To Cbz amine 15 (V=—NH-2(S)-methylbutyl) (168 mg; 0.267 mmol) was added sat'd HCl/MeOH (2 mL). The mixture stood at rt for 1.5 hours and then was concentrated in vacuo. The HCl salt was dried over $P_2O_5$/KOH overnight at high vacuum. The next day the salt was dissolved in $CH_2Cl_2$ (1.5 mL) and $NEt_3$ (75 μL; 2 equiv). To this solution cooled to 0° C. was added α-Boc-γ-benzyl glutamic acid (180 mg; 2 equiv.) HOBT (108 mg; 3 equiv.) and EDC (77 mg; 1.5 equiv.). The reaction was stirred and allowed to warm to rt. After 2 days the mixture was diluted with EtOAc/$Et_2O$ and washed with 0.5N HCl, 1.0N NaOH and brine. The organic was dried over anhydrous $MgSO_4$ and concentrated in vacuo. The product was purified by flash chromatography on a silica column eluting with Hex/EtOAc (1:1.5) to yield 158 mg (73%) of the title compound. $^1H$ NMR characteristic signals (300 MHz, $CDCl_3$) δ 0.78–0.95 (comp, 7H), 1.48 (s, 9H), 2.52 (comp m, 2H), 2.93 (comp m, 1H), 3.12–3.35 (comp, 4H), 3.62 (bt, 1H), 3.92 (m, 1H), 3.97 (m, 1H), 4.93 (bs, 1H), 5.08 (s, 2H), 5.13 (s, 2H), 5.52 (bd, 1H), 6.41 (d, 1H), 7.03 (bs, 1H), 7.35 (comp m, 5H).

Preparation of dipeptide 16 (V=—$OCH_3$)

To Cbz amine 15 (V=—$OCH_3$) (408 mg; 0.7108 mmol) was added sat'd HCl/MeOH (ca. 5 mL). The mixture stood at rt for 7 hours and then was concentrated in vacuo. The HCl salt was dried over $P_2O_5$/-KOH overnight at high vacuum. The next day the salt was dissolved in $CH_2Cl_2$ (3 mL) and $NEt_3$ (200 μL; 2 equiv). To this solution cooled to 0° C. was added α-Boc-γ-benzyl glutamic acid (479 mg; 2 equiv.), HOBT (192 mg; 2 equiv.) and EDC (271 mg; 2 equiv.). The reaction was stirred and allowed to warm to rt. After 24 hours the mixture was diluted with EtOAc/$Et_2O$ and washed with 0.5N HCl, 1.0N NaOH and brine. The organic was dried over anhydrous $MgSO_4$ and concentrated in vacuo. The product was purified by flash chromatography on a silica column eluting with Hex/EtOAc (1.5:1) to yield 402 mg (77%) of the title compound. $^1H$ NMR characteristic signals (300 MHz, $CDCl_3$) δ 0.89 (comp m, 2H), 1.50 (s, 9H), 2.50 (comp, 3H), 3.14 (comp m, 2H), 3.62 (s, 3H), 3.71 (m, 1H), 3.89 (m, 1H), 4.11 (m, 1H), 4.92 (bt, 1H), 5.08 (s, 2H), 5.12 (s, 2H), 5.35 (d, 1H, 0, 6.39 (d, 1H), 7.32 (comp m, 5H).

Preparation of macrocycle 17 (V=—NH—2(S)-methylbutyl

To a solution of dipeptide 16 (V=—NH—2(S) -methylbutyl) (158 mg; 0.196 mmol) in MeOH (10 mL) was added 10% Pd on carbon (40 mg). The mixture was hydrogenated at 40 psi for 6 hours and then filtered through a pad of celite. The filtrate was concentrated in vacuo to yield 92 mg (80%) of crude amino acid. The crude amino acid was dissolved in dry DMF (90 mL) and cooled to 0° C. under $N_2$. To this solution was added $Et_3N$ (110 μL; 5 equiv.) and DPPA (170 μL 5 equiv.). After stirring at 0° C. for 20 minutes the reaction was placed in the cold room (4° C.) for 5 days. The DMF was then removed under high vacuum and the residue was taken up in EtOAc and washed with $H_2O$ and brine solution. The organic was dried over anhydrous $MgSO_4$ and concentrated in vacuo. The product was purified by flash chromatography on a silica column eluting with $CH_2Cl_2$/MeOH (20:1) to yield 68.5 mg (62%) of the title compound. $^1H$ NMR characteristics signals (300 MHz, $CDCl_3$) δ 0.74–0.98 (comp, 7H), 1.48 (s, 9H), 2.08 (comp, 3H), 2.35 (comp, 4H), 3.07 (comp m, 2H), 3.21 (comp m, 1H), 3.58 (bd, 2H), 3.83 (m, 1H), 4.15 (bm, 1H), 4.33 (bs, 1H0, 5.64 (bd, 1H), 5.90 (s, 1H), 6.18 (bd, 1H), 7.47 (bt, 1H); FAB mas spectrum, m/e 567 (m+H, calcd for $C_{30}H_{54}N_4O_6$, 567).

Preparation of macrocycle 17 (V=—$OCH_3$)

To a solution of dipeptide 16 (V=—$OCH_3$) (402 mg; 0.534 mmol) in MeOH (30 mL) was added 10% Pd on carbon (111 mg). The mixture was hydrogenated at 40 psi 6 hours and then filtered through a pad of celite. The filtrate was concentrated in vacuo to yield 287 mg (100%) of crude amino acid. The crude amino acid was dissolved in dry DMF (310 mL) and cooled to 0° C. under $N_2$. To this solution was added $NEt_3$ (377 μL; 5 equiv.) and DPPA (584 μL; 5 equiv.). After stirring at 0° C. for 20 minutes the reaction was placed in the cold room (4° C.) for 5 days. The DMF was then removed under high vacuum and the residue was taken up in EtOAc and washed with $H_2O$ and brine solution. The organic was dried over anhydrous $MgSO_4$ and concentrated in vacuo. The product was purified by flash chromatography on a silica column eluting with $CH_2Cl_2$/MeOH (25:1) to yield 172 mg (62%) of the title compound. $^1H$ NMR characteristic signals (300 MHz, $CDCl_3$) δ 0.79–0.99 (comp, 3H), 1.51 (s, 3H), 2.63 (bt, 1H), 3.72 (s, 3H), 3.91 (bd, 1H), 3.98 (bq, 1H), 4.31 (bs, 1H), 5.37 (d, 1H), 6.73 (d, 1H), 6.81 (d, 1H); FAB mas spectrum, m/e 512 (m+H, calcd for $C_{26}H_{45}N_3O_7$, 512).

Preparation of acid 17 (V=—OH)

To a solution of macrocycle 17 (V=—$OCH_3$) (32 mg; 0.0626 mmol) in MeOH (2.5 mL) cooled to 0° C. was added 1.0N NaOH (2 mL). After stirring at 0° C. for 1 hour the mixture was warmed to rt and stirred an additional 5 hours. The mixture was diluted with EtOAc and washed with 0.5N HCl and brine. The organic was dried over anhydrous $MgSO_4$ and concentrated in vacuo to yield 24 mg (77%) of the title compound. $^1H$ NMR characteristic signals (300 MHz, $CDCl_3$) δ 0.79–0.99 (comp, 3H), 1.49 (s, 9H), 3.73 (comp m, 4H), 3.98 (m, 1H), 4.61 (bs, 1H), 5.21 (bd, 1H), 7.10 (bs, 1H), 7.45 (bm, 1H); FAB mass spectrum m/e 498 (m+H, calcd for $C_{25}H_{43}N_3O_7$, 498).

Preparation of macrocycle 18-2 (V=—NH—2(S)-methylbutyl

To macrocycle 17 (V=—NH-2(S)-methylbutyl) (4.6 mg; 0.0083 mmol) was added sat'd HCl/MeOH (1 mL). After stirring for 1 hour the solvent was removed in vacuo. The resultant HCl salt was dried over $P_2O_5$/-KOH overnight at high vacuum. The salt was then dissolved in $CH_2Cl_2$ (1 mL) and $Et_3N$ (3.5 μL; 3 equiv.) and cooled to 0° C. under $N_2$. To this solution was added HOBT (5.6 mg; 5 equiv.), Boc-Phe (4.4 mg; 2 equiv.) and EDC (3 mg; 2 equiv.). The mixture was allowed to warm to rt and stirred overnight. The reaction was then diluted with EtOAc/$Et_2O$ and washed with 0.5N HCl, 1.0N NaOH and brine. The organic was dried over anhydrous $MgSO_4$ and concentrated in vacuo. The product was purifid by flash chromatography on a silica column eluting with $CH_2Cl_2$/MeOH (80:2 to 80:4) to yield 4.2 mg (72) of the title compound. $^1H$ NMR characteristic signals (300 MHz, $CDCl_3$) δ 0.73–0.98 (comp, 7H, 1.42 (s, 9H), 2.03 (comp m, 2H), 2.25 (bd, 4H), 2.96–3.10 (comp, 5H), 3.23 (bm, 1H), 3.55 (bt, 1H), 3.81 (bs, 1H), 4.32 (bq, 1H), 4.51 (bs, 1H), 5.09 (bd, 1H), 5.86 (bt, 1H), 6.05 (d, 1H), 7.08 (bs, 1H), 7.18–7.32 (comp, 5H), 7.38 (bs, 1H); FAB mas spectrum, m/e 714 (m+H, calcd for $C_{39}H_{63}N_5O_7$, 714).

Preparation of inhibitor 18-1 (V=—$OCH_3$)

To macrocycle 17 (V=—$OCH_3$) (14 mg; 0.0274 mmol) was added sat'd HCl/MeOH (2 mL). After stirring for 5 hours the solvent was removed in vacuo. The resultant HCl salt was dried over $P_2O_5$/KOH overnight at high vacuum. The salt was then dissolved in $CH_2Cl_2$ (1 mL) and $Et_3N$ (8 μL; 3 equiv.) and cooled to 0° C. under $N_2$. To this solution was added HOBT (7 mg; 2 equiv.), $N^{\alpha}$-Boc-Phe (15 mg; 2 equiv.) and EDC (11 mg; 2 equiv.). The mixture was allowed to warm to rt and stirred overnight. The reaction was then diluted with EtOAc/$Et_2O$ and washed with 0.5N HCl, 1.0N NaOH and brine. The organic was dried over anhydrous $MgSO_4$ and concentrated in vacuo. The product was purified by flash chromatography on a silica column eluting with $CH_2Cl_2$/MeOH (25:1) to yield 15.5 mg (86%) of the title compound. $^1H$ NMR characteristic signals (300 MHz, $CDCl_3$) δ 0.83–0.98 (comp, 3H), 1.40 (s, 9H), 3.75 (s, 3H), 4.33 (m, 1H), 4.56 (m, 1H), 4.99 (m, 1H), 6.82 (bs, 2H), 6.96 (bs, 1H), 7.12–7.32 (comp, 5H); FAB mass spectrum, m/e 659 (m+H, calcd for $C_{35}H_{54}N_4O_8$, 659).

Preparation of Macrocycle 18-3

The carboxylic acid prepared by treatment of 3 with lithium hydroxide and hydrogen peroxide is esterified by treatment with diazomethane, yielding 4 (V=—$OCH_3$). Procedures similar to those described above are then used to prepare 17 (V=—$OCH_3$). Saponification of ester 10 (V=—$OCH_3$) yields the corresponding carboxylic acid 17 (V=—OH) which is coupled with isopropanol to afford 17 [V=—O-i-Pr]. The Boc protecting group is then removed this ester by treatment with anhydrous TFA, and the resulting amino analog is coupled with N-(quinuclidin-3(S)-yl)-phenylalanine (27S) using conditions similar to those described above to provide the title compound.

Preparation of Macrocycle 18-4

Using the procedures described above and replacing isopropanol with N-(2-aminoethyl)morpholine, the title compound may be prepared.

Preparation of Macrocycle 18-6

Using the procedures described above and replacing isopropanol with N-(2-hydroxyethyl)morpholine, the title compound may be prepared.

Preparation of Macrocycle 18-8

Using the procedures described above and replacing isopropanol with isobutanol and replacing N-(quinuclidin-3(S)-yl)-phenylalanine with 2(S)-(t-butylsulfonyl)-methyl-3-phenylpropionic acid, the title compound may be prepared.

Preparation of Macrocyclic Renin Inhibitors of Formula I in which D=—OCO—, W=—NH—, s=0, n=0 and t=4

Scheme III illustrates the preparation of macrocylic renin inhibitors of formula I in which D=—OCO—, W=—NH—, s=0, n=0 and t=4. As shown in Scheme III, a 2-substituted ACHPA, protected as the acetonide derivative (21; V=—OH) is converted to amide or ester derivatives 21 using standard procedures for amide or ester formation. As shown in Scheme III, the olefinic side chain of the resulting analog 21 is transformed to yield the carboxylic acid derivative 22. Esterification of 22 with a protected analog of serine provides the macrocyclization precursor 23, which is then cyclized to macrocycle 24. After removal of the Cbz protecting group from 24, the resulting amino derivative is coupled with carboxylic acids, acid chlorides, or sulfonyl chlorides using standard coupling procedures to yield macrocycles such as 25.

SCHEME III

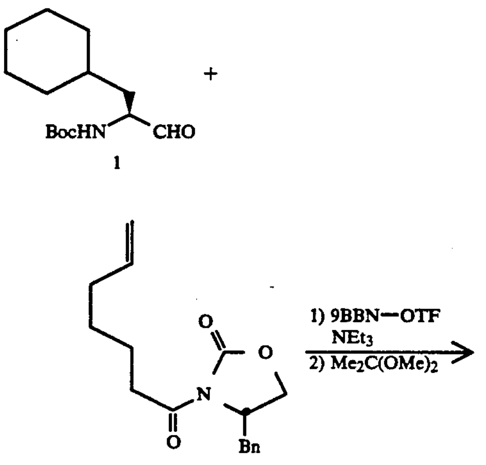

1

+

19

-continued
SCHEME III

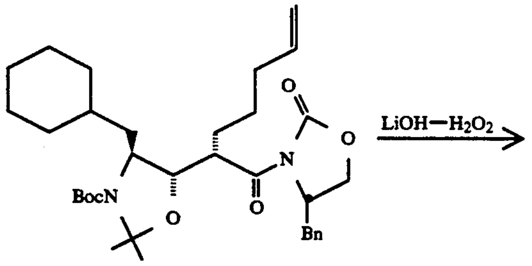

20

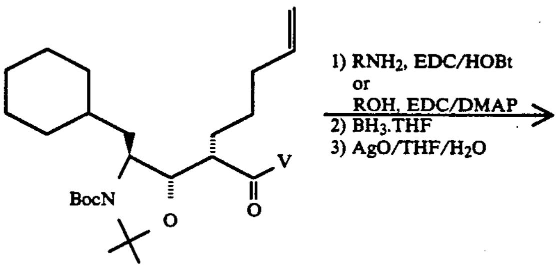

21

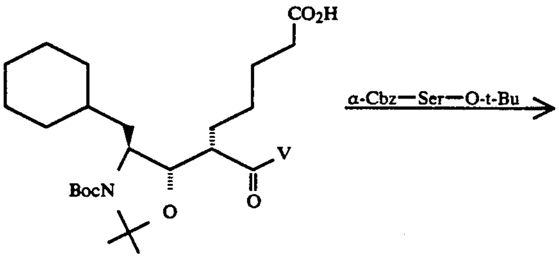

22

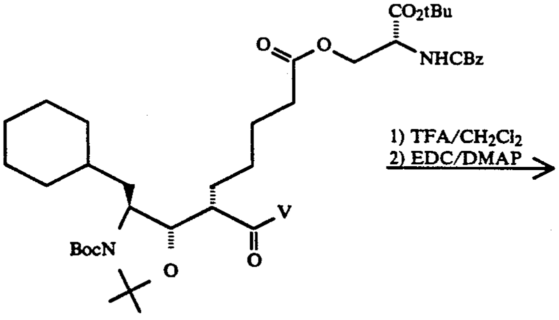

23

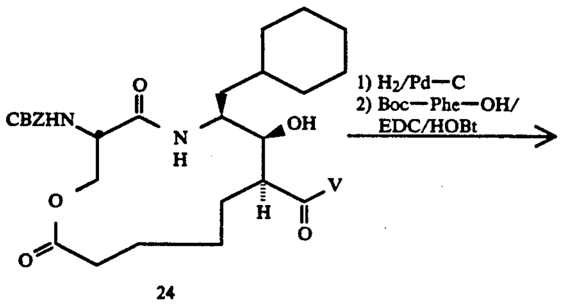

24

-continued
SCHEME III

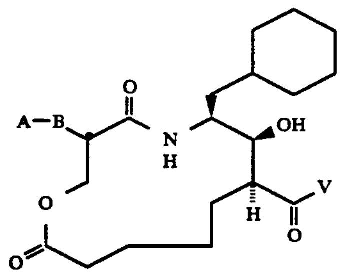

25

Preparation of Macrocycle 25-1

According the route outlined in Scheme III, ester 21 (V=—O-i-Pr) may be prepared from acid 21 (V=—OH) using isopropanol. This ester may then be transformed to macrocycle 24 (V=—O-i-Pr) as shown. Removal of the Cbz protecting group as shown, and coupling of the resulting amino analog with Boc-Phe as illustrated yields macrocycle 25-1.

Preparation of Macrocycle 25-2

According the route outlined in Scheme III, amide 21 (V=—NH—2(S)-methylbutyl) may be prepared using 2(S)-methylbutylamine. This amide may then be transformed to macrocycle 24 (V=—NH—2(S)-methylbutyl) as shown. Removal of the Cbz protecting group from 24, and coupling of the resulting amino analog with Boc-Phe as illustrated yields macrocycle 25-2.

Preparation of Macrocycle 25-5

According the route outlined in Scheme III, amide 21 (V=—O-i-Pr) may be prepared using isopropanol. This ester may then be transformed to macrocycle 24 (V=—O-i-Pr) as shown. Removal of the Cbz protecting group from 24, and coupling of the resulting amino analog as illustrated in Scheme III with N-(quinuclidin-3(S)-yl)phenylalanine dihydrochloride (27S) yields the title compound.

Preparation of Macrocycle 25-6

According the route outlined in Scheme III, amide 21 [V=—O—$CH_2CH_2$(morpholin-4-yl)] may be prepared using N-(2-hydroxyethyl)morpholine. This ester may then be transformed to macrocycle 24 [V=—O-$CH_2CH_2$(morpholin-4-yl)] as shown. Removal of the Cbz protecting group from 24, and coupling of the resulting amino analog as illustrated with N-(quinuclidin-3(S)-yl)phenylalanine (27S) yields the title compound.

Preparation of Macrocycle 25-7

According the route outlined in Scheme III, amide 21 [V=—O-$CH_2CH_2$(N-methylmorpholin-4-yl)+ $Cl^-$] may be prepared using N-(2-hydroxyethyl)-N-methylmorpholinium chloride. This ester may then be transformed to macrocycle 24 [V=—O-$CH_2CH_2$(N-methylmorpholin-4-yl)+ $Cl^-$] as shown. Removal of the Cbz protecting group from 24, and coupling of the resulting amino analog as illustrated with 2-[(morpholin-4-yl)carbonyl]methyl-3-phenylpropionic acid yields the title compound.

Preparation of Macrocycle 25-8

According the route outlined in Scheme III, amide 21 [V=—O-$CH_2CH_2$(morpholin-4-yl)] may be prepared using N-(2-hydroxyethyl)morpholine. This ester may then be transformed to macrocycle 24 [V=—O—$CH_2CH_2$(morpholin-4-yl)] as shown. Removal of the Cbz protecting group from 24, and coupling of the resulting amino analog with 2(S)-(t-butylsulfonyl)methyl-3-phenylpropionic acid as illustrated yields the title compound.

N$^{\alpha}$-(Quinuclidin-3(RS)-yl)-Phe-t-butyl ester hydrochloride (26)

To a solution of 9.00 g (56.25 mmol) 3-quinuclidinone and 4.15 g (18.75 mmol) Phe-O-t-Bu in 50 ml methanol was added over a 12 hour period a solution of 2.95 g (46.9 mmol) sodium cyanoborohydride in 13 ml methanol. After stirring for an additional 8 hours, 5.78 g (50.0 mmol) pyridine hydrochloride was added and after 1½ hours stirring, sodium chloride was removed by filtration. The filtrate was concentrated to a foam which was treated with 15 ml methanol and 50 ml ethyl acetate to give a slurry of the byproduct 3-hydroxy quinuclidine hydrochloride (74% of excess) which was removed by filtration. The filtrate was concentrate to an oil and charged with 10 ml methanol to a 5×200 cm column of LH-20 and eluted with methanol. The product fraction contained 6.54 g of a mixture of diastereomers in a 55:45 ratio as established by HPLC.

N$^{\alpha}$-(Quinuclidin-3(S)-yl)-Phe-t-butyl ester hydrochloride (26S)

A solution of 7.0 g of the isomer mixture (from Example 1) in 25 ml water was treated with 2.62 g sodium bicarbonate bringing the pH to 9.0. The clear solution was lyophilized and the crystalline residue was extracted with 50 ml of acetonitrile. Evaporation of the solvent and treatment with 25 ml ether gave crystals which were filtered off, washed with ether, and dried. The yield was 2.49 g (65%) of an isomer established by x-ray crystal structure analysis to be the S,S-diastereomer hydrochloride.

N$^{\alpha}$-(Quinuclidin-3(S)-yl)Phe-O-t-Bu.2 HCl (27S)

A solution of 1.91 g of the 4S in 3 ml concentrated hydrochloric acid was left for 3 hours and then concentrated to an amorphous mass. To remove excess HCl the material was redissolved in 10 ml water and concentrated to yield 1.98 g of the dihydrochloride.

[N$^{\alpha}$-(N-Methylquinuclidin-3(S)-yl)Phe-O-t-Bu]$^{\pm}$I$^{-}$ (28S)

A solution of 4S in 2 ml methanol was treated with 310 μl. (5.0 mmol) methyl iodide and 68.3 mg (1.26 mmol) sodium methylate. After 2 hours at room temperature the reaction mixture was concentrated and charged with 4 ml of methanol to a 2.5×210 cm column of LH-20 and eluted with methanol. The product fractions contained 366 mg of product with an NMR spectrum consistent with the assigned structure.

N$^{\alpha}$-[(N-Methylquinuclidin-3(S)-yl)-phenylalanine]$^{+}$ Cl$^{-}$.HCl (29S)

A solution of 366 mg (775 μM) of 28S in 1 ml of water and 2 ml of conc. hydrochloric acid was aged for 2 hours, concentrated and charged with 2 ml methanol to 2.5×210 cm LH20 column and eluted with methanol. The product fraction contained 254 mg of product with NMR and mass spectra consistent with the structure.

N$^{\alpha}$-(Quinuclidin-3(RS)-yl)Nal-$OCH_3$.HCl (30)

A solution of 2.20 g (8.28 mmol) of 3-(1-Naphthyl)-Ala-$OCH_3$.HCl and 4.02 g (25 mmol) of 3-Quinuclidinone hydrochloride in 30 ml of methanol was treated over the course of 11 hours with a solution of 1.20 g (20.7 mmol) of sodium cyanoborohydride in 7.5 ml of methanol. After the addition was complete the reaction mixture was allowed to stir for 4 days and then treated with 2.42 g (20.9 mmol) pyridine hydrochloride and after stirring for 3 hours, the solvent was removed using a rotary evaporator. The residue was stirred with 10 ml methanol and the insoluble sodium chloride was removed by filtration and washed with 5 ml methanol. The filtrate was treated with 60 ml ethyl acetate and the solution was seeded with 3-RS-quinuclidinol hydrochloride. The alcohol byproduct was removed by filtration and the filtrate was concentrated in vacuum to an oil. A second crop of this byproduct was removed by crystallization with a solvent mixture consisting of 50 ml ethyl acetate, 50 ml of acetonitrile, and 2 ml of methanol. The filtrate was concentrated in vacuo to 5.36 g of an amorphous residue. This was dissolved in 5 ml of methanol and chromatographed over a 5×200 cm column of LH-20 eluting with methanol. The product-containing fractions were combined and concentrated, yielding 4.4 g of product.

N$^{\alpha}$-(Quinuclidin-3(S)-yl)Nal-$OCH_3$.HCl (30S)

Using mixtures of acetonitrile and ether for crystallization, a total of 440 mg of the 3(S)-diastereomer was obtained from the above mixture (30)

N$^{\alpha}$-(Quiniclidin-3(RS)-yl)Nal-OH dihydrochloride (31)

N$^{\alpha}$-(Quiniclidin-3(RS)-yl)Nal-Ome.HCl (0.5 g) (30) was dissolved in 6N HCl (10 ml), and the mixture was refluxed for 4 hours and then allowed to stand at room temperature overnight. The mixture was then concentrated in vacuo to dryness, and the residue was dried in a vaccum descicator over NaOH and dryness, and the residue was dried in a vacuum descicator over NaOH and $P_2O_5$ overnight to give the desired product as a foam (0.55 g). $^1$H NMR (300 MHz, $CD_3OD$): d 1.9–2.2 (m, 3H), 2.45 (m, 2H), 3.16–3.95 (m. 7H), 4.2–4.5 (m, 3H), 7.35–7.7 (m, 4H), 7.88 (dd, 2H), 8.3 (d, 1H), MS(FAB): m/e 325 (MH+).

N$^{\alpha}$-(2,2,6,6-Tetramethylpiperidin-4-yl)-Phe-O-t-Bu (31)

A solution of 11.55 g (60.2 mmol) 2,2,6,6-tetramethylpiperidin-4-one hydrochloride and 4.44 g (20 mmol) Phe-O-t-Bu in 40 ml of methanol was treated over an eight hour period with a solution of 3.19 g (50.8 mmol) sodium cyanoborohydride in 6 ml of methanol. After stirring overnight a solution of 8.21 g (71.0 mmol) pyridine hydrochloride in 20 ml of methanol was added and stirring continued for 1½ hour. Sodium chloride was removed by filtration, and the filtrate was concentrated to an oil. The byproduct 2,2,6,6-tetramethylpiperidin-3-ol (69.5% of excess) crystallized on addition of 40 ml ethyl acetate and 40 ml of acetonitrile, and was removed by filtration. The filtrate was concentrated to an amorphorus mass which was charged with 10 ml methanol to a 5×200 cm LH-20 column and eluted with methanol. Evaporation of the solvent from the product-containing fractions and crystallization from 10 ml acetonitrile afforded 5.34 g (61.5%) of product, which had NMR and mass spectra in accord with assigned structure.

$N^{\alpha}$-(1-Ethylpiperidin-3(RS)-yl)Phe-O-t-Bu (32)

A solution of 8.18 g (50.0 mmol) 1-ethyl-3-piperidone HCl, 5.15 g (20.0 mM) Phe-O-t-Bu and 1.64 g (19.3 mM) sodium acetate in 250 ml methanol was treated over a 14 hour period with a solution of 1.88 g (30.0 mmol) sodium cyanoborohydride in 10 ml methanol. After stirring overnight, 3.47 g (30.0 mmol) pyridine hydrochloride was added, and after 2 hour stirring sodium chloride was removed by filtration and the reaction mixture was concentrated to an oil. This was dissolved in 16 ml methanol and chromatographed on a 5×200 cm LH-20 column eluted with methanol. The product fraction contained 4.01 g (67.2%) of a mixture of diastereomers with NMR and mass spectra in accord with the assigned structure.

Methyl 2-Hydroxy-3-phenylpropionate (33)

To a stirred solution of Phenylalanine (16.5 g, 0.1 mole) in 2N sulfuric acid at 0° C., was added sodium nitrite (10.5 g, 1.5 equiv) in small portions over a period of 0.5 hours and the mixture stirred overnight. Aqueous phase was extracted with ether (5×250 mL) and the ethereal extracts were washed with saturated aqueous solution of sodium chloride, dried over anhydrous magnesium sulfate and concentrated to give phenyllactic acid (1 equiv) in methanol (15 equiv) at 0° C. and the mixture stirred at room temperature overnight. Removal of volatiles in vacuo and chromatographic purification of the oil (20–25% ethyl acetate in hexane) gives methyl 2-hydroxy-3-phenylpropionate (11). $^1H$ NMR (300 MHz, $CDCl_3$): δ 7.33–7.196 (m, 5H), 4.451 (dd, 1H), 3.764 (s, 3H), 3.1225 (dd, 4.45 Hz, 13.95 Hz, 1H), 2.9575 (dd, 7 Hz, 14 Hz, 1H), 2.787 (br s, 1H).

Methyl 2-Methanesulfonyloxy-3-phenylpropionate (34)

A dichloromethane solution of methyl 2-hydroxy-3-phenylpropionate (33) is treated with triethylamine (1.1 equiv) and methanesulfonyl chloride (1.1 equiv) at 0° C. Upon completion of reaction, the mixture is dissolved in dichloromethane/ether and washed with saturated aqueous solution of sodium chloride, dried and concentrated. Purification of crude material by flash column chromatography (40% ethyl acetate in hexane) gives methyl 2-methanesulfonyloxy-3-phenylpropionate (1.6 g, 93%). $^1H$ NMR (300 MHz $CDCl_3$): δ 7.358–7.233 (m, 5H), 5.173 (dd, 4.26 Hz, 8.8 Hz, 1H), 3.793 (s, 3H), 3.301 (dd, 4.23 Hz, 14.38 Hz, 1H), 3.1295 (dd, 8.8 Hz, 14.3 Hz, 1H), 2.766 (s, 3H).

3-Acetylthioquinuclidine (35)

To a THF (300 mL) solution of triphenyl-phosphine (42 g, 160 mmol, 2 equiv) at 0° C. was added diisopropyl azodicarboxylate (32 mL, 162 mmol) to produce a pale yellow solid. A THF (300 mL) solution of 3-quinuclidinol (10.2 g, 80.2 mmol) and thiolacetic acid was added dropwise to the yellow reaction mixture and stirred overnight. THF was removed in vacuo and the residue was dissolved in ether (500 mL) and extracted with 10% HCl (4×150 mL). The aqueous acidic phase was back extracted with ether/ethyl acetate (75 mL/25 mL) and then neutralized to pH 7 by the addition of sodium bicarbonate cautiously in small portions. The aqueous layer was then basified to pH 9–10 by adding a few drops of 10N NaOH, then extracted with dichlormethane (5×200 mL), dried over anhydrous sodium sulfate and concentrated. Purification by flash column chromatrography using 5% MeOH in chloroform as eluent gave 3-acetylthioquinuclidine (10.5 g, 71%). $^1H$ (300 MHz, $CDCl_3$): δ 3.725–3.63 (m, 1H), 3.427 (dd, 10.23 Hz, 13.7 Hz), 2.9–2.75 (dd, 4H), 2.678 (dd, 5.7 Hz, 14.2 Hz, 1H), 2.326 (S, 3H), 1.9–1.82 (m, 1H), 1.81–1.675 (m, 3H), 1.53–1.4 (m, 1H).

3-Mercaptoquinuclidine (36)

Acetylthioquinuclidine it treated with sodium methoxide in methanol. Upon completion of hydrolysis the sovent is removed in vacuo to obtain 3-mercaptoquinclidine which is used in the next step without further purification.

2-(Quinuclidin-3-yl)thio-3-phenylpropionic acid: (37)

To a stirred solution of 3-mercaptoquinuclidinol in DMF at 0° C. is added sodium hydride (1 equiv) and the mixture stirred for 0.5 hours. A solution of methyl-2-methanesulfonyloxy-3-phenylpropionate (1 equiv) in DMF or THF is added to the reaction mixture at 0° C. and the resulting mixture stirred. After completion of reaction, methanol is added dropwise to quench the reaction. The volatiles are removed in vacuo and the residue is purified by flash chromatography to obtain the methyl ester which is sponified with aqueous sodium hydroxide (1N, 1 equiv) in methanol to afford 2-(quinuclidin-3-yl)thio-3-phenylpropionic acid.

2-(Quinuclidin-3-yl)oxy-3-phenylpropionic acid (38)

To a slurry of potassium hydride (1 equiv) in THF at 0° C. is added 3-quinuclidinol (1 equiv) and the mixture stirred for 0.25 hours. A THF solution of methyl-2-methanesulfonyloxy-3-phenylpropionate (1 equiv) is added to the reaction mixture and stirred until completion of reaction. The reaction is quenched by slow addition of methanol, the mixture is concentrated and the residue is purified by flash chromatography to afford methyl ester which is treated with aqueous sodium hydroxide (1N, NaOH) to produce the 2-(quinuclidin-3-yl)oxy-3-phenylpropionic acid.

Methyl 2-Benzylacrylate (39)

Methyl 2-benzylacrylate is prepared by the method of J. Harley-Mason et al., Tetrahedron, 36, 1063 (1980).

Methyl-2-(quinuclidin-3-yl)thiomethyl-3-phenylpropionate(40)

3-Acetylthioquinuclidine is hydrolyzed to 3-mercaptoquinuclidine by treating with sodium methoxide in methanol. To the sodium salt of 3-metcaptoquinuclidine in methanol at 0° C., is added methyl 2-benzylacrylate and the mixture stirred for a few hours. Upon completion of reaction, methanol is removed and the residue is subjected to flash column chromatography to give title compound.

2-(Quinuclidin-3-yl)sulfonylmethyl-3-phenylpropionic acid (41)

Methyl-2-(quinuclidin-3-yl)thiomethyl-3-phenylpropionate is treated with 2 equivalents of m-chloro-peroxybenzoic acid in $CH_2Cl_2$. The reaction mixture is filtered to remove m-chloro-benzoic acid and the filtrate is concentrated. The residue is purified by flash chromatogrphy and then subjected to the action of 6N HCl-HOAc (1:1) at 60° C. for 24 hours, providing the title compound.

Preparation of Macrocyclic Renin Inhibitors of Formula I in which D=—CONH—, s=1, t=4, n=0, W=—O— and the V Element Comprises an ester:

Scheme IV illustrates the preparation of macrocyclic renin inhibitors of Formula I in which D=—CONH—, s=1, t=4, n=0, W=—O— and the V element comprises an ester. The carboxylic acid prepared by treatment of oxazolidinone 81 with LiOH and $H_2O_2$ is converted to a t-butyl ester by treatment with t-butylisourea. After cyclization to macrocycle 86, the FMOC protecting group is removed by treatment with diethylamine, and the resulting amino analog is coupled with Ac-Phe. Finally, treatment with aqueous acid removes the THP protecting group and hydrolyzes the t-butyl ester, and the resulting hydroxyacid is esterified using, for example, diazomethane, to afford macrocycle 87. Other carboxylic acids or sulfonyl chlorides may be used in place of Ac-Phe to prepare similar macrocycles. Likewise esterification may be carried with other alcohols, for example using isobutanol and DCC/DMAP.

SCHEME IV

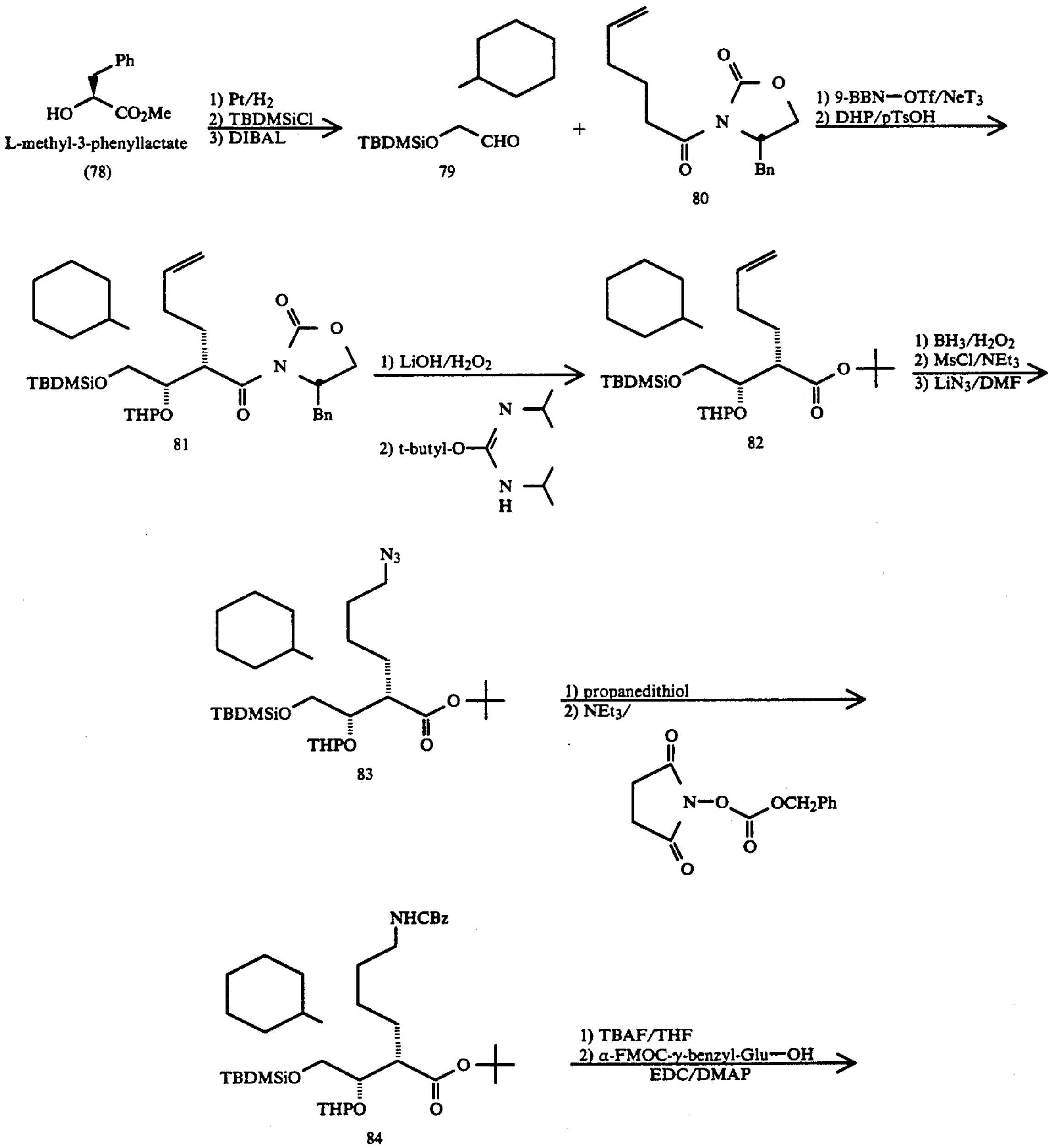

L-methyl-3-phenyllactate (78)
79
80
81
82
83
84

-continued

SCHEME IV

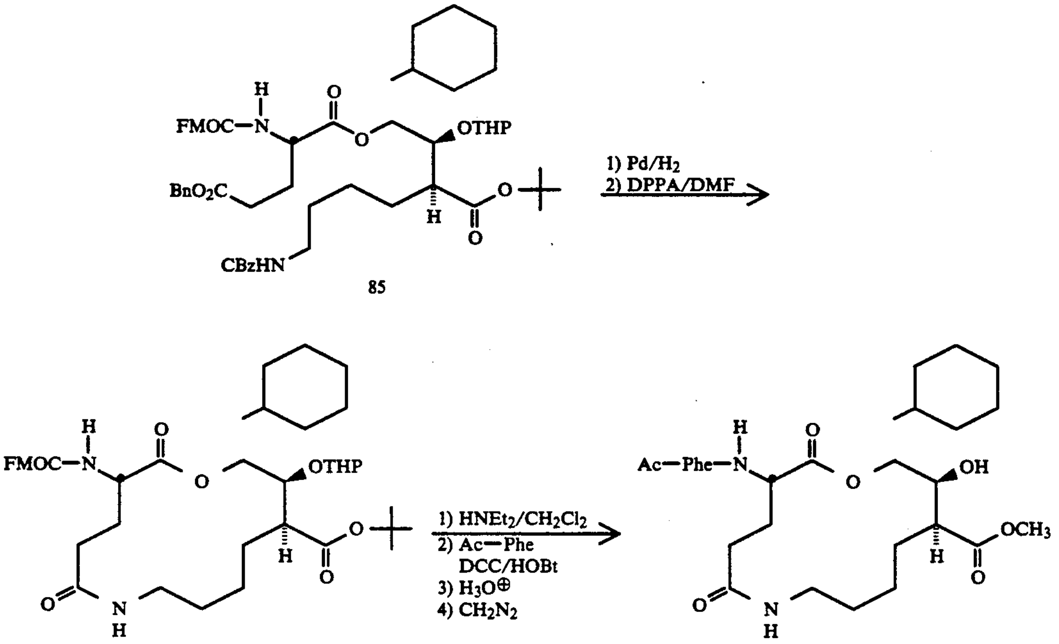

85

86

87

Preparation of Macrocyclic Renin Inhibitors of Formula I in which D=—CONH—, s=1, t=4, n=0, W=—O— and the V Element Comprises an Amide Scheme V illustrates the preparation of macrocyclic renin inhibitors of Formula I in which D=—CONH—, s=1, t=4, n=0, W=—O— and in which the V component comprises an amide. Treatment of oxazolidinone 81 with LiOH and $H_2O_2$ affords the corresponding carboxylic acid, which may be coupled with an amine such as n-butylamine, to form an amide such as 88. The amide is carried through the synthetic scheme as shown, yielding macrocycle 92. After removal of the THP and Boc protecting groups, the resulting amino derivative is acylated with Boc-Phe, yielding macrocycle 93. Other carboxylic acids or sulfonyl chlorides may be used in place of Boc-Phe to prepare similar macrocycles. Likewise n-butylamine may be replaced in this scheme with other primary and secondary amines.

SCHEME V

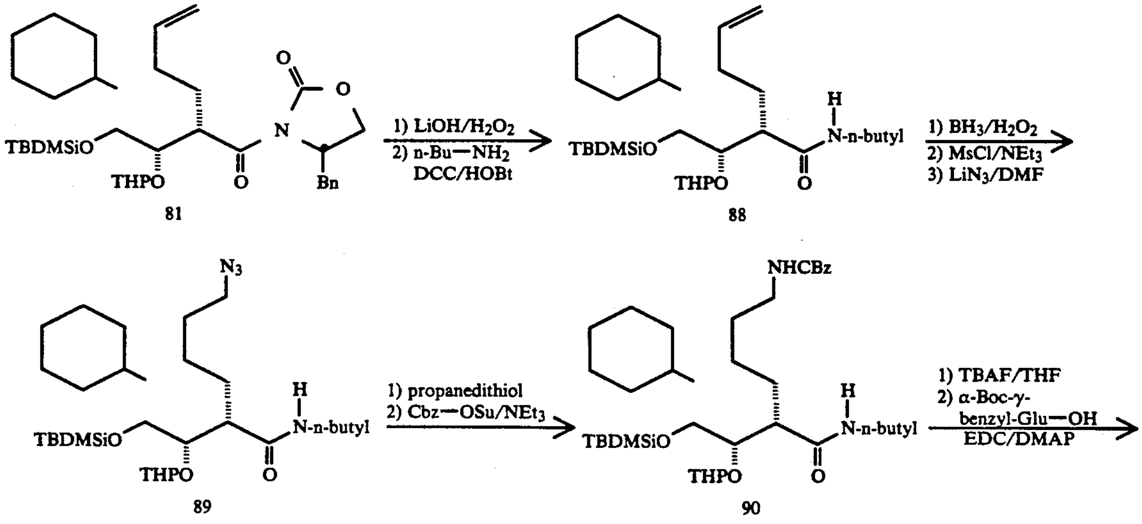

81

88

89

90

-continued

SCHEME V

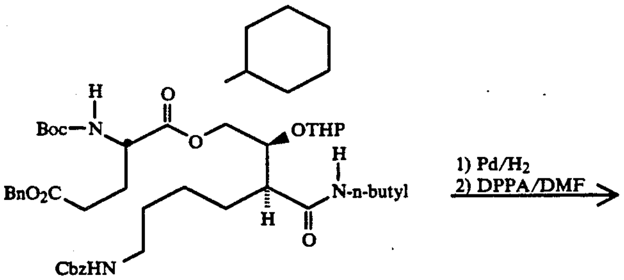

91

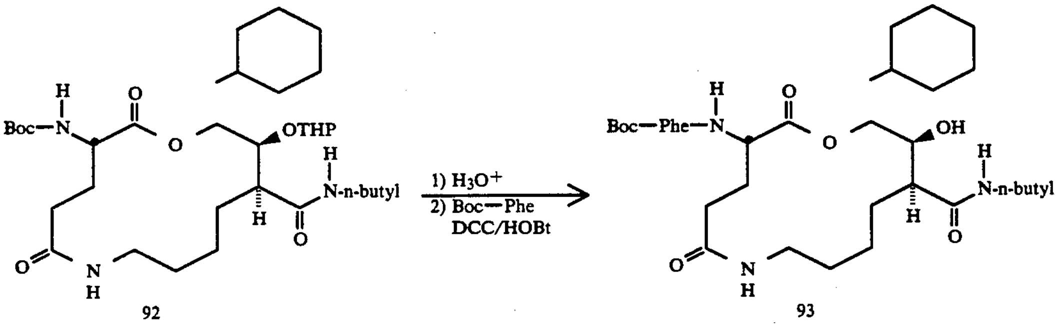

92 93

Preparation of Macrocyclic Renin Inhibitors of Formula I in which D=—OCO—, s=0, t=5, n=0, W=—O— and the V Element Comprises an Ester Scheme VI illustrates the preparation of macrocyclic renin inhibitors of Formula I in which D=—OCO—, s=0, t=5, n=0, W=—O— and the V element comprises an ester. The carboxylic acid prepared by treatment of oxazolidinone 104 with LiOH and $H_2O_2$ is converted to t-butyl ester 105 by treatment with t-butylisourea. After cyclization to macrocycle 108, the FMOC protecting group is removed by treatment with diethylamine, and the resulting amino analog is coupled with Ac-Phe. Finally, treatment with aqueous acid removes the THP group and the t-butyl ester, and the resulting hydroxyacid is esterified as shown, affording macrocycle 109. Other carboxylic acids or sulfonyl chlorides may be used in place of Ac-Phe to prepare similar macrocycles. Likewise esterification may be carried out with other alcohols to prepare macrocycles similar to 109.

SCHEME VI

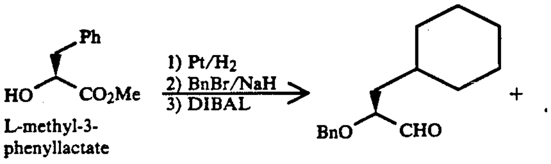

L-methyl-3-phenyllactate 78 79a

-continued

SCHEME VI

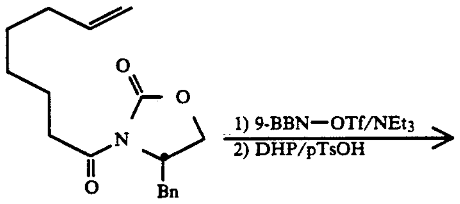

103

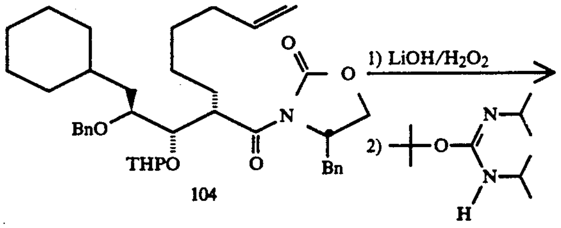

104

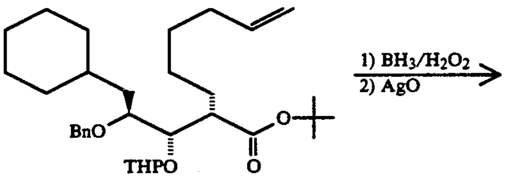

105

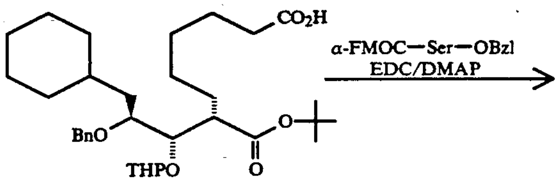

106

-continued

SCHEME VI

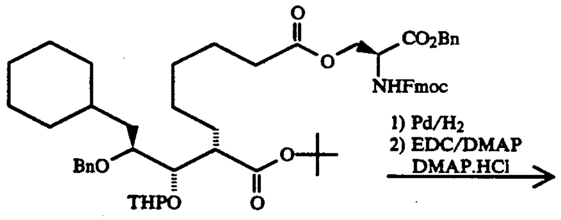

107

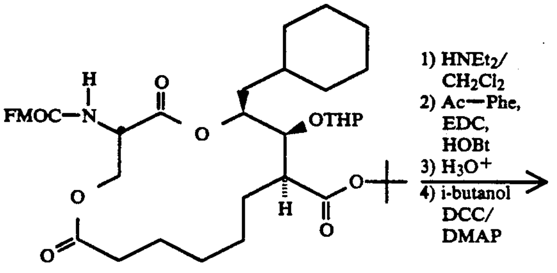

108

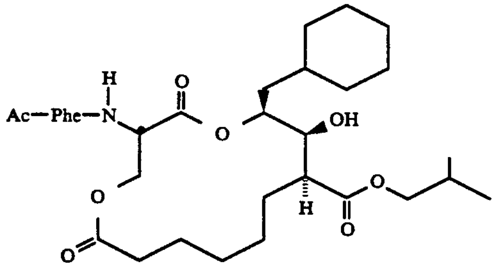

109

Preparation of Macrocyclic Renin Inhibitors of Formula I in which D=—OCO—, s=0, t=5, n=0, W=—O— and the V Element Comprises an Amide Scheme VII illustrates the preparation of macrocyclic renin inhibitors of Formula I in which D=—O-CO—, s=0, t=5, n=0, W=—O— and the V element comprises an amide. Treatment of oxazolidinone 104 with LiOH and $H_2O_2$ affords the corresponding carboxylic acid, which may be coupled with an amine such as n-butylamine, to form an amide such as 110. The amide is carried through the synthetic scheme as shown, yielding macrocycle 113. After removal of the THP protecting group by treatment with aqueous acid, the FMOC protecting group is removed by treatment with diethylamine, and the resulting amino derivative is acylated with Boc-Phe, yielding macrocycle 114. Other carboxylic acids or sulfonyl chlorides may be used in place of Boc-Phe to prepare similar macrocycles. Likewise n-butylamine may be replaced in this scheme with other primary and secondary amines.

SCHEME VII

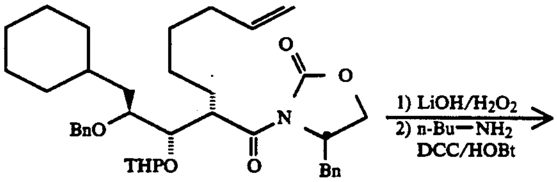

104

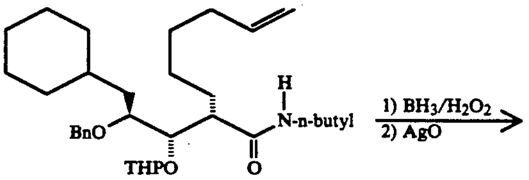

110

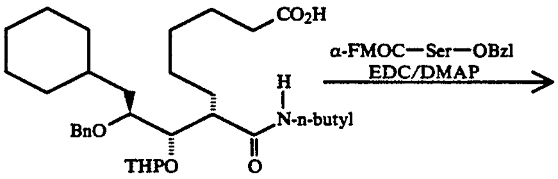

111

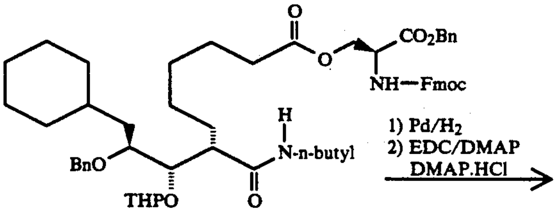

112

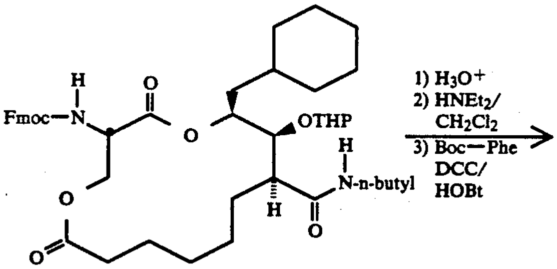

113

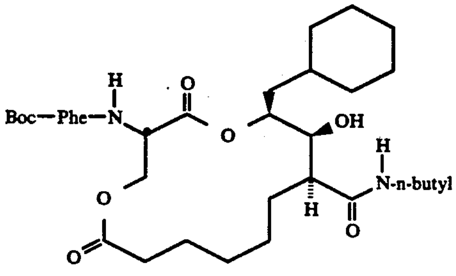

114

Preparation of Macrocyclic Renin Inhibitors of Formula I where D=—OCO—, s=0, t=4, n=0, W=0, and Z=—$OPO_3H_2$ Macrocyclic renin inhibitor of Formula I where D=—OCO—, s=0, t=4, n=0, W=0, and Z=—O-$PO_3H_2$ may be prepared by standard methods of phosphorylation starting from, for example, macrocycle 137. One method for phosphorylation is treatment of the macrocycle with dibenzylphosporochloridate and diisopropylethylamine (or pyridine) to afford a dibenzylphosphate ester, followed by removal of the benzyl esters by treatment with Pd/C and $H_2$. An alternative method which may be used to prepare phosphate derivatives of some macrocycles is treatment of the macrocycle with tetrabenzyl pyrophosphate, followed by deprotection by hydrogenolysis or by treatment with trimethylsilyl bromide (P. M. Chouinard et al, J. Org. Chem., 51, 75-78 (1986)).

Preparation of Macrocyclic Renin Inhibitors of Formula I where D=—OCO—, s=0, t=4, n=0, W=0, and Z is a derivatized hydroxyl group Macrocyclic Renin Inhibitors of Formula I where D=—OCO—, s=0, t=4, n=0, W=0, and Z is an esterified hydroxyl group may be prepared by standard methods of ester formation, starting from, for example, macrocycle 137. For example, treatment of 137 with acetic anhydride and pyridine affords macrocycle 143. Other carboxylic acids or acid chlorides may be used to prepare similar analogs using standard methods. These methods include treatment of a macrocycle such as 137 with a carboxylic acid and EDC/DMAP. It is understood that the carboxylic acid component may contain functional groups which require protection during the coupling step. These protections groups include Boc- or Cbz- for amines, and benzyl or t-butyl esters for carboxylic acid groups not involved in the coupling step. Table 11 shows examples of compound of Formula I which may be prepared using the routes described above.

Similar analogs in which Z is a carbonate group may be prepared as above using chloroformates in place of carboxylic acids.

Preparation of Macrocyclic Renin Inhibitors of Formula I in which D=—OCO—, W=—NH—, s=0, and t=5, n=0

Scheme VIII illustrates the preparation of macrocyclic renin inhibitors of the formula I in which D=—O-CO—, W=—NH—, s0, and t=5, n=0. As shown in Scheme VIII, a 2-substituted ACHPA acetonide derivative 140 (V=OH) is converted to an amide or ester derivative using standard procedures for amide or ester formation. The olefinic sidechain of the resultant analog 140 is transformed to carboxylic acid derivative 141. Esterification of 141 with a protected analog of serine provides the macrocycle precursor 142, which is then cyclized to macrocycle 143. After removal of the Cbz protecting group from 143, the resultant amino derivative is coupled with carboxylic acids, acid chlorides, or sulfonyl chlorides using standard coupling procedures to yield macrocycles such as 144.

SCHEME VIII

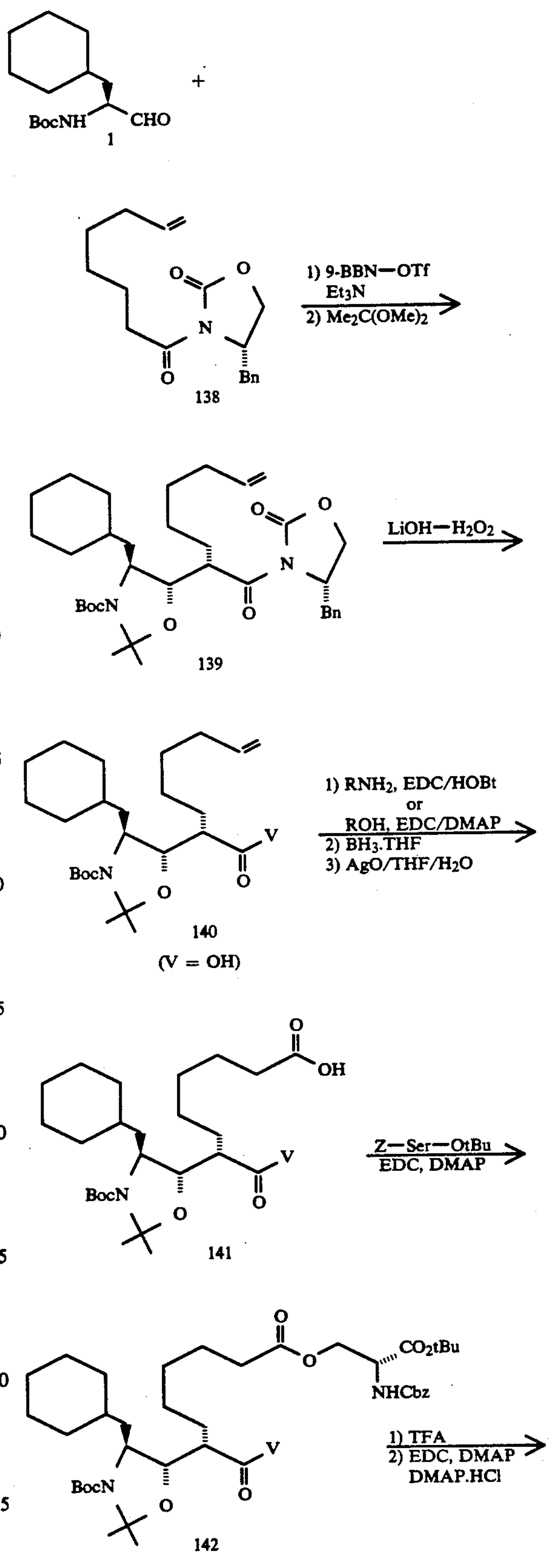

-continued

SCHEME VIII

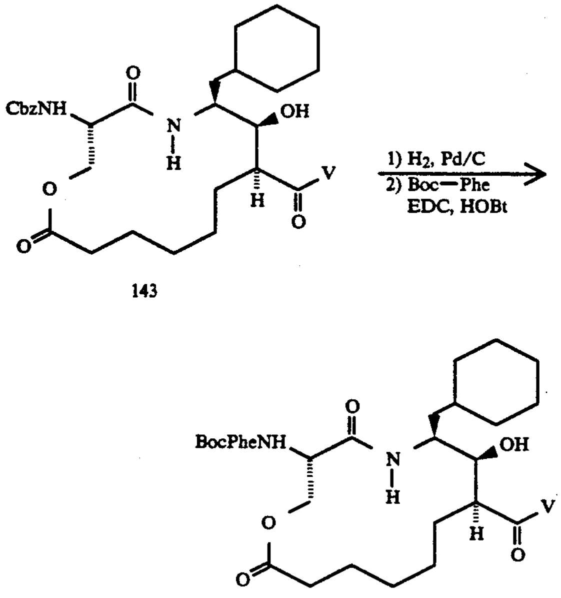

143

144

Preparation of Macrocyclic Renin Inhibitors of Formula I in which D=—OCO—, W=—NH—, s=0, t=5, n=0, and AB=an N-carboxyalkyl derivative Scheme IX illustrates the preparation of macrocyclic renin inhibitors of the formula I in which D=—O-CO—, W=—NH—, s=0, t=5, n=0, and AB=an N-carboxyalkyl derivative. As shown in Scheme IX, the Cbz group of macrocycle 143 is removed and the resultant amino derivative is reductively alkylated with a 2-keto ester using standard procedures to provide esters such as 143a. Ester 143a is converted to the corresponding acid and coupled with amines using standard coupling procedures to provide macrocycle amides such as 145.

SCHEME IX

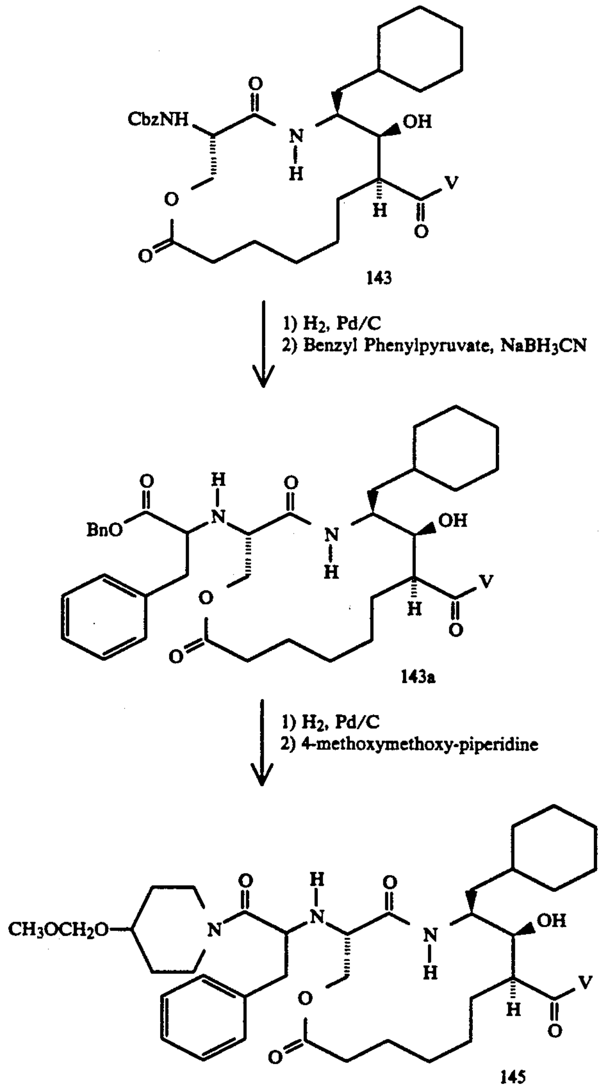

143

143a

145

Preparation of Macrocyclic Renin Inhibitors of Formula I in which D=—OCO—, W=—NH—, s=0, t=5, n=0, and AB=a carboxyalkoxy derivative Scheme X illustrates the preparation of macrocyclic renin inhibitors of the formula I in which D=—O-CO—, W=—NH—, s=0, t=5, n=0, and AB=a carboxyalkoxy derivative. As shown in Scheme X, acid 141 is converted to its benzyl ester 148 and the amino blocking group of benzyl ester 148 is then removed. The resultant amino derivative is coupled to acid 147 (prepared as shown) using standard coupling procedures to give macrocycle precursor 149. Deprotection and cyclization provides macrocycle 150. Removal of the t-butyl ester blocking group followed by coupling to an amine gives macrocycles such as 151.

SCHEME X

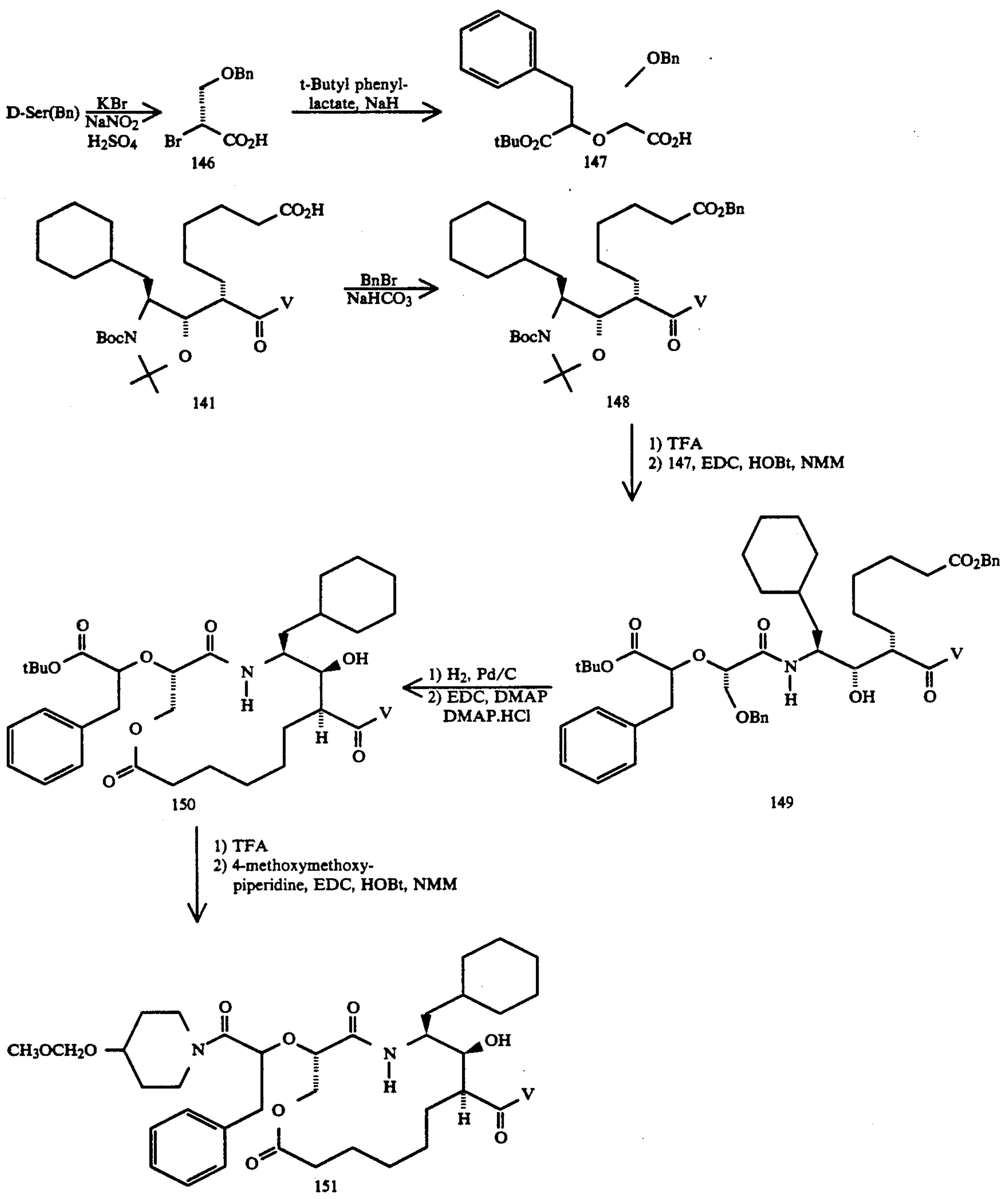

Preparation of Macrocyclic Renin Inhibitors of Formula I in which D=—OCO—, W=—NH—, s=0, t=4, and n=1

Scheme XI, XII, and XIII illustrate the preparation of macrocyclic renin inhibitors of the formula I in which D=—OCO—, W=—NH—, s=0, t=4, and n=1. As shown in Scheme XI, lactone 157 (prepared from Boc-Phe-OMe as shown) is opened with an aluminum amide reagent to give amide 158. Conversion to acid 159 following standard procedures followed by esterification with a protected serine derivative provides macrocycle precursor 160. Removal of the protecting groups and macrocyclization yields macrocycle 161. As shown in Scheme XI, after removal of the Cbz protecting group from 161, the resultant amino derivative is coupled with carboxylic acids, acid chlorides, or sulfonyl chlorides using standard coupling procedures to yield macrocycles such as 162. As shown in Scheme XII, the Cbz group of macrocycle 161 is removed and the resultant amino derivative is reductively alkylated with a 2-keto ester using standard procedures to provide esters such 163. Ester 163 is converted to the corresponding acid and coupled with amines using standard coupling procedures to provide amides such as 164. As shown in Scheme XIII, acid 159 is converted to its benzyl ester 165 and the amino blocking group of benzyl ester 165 is then removed. The resultant amino derivative is coupled to acid 147 using standard coupling procedures to give macrocycle precursor 166. Deprotection and cyclization provides macrocycle 167. Removal of the t-butyl ester blocking group followed by coupling to an amine gives macrocycles such as 168.

SCHEME XI

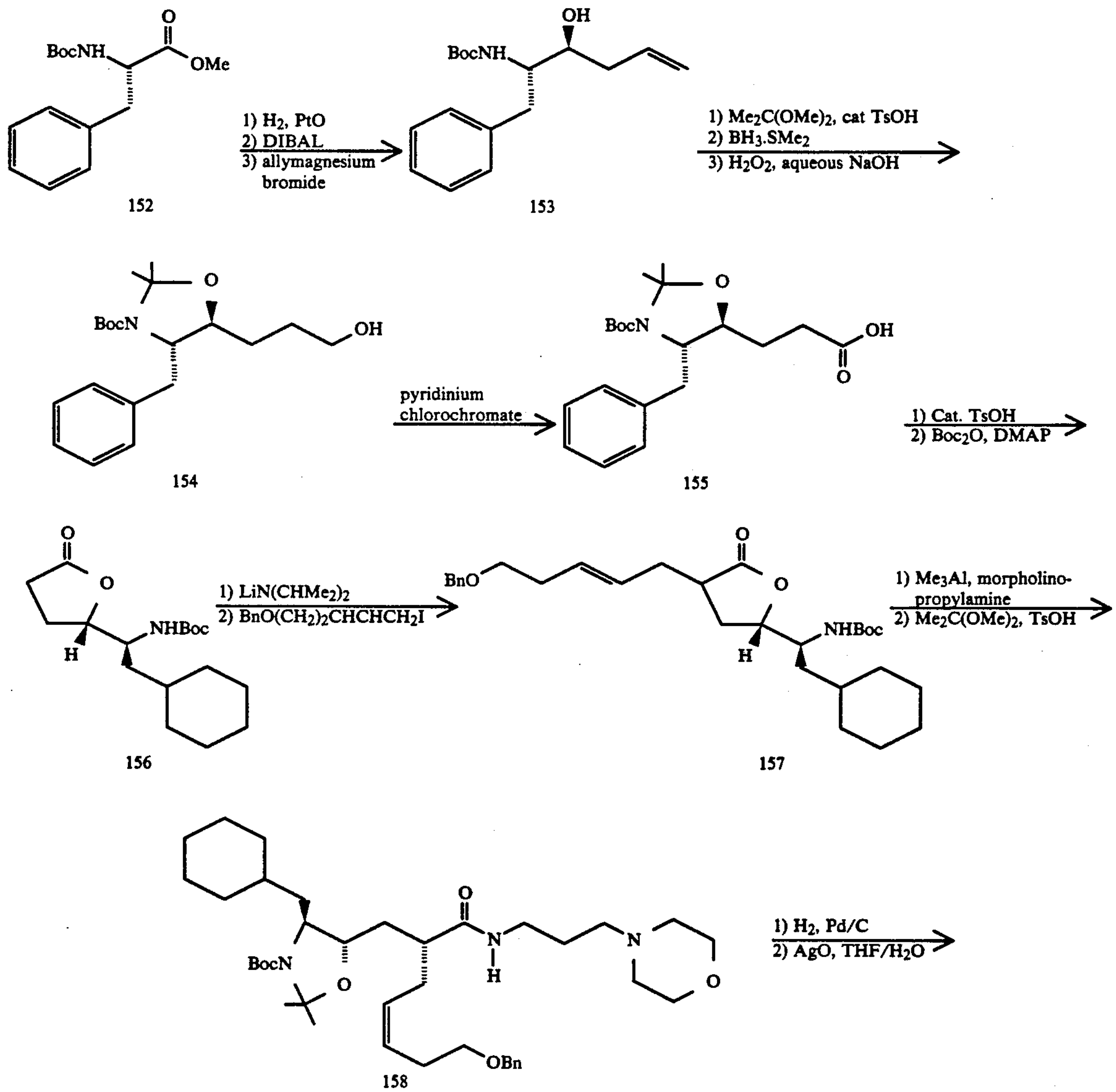

152 153 154 155 156 157 158

-continued
SCHEME XI
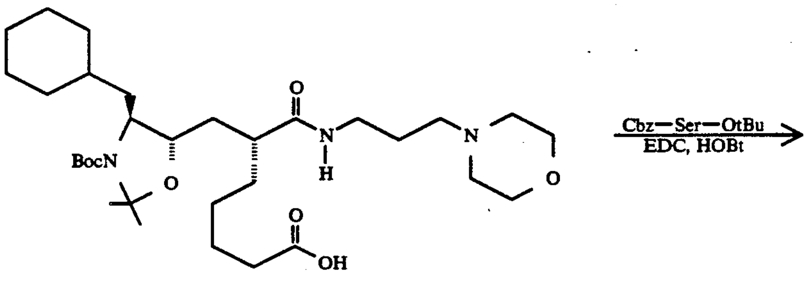
159
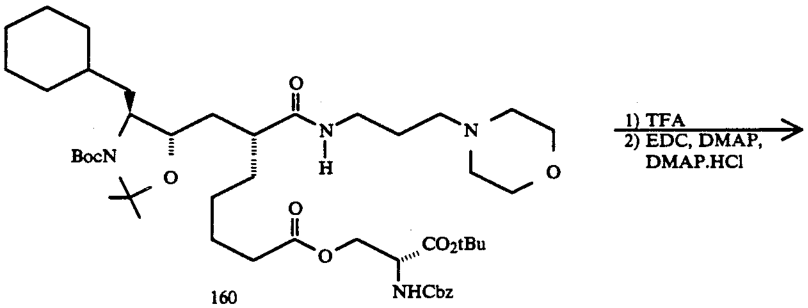
160
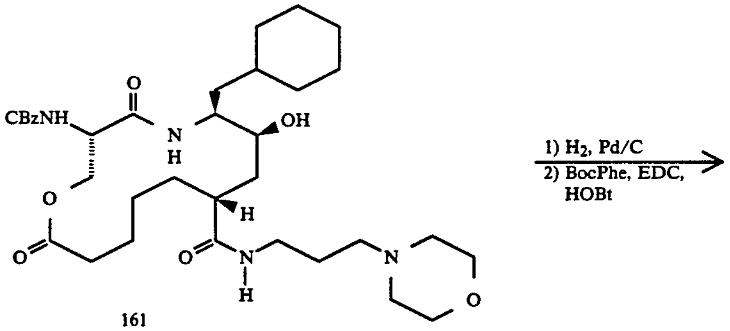
161
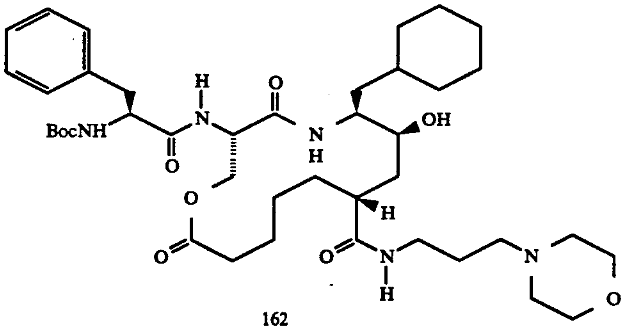
162

SCHEME XII
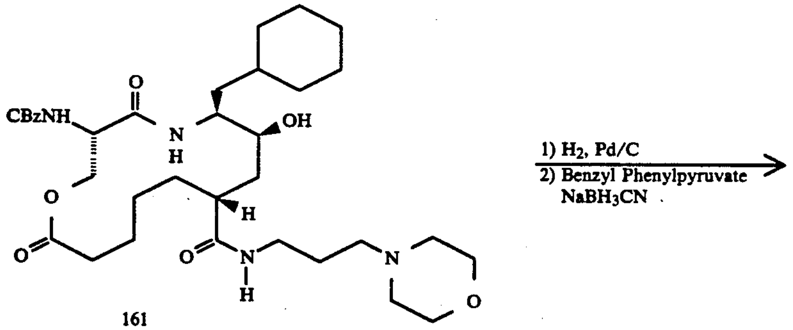
161
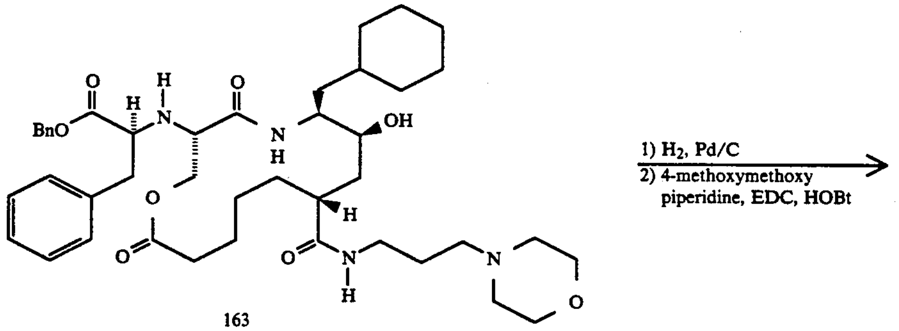
163
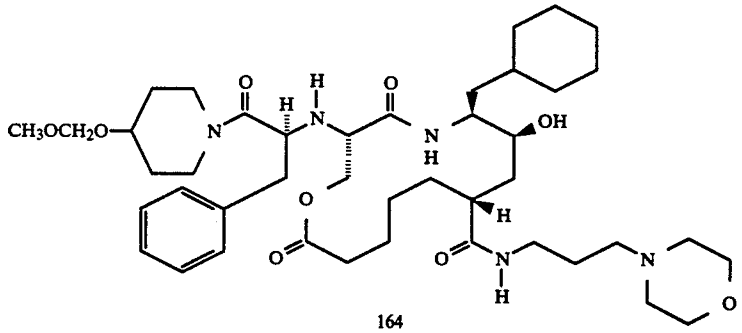
164
SCHEME XIII
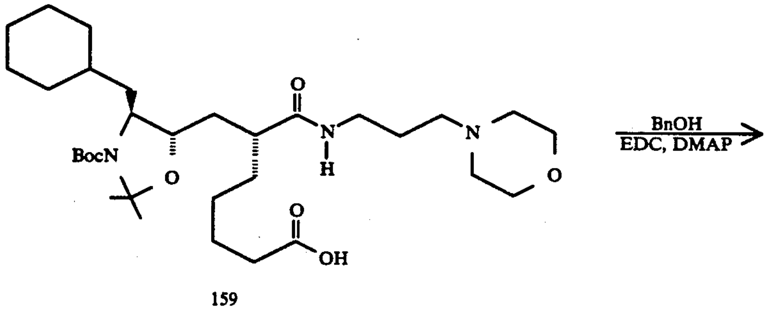
159

-continued

SCHEME XIII

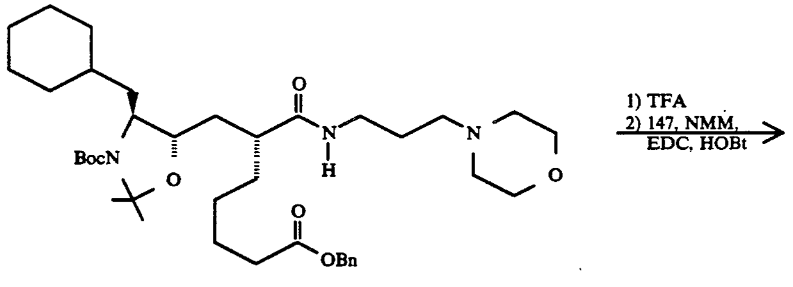

165

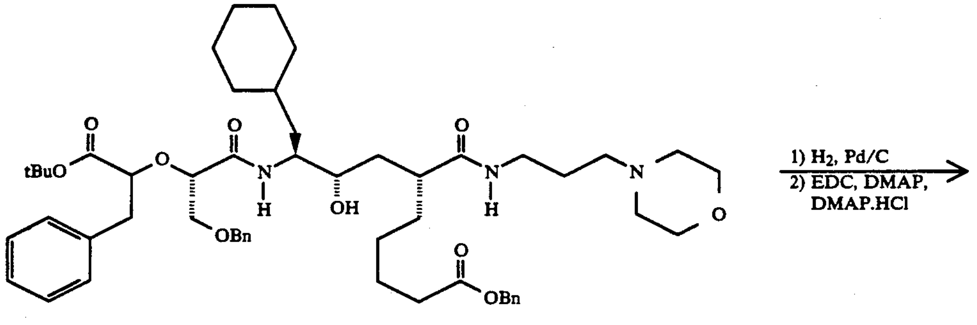

166

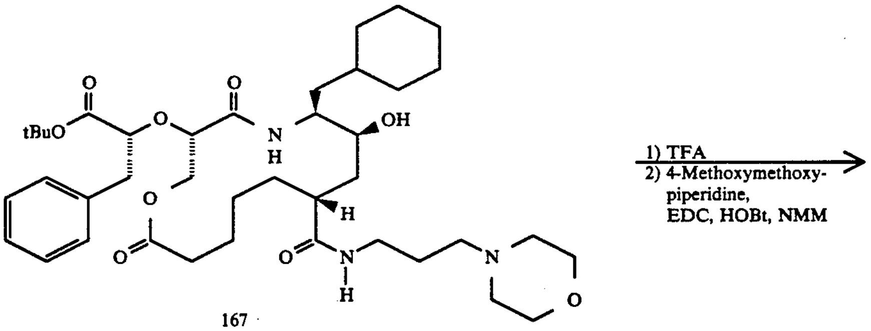

167

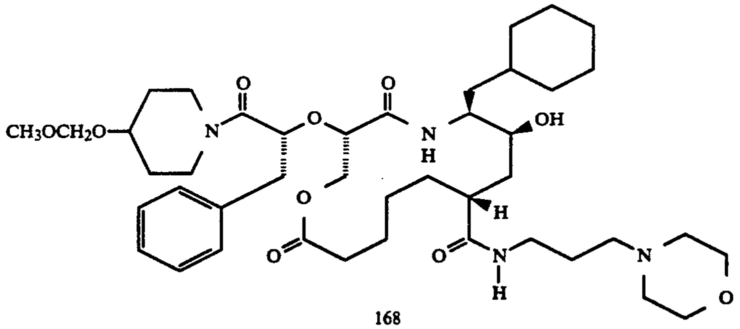

168

Preparation of Macrocyclic Renin Inhibitors of Formula I in which D=—S—, W=—NH—, s=0, t=5, and n=1

Scheme XIV and XV illustrate the preparation of macrocyclic renin inhibitors of the formula I in which D=—S—, W=—NH—, s=0, t=5, and n=1. As shown in Scheme XIV, intermediate 158 is converted to bromide 169. Alkylation of cystine with bromide 159 followed by protection of the free amine provides macrocycle precursor 170. Removal of the Boc acetonide functionality and macrocyclization gives macrocycle 171. After removal of the Cbz protecting group from 171, the resultant amino derivative is coupled with carboxylic acids, acid chlorides, or sulfonyl chlorides using standard coupling procedures to yield macrocycles such as 172. As shown in Scheme XV, the Cbz group of macrocycle 171 is removed and the resultant amino derivative is reductively alkylated with a 2-keto ester using standard procedures to provide esters such as 173. Ester 173 is converted to the corresponding acid and coupled with amines using standard coupling procedures to provide amides such as 174.
SCHEME XIV
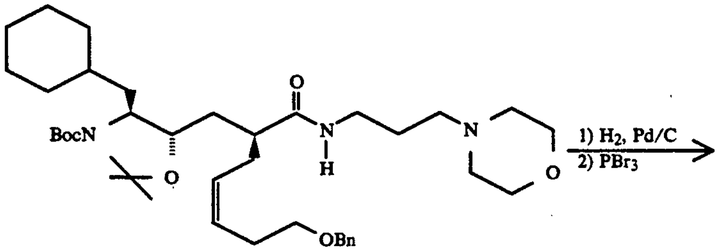
158
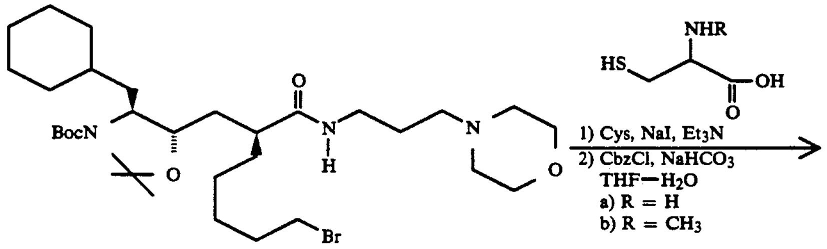
169
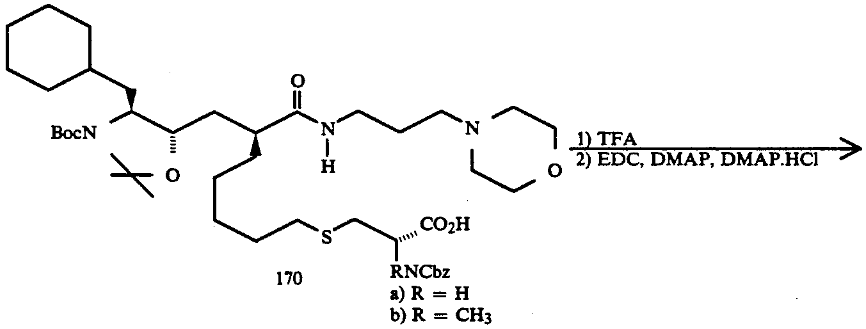
170
a) R = H
b) R = $CH_3$
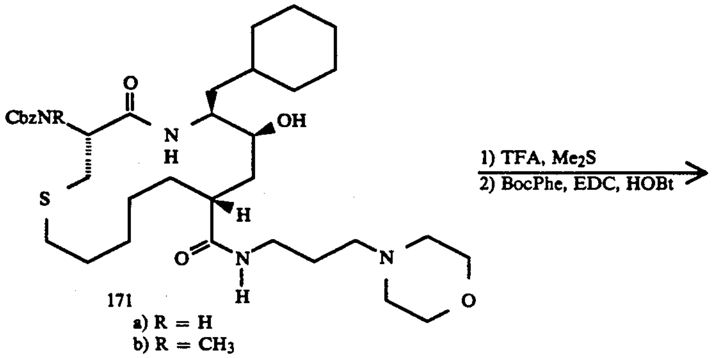
171
a) R = H
b) R = $CH_3$ -continued
SCHEME XIV
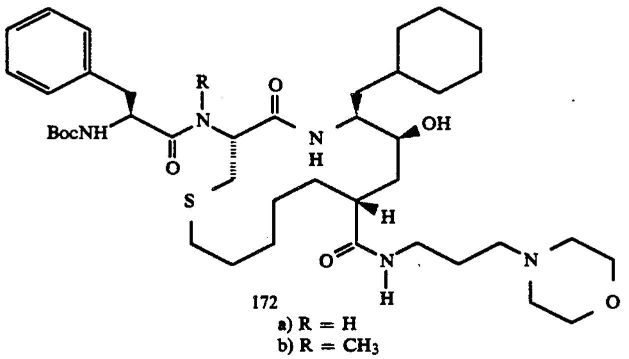
172
a) R = H
b) R = $CH_3$
SCHEME XV
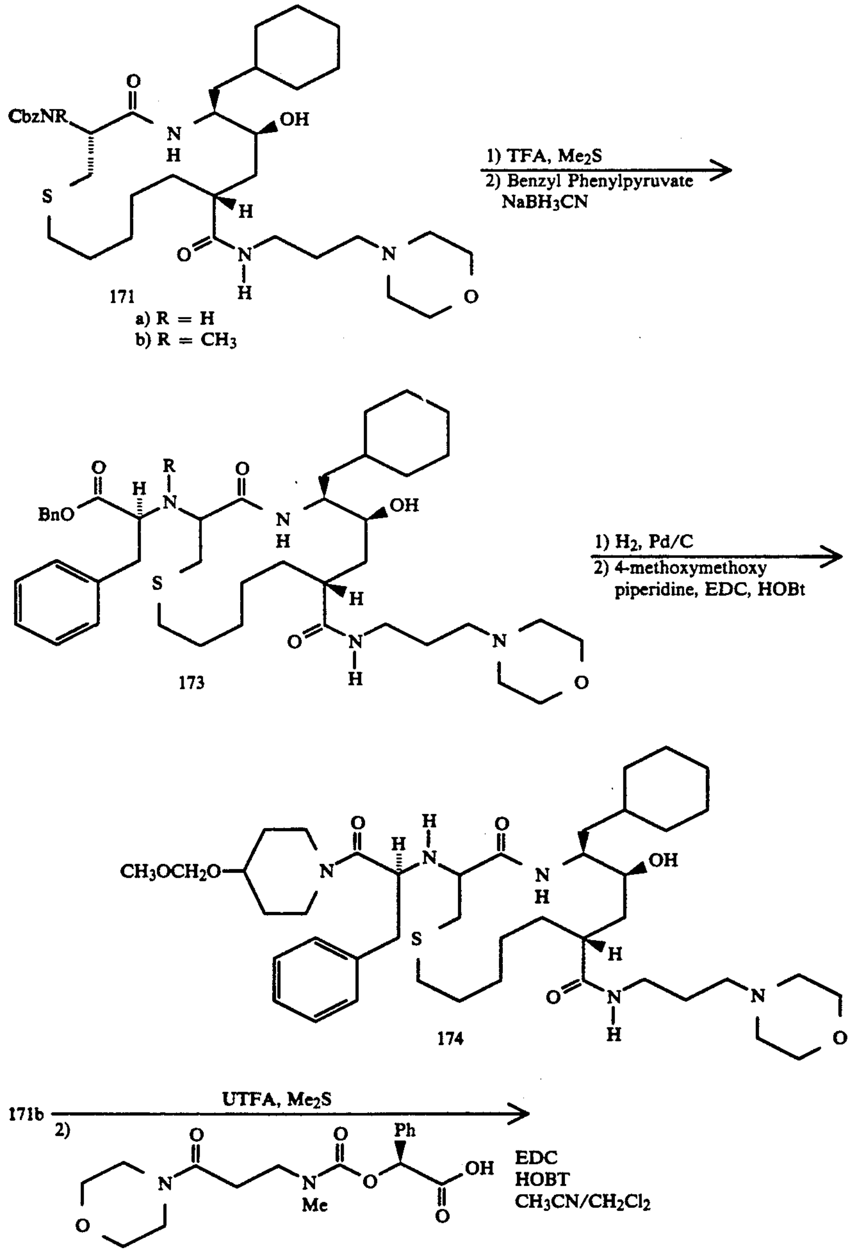
171
a) R = H
b) R = $CH_3$
173
174

-continued
SCHEME XV
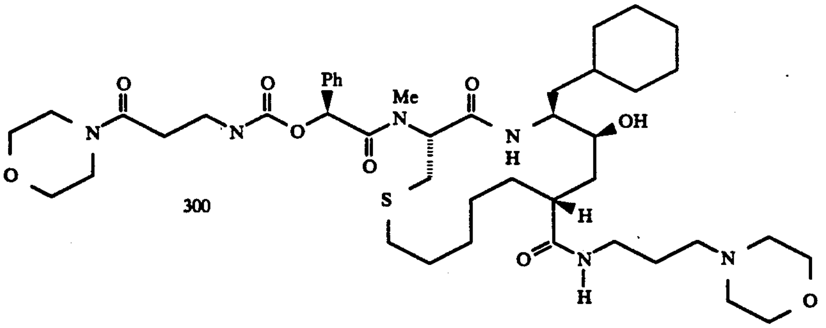
300
What is claimed is:
1. A compound of the formula:
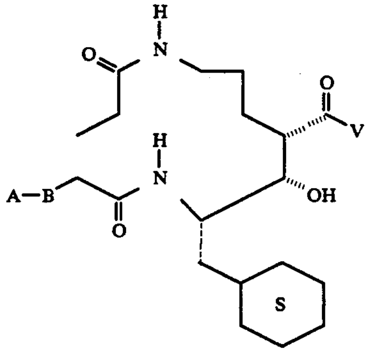
wherein A-B and V are selected from the group consisting of:
| Number | A—B | V |
|---|---|---|
| 11-1 | Boc—Phe—NH— | —NH-2(S)-methylbutyl |
| 11-2 | Boc—Phe—NH— | —OEt |
| 11-3 | Boc—Phe—NH— | —O-isobutyl |
| 11-4 | 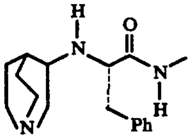 | 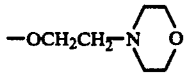 |
| 11-5 | Boc—Phe—NH— | 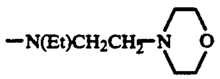 |
| 11-6 | 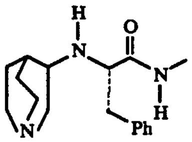 | —O-isobutyl |
| 11-7 | 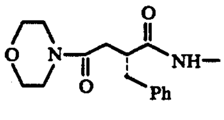 | 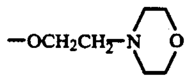 |
| 11-8 | 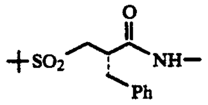 | —O-i-Pr |
| 11-9 | 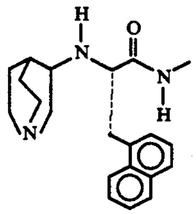 | —O-i-Pr |
| 11-10 | 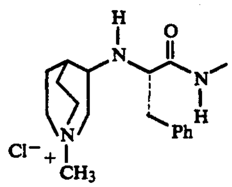 | —O-i-Pr |
| 11-11 | 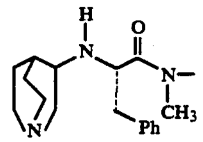 | —O-i-Pr |
| 11-12 | 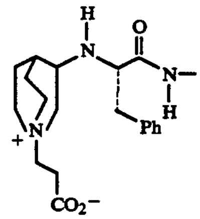 | —O-i-Pr |
| 11-13 | 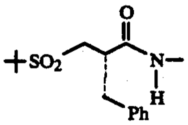 | 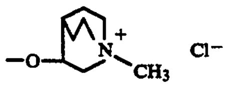 |
| 11-14 | 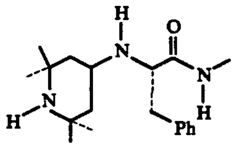 | —O-i-Pr |

-continued
| Number | A—B | V |
|---|---|---|
| 11-15 | 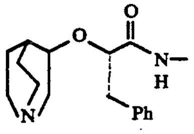 | —O-i-Pr |
| 11-16 | 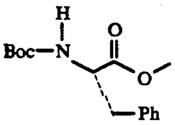 | —O-i-Pr |
| 11-17 | 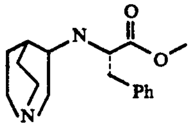 | 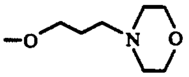 |
| 11-18 | 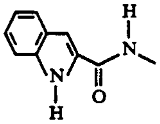 | 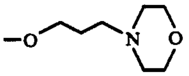 |
| 11-19 | 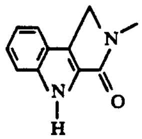 | 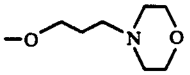 |
| 11-20 | 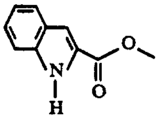 | 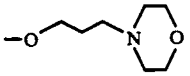 |
| 11-21 | 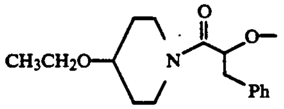 | 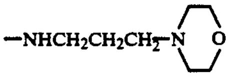 |
| 11-22 | 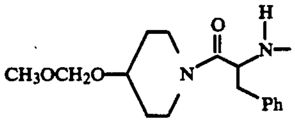 | 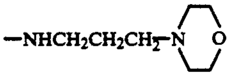 |
2. A compound of the formula:
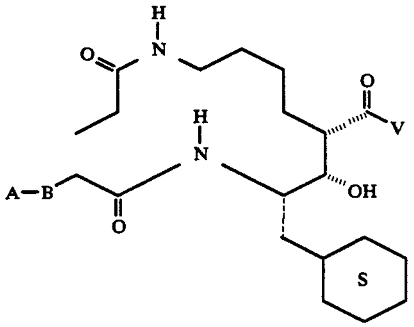
wherein A-B and V are selected from the group:
| Number | A—B | V |
|---|---|---|
| 18-1 | Boc—Phe—NH— | —$OCH_3$ |
| 18-2 | Boc—Phe—NH— | —NH-2(S)-methylbutyl |
| 18-3 | 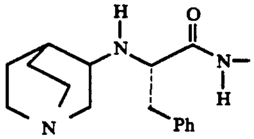 | —O-i-Pr |
| 18-4 | 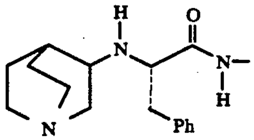 | 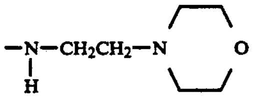 |
| 18-5 | 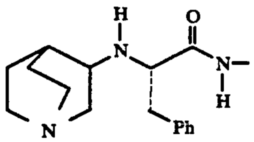 | 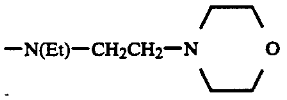 |
| 18-6 | 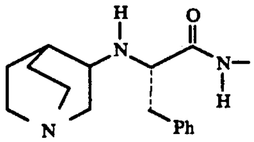 | 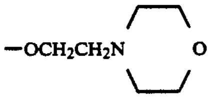 |

-continued
| Number | A—B | V |
|---|---|---|
| 18-7 | 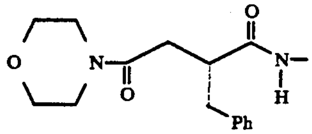 | —O-i-Pr |
| 18-8 | 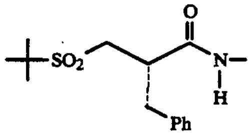 | —O-i-Bu |
| 18-9 | 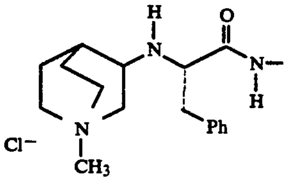 | —O-i-Pr |
| 18-10 | 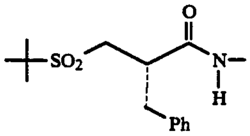 | 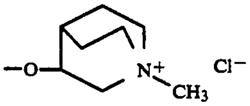 |
| 18-11 | 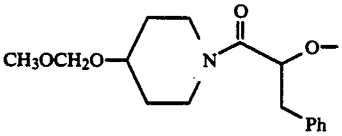 | 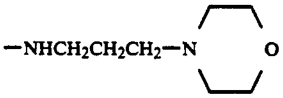 |
| 18-12 | 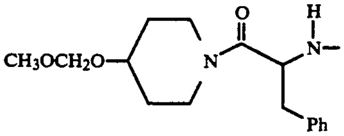 | 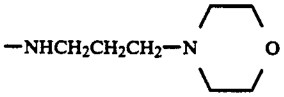 |
3. A compound of the formula:
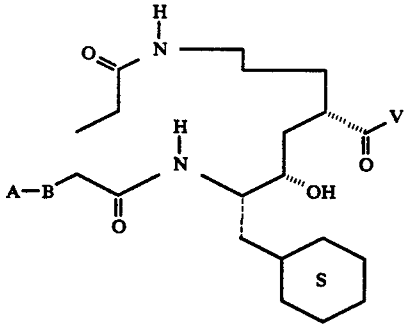
| Number | A—B | V |
|---|---|---|
| 210 | Boc—Phe—NH— | —NH-2(S)-methylbutyl |
| 211 | Boc—Phe—NH— | —OEt |
| 212 | Boc—Phe—NH— | —O-isobutyl |
| 213 | 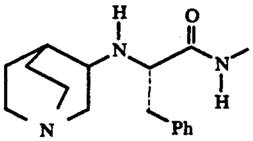 | 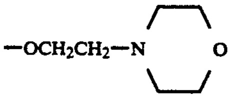 |

-continued
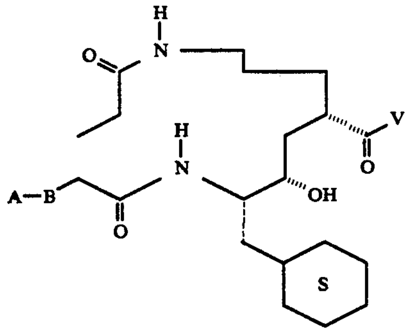
| Number | A—B | V |
|---|---|---|
| 214 | Boc—Phe—NH— | —N(Et)$CH_2CH_2$— 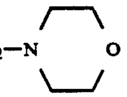 |
| 215 | 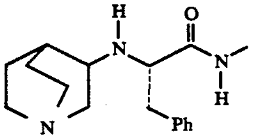 | —O-isobutyl |
| 216 | 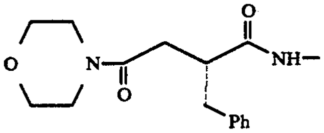 | —$OCH_2CH_2$— 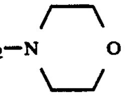 |
| 217 | 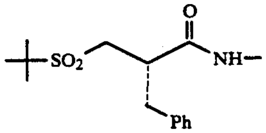 | —O-i-Pr |
| 218 | 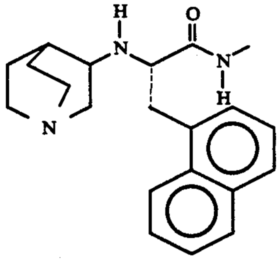 | —O-i-Pr |
| 219 | 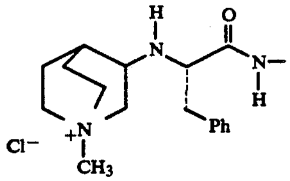 | —O-i-Pr |
| 220 | 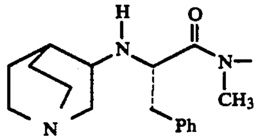 | —O-i-Pr |

-continued
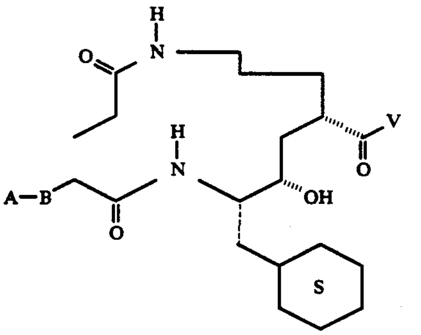
| Number | A—B | V |
|---|---|---|
| 221 | 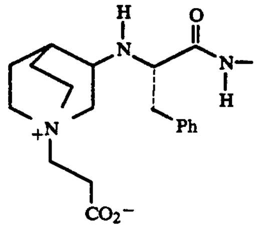 | —O-i-Pr |
| 222 | 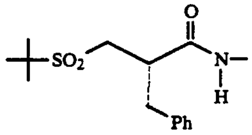 | 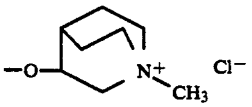 |
| 223 | 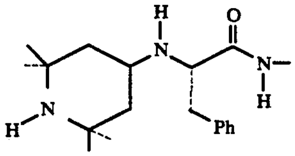 | —O-i-Pr |
| 224 | 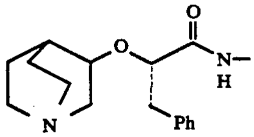 | —O-i-Pr |
| 225 | 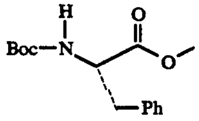 | —O-i-Pr |
| 226 | 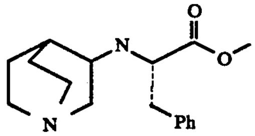 | 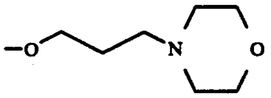 |
| 227 | 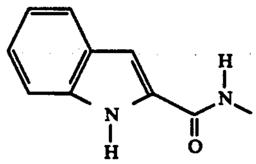 | 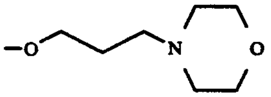 |

-continued
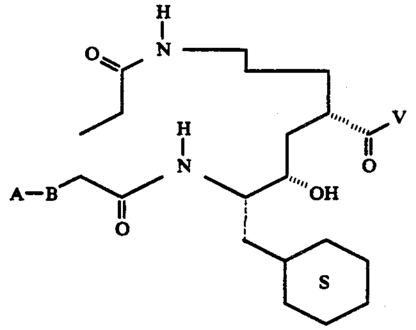
| Number | A—B | V |
|---|---|---|
| 228 | 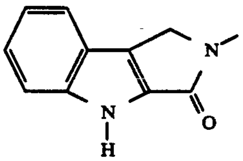 | 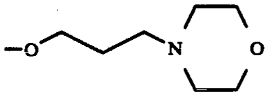 |
| 229 | 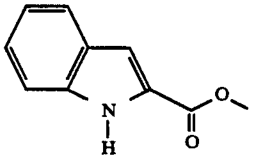 | 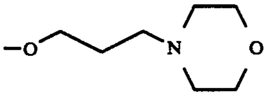 |
| 230 | 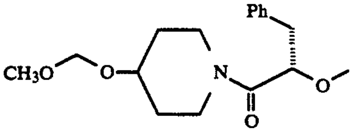 | 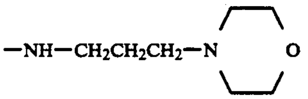 |
| 231 | 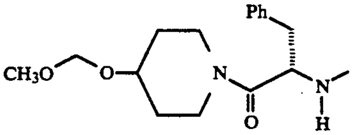 | 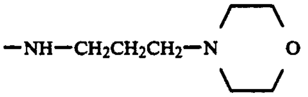 |
4. A compound of the formula:
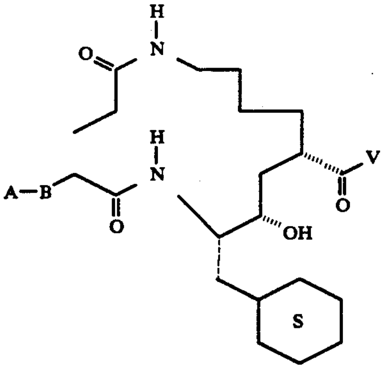
where A-B and V are selected from the group consisting of:
| Number | A—B | V |
|---|---|---|
| 232 | Boc—Phe—NH— | —$OCH_3$ |
| 233 | Boc—Phe—NH— | —NH-2(S)-methylbutyl |

-continued
| Number | A—B | V |
| --- | --- | --- |
| 234 | 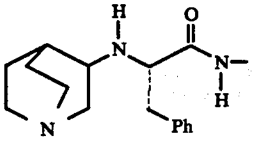 | —O-i-Pr |
| 235 | 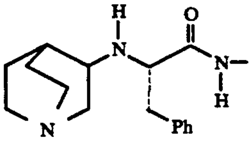 | 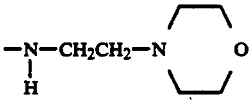 |
| 236 | 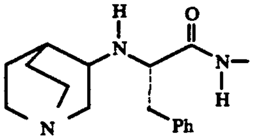 | 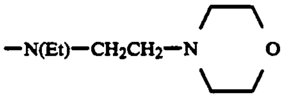 |
| 237 | 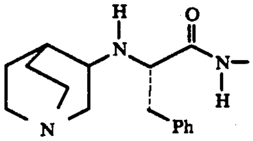 | 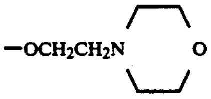 |
| 238 | 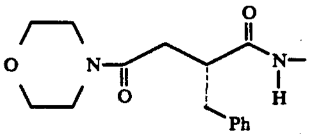 | —O-i-Pr |
| 239 | 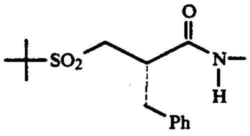 | —O-i-Bu |
| 240 | 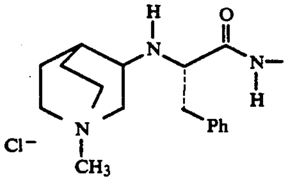 | —O-i-Pr |
| 241 | 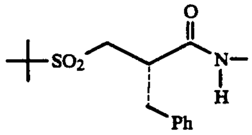 | 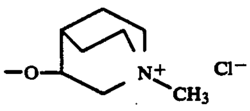 |
| 242 | 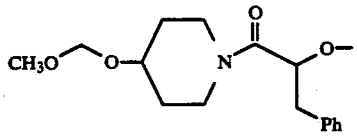 | 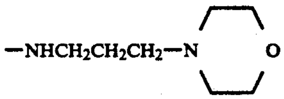 |
| 243 | 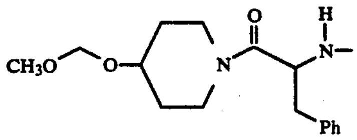 | 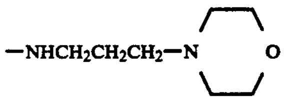 |
* * * * *